(12) United States Patent
Nakazawa et al.

(10) Patent No.: US 10,683,355 B2
(45) Date of Patent: Jun. 16, 2020

(54) GENETICALLY-MODIFIED CELLS AND METHOD FOR PRODUCING SAME

(71) Applicants: KISSEI PHARMACEUTICAL CO., LTD., Matsumoto-shi, Nagano (JP); SHINSHU UNIVERSITY, Matsumoto-shi, Nagano (JP)

(72) Inventors: Yozo Nakazawa, Matsumoto (JP); Kazuyuki Matsuda, Matsumoto (JP); Shigeru Nakano, Azumino (JP)

(73) Assignees: KISSEI PHARMACEUTICAL CO., LTD., Matsumoto-shi, Nagano (JP); SHINSHU UNIVERSITY, Matsumoto-shi, Nagano (JP)

( * ) Notice: Subject to any disclaimer, the term of this patent is extended or adjusted under 35 U.S.C. 154(b) by 0 days.

(21) Appl. No.: 16/333,916

(22) PCT Filed: Sep. 15, 2017

(86) PCT No.: PCT/JP2017/033582
§ 371 (c)(1),
(2) Date: Mar. 15, 2019

(87) PCT Pub. No.: WO2018/052142
PCT Pub. Date: Mar. 22, 2018

(65) Prior Publication Data
US 2019/0202923 A1 Jul. 4, 2019

(30) Foreign Application Priority Data
Sep. 16, 2016 (JP) ................... 2016-182293

(51) Int. Cl.
| | | |
|---|---|---|
| A61K 39/00 | (2006.01) | |
| A61K 48/00 | (2006.01) | |
| C07K 16/30 | (2006.01) | |
| C07K 19/00 | (2006.01) | |
| C12N 5/0783 | (2010.01) | |
| C07K 16/28 | (2006.01) | |
| A61K 31/7088 | (2006.01) | |
| C12N 5/10 | (2006.01) | |
| C07K 16/24 | (2006.01) | |
| C07K 14/535 | (2006.01) | |
| A61K 35/12 | (2015.01) | |
| A61P 43/00 | (2006.01) | |
| A61P 35/00 | (2006.01) | |
| A61K 35/17 | (2015.01) | |
| C07K 14/725 | (2006.01) | |
| C07K 14/705 | (2006.01) | |
| C12N 15/113 | (2010.01) | |
| A61K 38/00 | (2006.01) | |

(52) U.S. Cl.
CPC ...... *C07K 16/2866* (2013.01); *A61K 31/7088* (2013.01); *A61K 35/12* (2013.01); *A61K 35/17* (2013.01); *A61K 39/001139* (2018.08); *A61K 48/00* (2013.01); *A61P 35/00* (2018.01); *A61P 43/00* (2018.01); *C07K 14/535* (2013.01); *C07K 14/7051* (2013.01); *C07K 14/70521* (2013.01); *C07K 14/70578* (2013.01); *C07K 16/243* (2013.01); *C07K 19/00* (2013.01); *C12N 5/0636* (2013.01); *C12N 5/10* (2013.01); *C12N 15/1136* (2013.01); *A61K 38/00* (2013.01); *A61K 2039/5156* (2013.01); *A61K 2039/5158* (2013.01); *A61K 2039/572* (2013.01); *C07K 2317/524* (2013.01); *C07K 2317/526* (2013.01); *C07K 2317/53* (2013.01); *C07K 2317/622* (2013.01); *C07K 2317/76* (2013.01); *C07K 2319/02* (2013.01); *C07K 2319/03* (2013.01); *C07K 2319/30* (2013.01); *C12N 2310/122* (2013.01); *C12N 2310/14* (2013.01); *C12N 2310/531* (2013.01); *C12N 2510/00* (2013.01)

(58) Field of Classification Search
None
See application file for complete search history.

(56) References Cited

U.S. PATENT DOCUMENTS

| | | |
|---|---|---|
| 2014/0242701 A1 | 8/2014 | Shiku et al. |
| 2017/0051308 A1* | 2/2017 | Morgan ............ C07K 16/2803 |
| 2018/0289742 A1 | 10/2018 | Nishio et al. |

FOREIGN PATENT DOCUMENTS

| | | |
|---|---|---|
| JP | 63-502795 A | 10/1988 |
| WO | 87/02060 A1 | 4/1987 |
| WO | 2013/051718 A1 | 4/2013 |
| WO | 2014/127261 A1 | 8/2014 |

(Continued)

OTHER PUBLICATIONS

Nakazawa et al, Anti-proliferative effects of T cells expressing a ligand-based chimeric antigen receptor against CD116 on CD34+ cells of juvenile myelomonocytic leukemia, Journal of Hematology & Oncology (2016) 9:27 pp. 1-11.*

(Continued)

*Primary Examiner* — Maria Marvich
(74) *Attorney, Agent, or Firm* — Westerman, Hattori, Daniels & Adrian, LLP

(57) ABSTRACT

Production of a chimeric antigen receptor (CAR) expressing cell having excellent target cytotoxicity. Provided is a genetically modified cell comprising, introduced thereinto, a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain.

6 Claims, 41 Drawing Sheets
Specification includes a Sequence Listing.

(56) References Cited

FOREIGN PATENT DOCUMENTS

| WO | 2015/066262 A1 | 5/2015 |
|---|---|---|
| WO | 2015/090229 A1 | 6/2015 |
| WO | 2015/124715 A1 | 8/2015 |
| WO | 2017/061615 A1 | 4/2017 |

OTHER PUBLICATIONS

Srivastava adn Riddell, Chimeric Antigen Receptor T Cell Therapy: Challenges to Bench-to-Bedside Efficacy, The Journal of Immunology, 2018, pp. 459-468.*
Elahi et al, Immune Cell Hacking: Challenges and Clinical Approaches to Create Smarter Generations of Chimeric Antigen Receptor T Cells, Frontiers in Immunology, 2018, pp. 1-18.*
Niu and Wang, In vitro human cell line models to predict clinical response to anticancer drugs, 2015, Pharnacogenomics, pp. 273-285.*
Nakazawa et al., "Anti-proliferative effects of T cells expressing a ligand-based chimeric antigen receptor against CD116 on CD34+ cells of juvenile myelomonocytic leukemia", Journal of Hematology & Oncology, 2016, vol. 9, No. 27, 11 pages (in English; cited in the ISR and Declaration as to Non-prejudicial Disclosures or Exceptions to Lack of Novelty submitted in Int'l Appl. No. PCT/JP2017/033582).
Nakano et al., "Ligand-based chimeric antigen receptor-modified T cells targeting CD116 for the treatment of acute myeloid leukemia", The 22nd Annual Meeting JSGCT2016: Japan Society of Gene and Cell Therapy Program and Abstracts, Jul. 13, 2016, PO-70 (3 pages; in English; cited in the ISR and Declaration as to Non-prejudicial Disclosures or Exceptions to Lack of Novelty submitted in Int'l Appl. No. PCT/JP2017/033582).
Nakazawa, "Treatment of Childhood Cancers by Genetically Modified T Cells", Japanese Journal of Pediatric Medicine, Jul. 2017, vol. 49, No. 7, pp. 1017-1023 (27 pages including English translation; cited in the ISR).
Nakano et al., "Ligand-based chimeric antigen receptor-modified T cells targeting CD116 for the treatment of acute myeloid leukemia", The 22nd Annual Meeting JSGCT2016: Japan Society of Gene and Cell Therapy Schedule and Presentation, Jul. 28, 2016 (3 pages; in English; cited in Declaration as to Non-prejudicial Disclosures or Exceptions to Lack of Novelty submitted in Int'l Appl. No. PCT/JP2017/033582).
Kakenhi, Grants-in-Aid for Scientific Research: Report on Research Results, Project No. 24390260, Jun. 10, 2015 (16 pages including English translation).
Kaken—Search Research Projects, 2011 Fiscal Year Annual Research Report (KAKENHI-PROJECT-23931038), Jun. 25, 2013 (6 pages including English translation).
Kaken—Search Research Projects, 2012 Fiscal Year Annual Research Report (KAKENHI-PROJECT-24390260), Jul. 16, 2014 (9 pages including English translation).
Kaken—Search Research Projects, 2013 Fiscal Year Annual Research Report (KAKENHI-PROJECT-24390260), May 28, 2015 (11 pages including English translation).
Kaken—Search Research Projects, 2014 Fiscal Year Annual Research Report (KAKENHI-PROJECT-24390260), Jun. 1, 2016 (9 pages including English translation).
Nakazawa et al., "Development of Gene-Modified T-Cell Therapy Targeting GM-CSF Receptor for Juvenile Myelomonocytic Leukemia", Abstract O-87 for the 55th Annual Meeting of the Japanese Society of Pediatric Hematology/Oncology, 2013 (3 pages including English translation).
English translation of "Declaration as to Non-prejudicial Disclosures or Exceptions to Lack of Novelty" under PCT Rules 4.17(v), 51bis.1, 51bis.2, as submitted in the counterpart International Application No. PCT/JP2017/033582 filed on Sep. 15, 2017 (1 page).
Nakazawa, "Gene-modified T-cell Therapy Using Chimeric Antigen Receptor", The Shinshu Medical Journal, vol. 61, No. 4, 2013, pp. 197-203 (w/ English translation; cited in the Specification).
Shaffer et al., "Foreign or Domestic CARs: Receptor Ligands as Antigen-Binding Domains", Medical Sciences, 2014, vol. 2, pp. 23-36 (in English; cited in the Specification and ISR).
Office Action dated Jan. 21, 2020 issued in counterpart Japanese Application No. 2018-539204 (w/ English translation; 10 pages).

* cited by examiner

Fig. 15
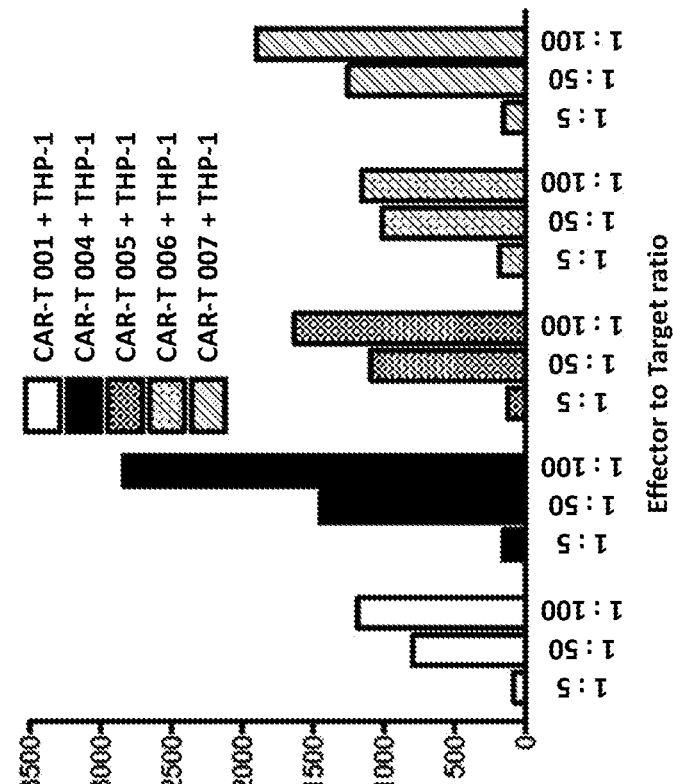
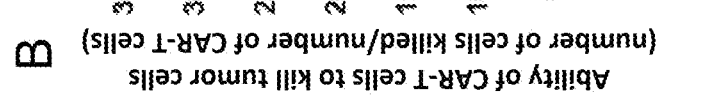
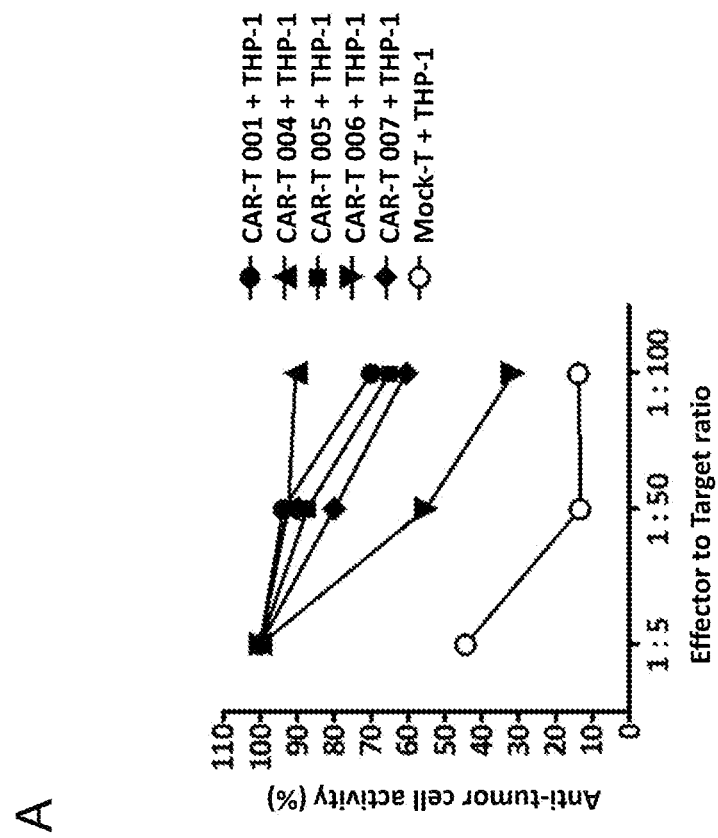

Fig. 17
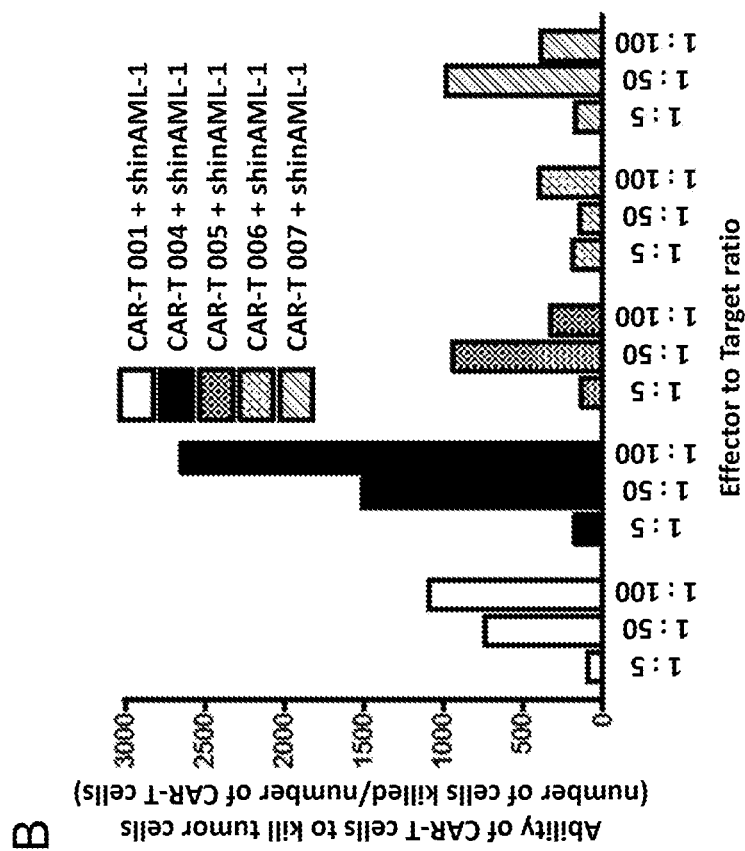
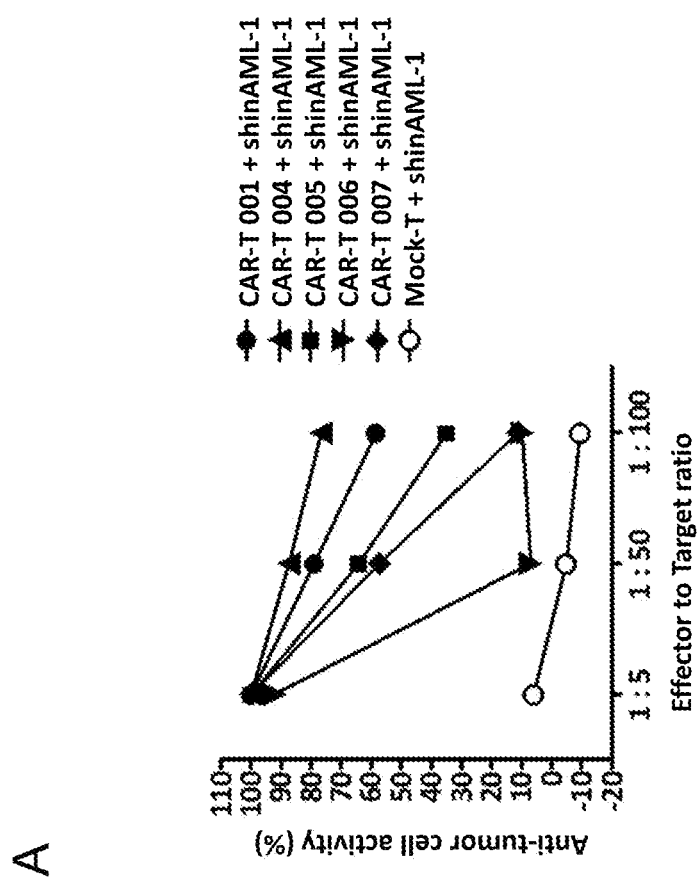

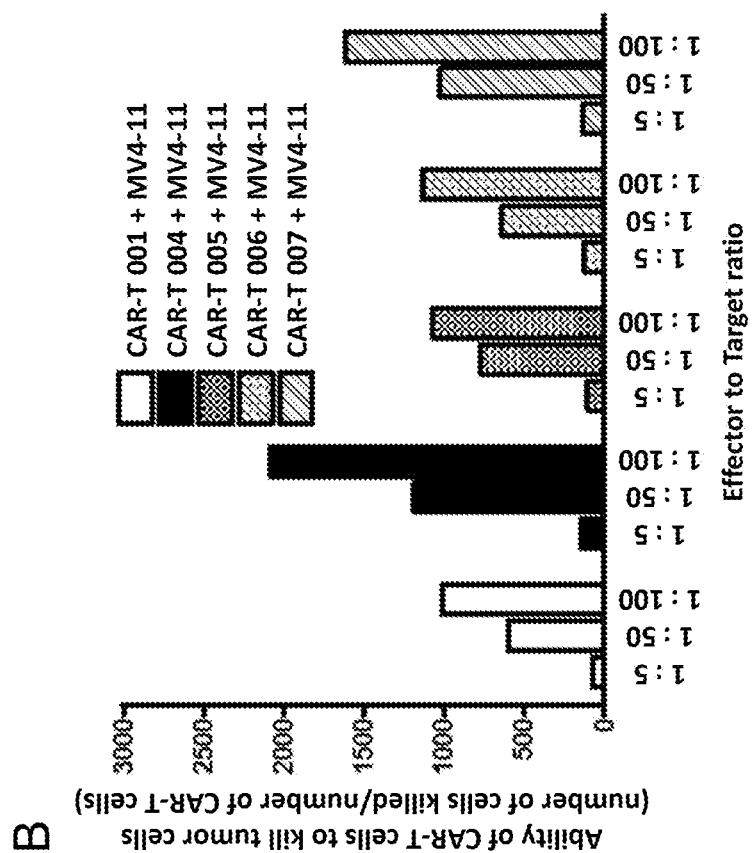
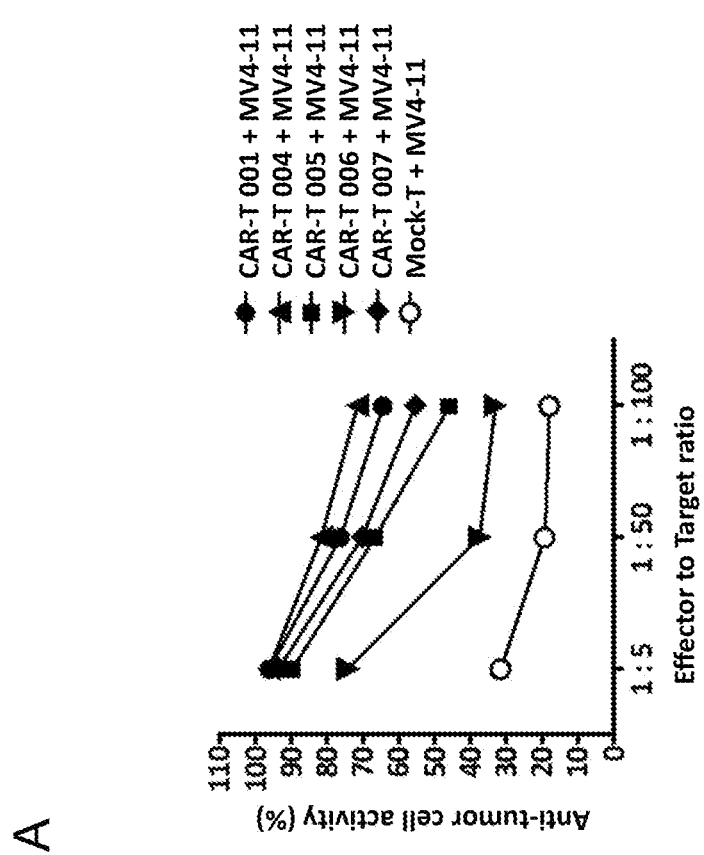
Fig. 18

Fig. 20
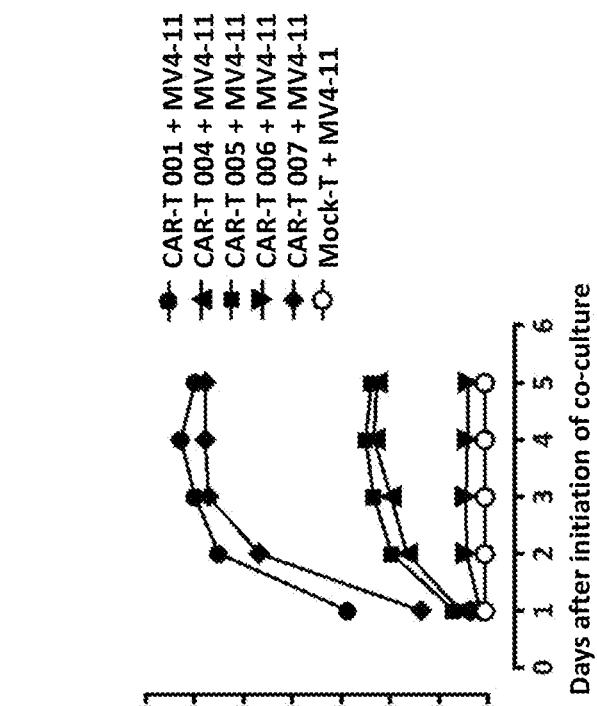
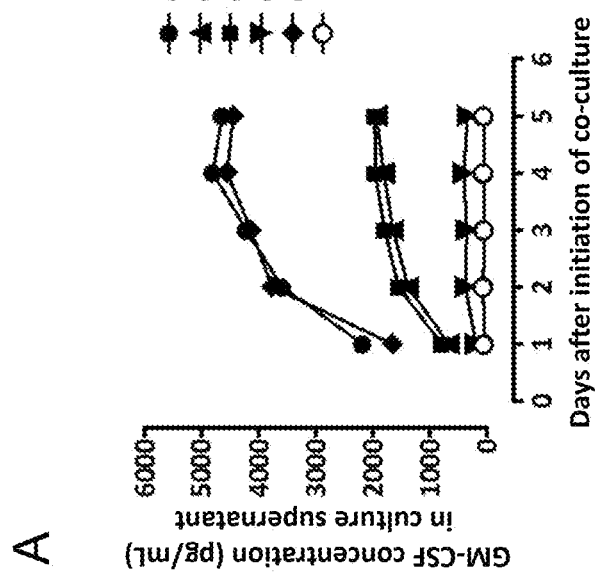

Fig. 30

Target; THP-1

Effector to Target ratio =1:1

| Days after initiation of co-culture | Term 1 | | Term 2 | | | Term 3 | | Term 4 | |
|---|---|---|---|---|---|---|---|---|---|
| | 0 | 4 | 4 | 8 | 8 | 12 | 12 | 15 |
| THP-1 alone | 250000 | 1216140 | 250000 | 1067430 | 250000 | 1199770 | 250000 | 1294650 |
| Mock-T | 250000 | 1021260 | | | | | | |
| CAR-T 001 | 250000 | 42460 | 271230 | 1230 | 250615 | 4210 | 252105 | 11480 |
| CAR-T 008 | 250000 | 32050 | 266025 | 6800 | 253400 | 7830 | 253915 | 12940 |
| CAR-T 009 | 250000 | 30760 | 265380 | 7480 | 253740 | 7740 | 253870 | 2480 |
| CAR-T 010 | 250000 | 55200 | 277600 | 2510 | 251255 | 10100 | 255050 | 2130 |
| CAR-T 011 | 250000 | 13170 | 256585 | 100550 | 300275 | 457150 | | |

Effector to Target ratio =1:5

| Days after initiation of co-culture | Term 1 | | Term 2 | | | Term 3 | | Term 4 | |
|---|---|---|---|---|---|---|---|---|---|
| | 0 | 4 | 4 | 8 | 8 | 12 | 12 | 15 |
| THP-1 alone | 250000 | 1216140 | 250000 | 1067430 | 250000 | 1199770 | 250000 | 1294650 |
| Mock-T | 250000 | 1281590 | | | | | | |
| CAR-T 001 | 250000 | 15530 | 257765 | 1570 | 250785 | 1660 | 250830 | 514140 |
| CAR-T 008 | 250000 | 16780 | 258390 | 1520 | 250760 | 50750 | 275375 | 543980 |
| CAR-T 009 | 250000 | 41890 | 270945 | 2150 | 251075 | 33020 | 266510 | 609210 |
| CAR-T 010 | 250000 | 15460 | 257730 | 2760 | 251380 | 1770 | 250885 | 345670 |
| CAR-T 011 | 250000 | 237130 | 368565 | 395860 | | | | |

Fig. 31

Target; MV4-11

Effector to Target ratio =1:1

| Days after initiation of co-culture | Term 1 | | Term 2 | | Term 3 | | Term 4 | |
|---|---|---|---|---|---|---|---|---|
| | 0 | 4 | 4 | 8 | 8 | 12 | 12 | 15 |
| MV4-11 alone | 250000 | 860440 | 250000 | 758410 | 250000 | 793790 | 250000 | 827340 |
| Mock-T | 250000 | 725310 | | | | | | |
| CAR-T 001 | 250000 | 41720 | 270860 | 10190 | 255095 | 12490 | 256245 | 22760 |
| CAR-T 008 | 250000 | 44120 | 272060 | 12230 | 256115 | 31600 | 265800 | 405830 |
| CAR-T 009 | 250000 | 37580 | 268790 | 19960 | 259980 | 10400 | 255200 | 476510 |
| CAR-T 010 | 250000 | 54570 | 277285 | 12890 | 256445 | 38970 | 269485 | 38390 |
| CAR-T 011 | 250000 | 36340 | 268170 | 14580 | 257290 | 246540 | 373270 | 466050 |

Effector to Target ratio =1:5

| Days after initiation of co-culture | Term 1 | | Term 2 | | Term 3 | | Term 4 | |
|---|---|---|---|---|---|---|---|---|
| | 0 | 4 | 4 | 8 | 8 | 12 | 12 | 15 |
| MV4-11 alone | 250000 | 860440 | 250000 | 758410 | 250000 | 793790 | 250000 | 827340 |
| Mock-T | 250000 | 855110 | | | | | | |
| CAR-T 001 | 250000 | 28320 | 264160 | 17480 | 258740 | 9040 | 254520 | 537140 |
| CAR-T 008 | 250000 | 38740 | 269370 | 16150 | 258075 | 312390 | | |
| CAR-T 009 | 250000 | 198750 | 349375 | 24010 | 262005 | 343600 | | |
| CAR-T 010 | 250000 | 35380 | 267690 | 20400 | 260200 | 13390 | 256695 | 478600 |
| CAR-T 011 | 250000 | 456100 | | | | | | |

Fig. 36

Target; THP-1

Effector to Target ratio =1:1

|  | Term 1 | | Term 2 | |
| --- | --- | --- | --- | --- |
| Days after initiation of co-culture | 0 | 4 | 4 | 8 |
| THP-1 alone | 250000 | 1129560 | 250000 | 1213700 |
| Mock-T | 250000 | 693180 | | |
| CAR-T 008 | 250000 | 13930 | 256965 | 2470 |
| CAR-T 012 | 250000 | 20030 | 260015 | 5620 |
| CAR-T 010 | 250000 | 12690 | 256345 | 2970 |
| CAR-T 014 | 250000 | 31120 | 265560 | 9110 |

Effector to Target ratio =1:5

|  | Term 1 | | Term 2 | |
| --- | --- | --- | --- | --- |
| Days after initiation of co-culture | 0 | 4 | 4 | 8 |
| THP-1 alone | 250000 | 1129560 | 250000 | 1213700 |
| Mock-T | 250000 | 817640 | | |
| CAR-T 008 | 250000 | 22860 | 261430 | 2820 |
| CAR-T 012 | 250000 | 151400 | 325700 | 434550 |
| CAR-T 010 | 250000 | 2830 | 251415 | 2100 |
| CAR-T 014 | 250000 | 47560 | 273780 | 22750 |

Fig. 37

Target; MV4-11

Effector to Target ratio =1:1

|  | Term 1 | | Term 2 | |
|---|---|---|---|---|
| Days after initiation of co-culture | 0 | 4 | 4 | 8 |
| MV4-11 alone | 250000 | 768080 | 250000 | 441570 |
| Mock-T | 250000 | 397900 | | |
| CAR-T 008 | 250000 | 2680 | 251340 | 1330 |
| CAR-T 012 | 250000 | 5870 | 252935 | 4350 |
| CAR-T 010 | 250000 | 2370 | 251185 | 500 |
| CAR-T 014 | 250000 | 6530 | 253265 | 1850 |

Effector to Target ratio =1:5

|  | Term 1 | | Term 2 | |
|---|---|---|---|---|
| Days after initiation of co-culture | 0 | 4 | 4 | 8 |
| MV4-11 alone | 250000 | 768080 | 250000 | 441570 |
| Mock-T | 250000 | 475870 | | |
| CAR-T 008 | 250000 | 3570 | 251785 | 38490 |
| CAR-T 012 | 250000 | 30190 | 265095 | 3910 |
| CAR-T 010 | 250000 | 1400 | 250700 | 7820 |
| CAR-T 014 | 250000 | 3080 | 251540 | 4260 |

GENETICALLY-MODIFIED CELLS AND METHOD FOR PRODUCING SAME

CROSS-REFERENCE TO RELATED APPLICATIONS

This application is a National Stage entry of International Application No. PCT/JP2017/033582 filed on Sep. 15, 2017, which claims priority from Japanese Patent Application No. 2016-182293 filed on Sep. 16, 2016, the entire disclosure of each of which is herein incorporated by reference.

TECHNICAL FIELD

The present invention relates to a genetically modified cell expressing a chimeric antigen receptor and useful in the field of adoptive immunotherapy, and also relates to a method for producing the cell.

More specifically, the present invention relates to a genetically modified cell comprising, introduced thereinto, a polynucleotide encoding a human granulocyte-macrophage colony stimulating factor (GM-CSF) receptor-specific chimeric antigen receptor having excellent targeted cytotoxicity; a genetically modified cell comprising the above polynucleotide introduced thereinto together with a polynucleotide that induces RNAi to human GM-CSF; and methods for producing these cells and medicinal use of the cells.

BACKGROUND ART

An adoptive immunotherapy using T cells (CAR-T), which express a chimeric antigen receptor (CAR) targeting a tumor-associated antigen, has been reported to exert a powerful antitumor effect, and rapidly developed in recent years. In particular, development of a CAR targeting CD19 has been advanced. The CAR exerts remarkable effects in clinical trials and highly attracts attention. In general, the CAR is a protein having a single-stranded polypeptide derived from an antibody and retaining the binding ability to an antigen, a single-chain antibody (scFv), as a target binding domain and having an intracellular signaling domain linked thereto. Typically, an antibody polypeptide, in which Fv regions of an immunoglobulin heavy-chain (H chain) and light-chain (L chain) fragments are linked, is used as a target binding domain (Non Patent Literature 1).

The CAR-T therapy is highly effective; however, side effects are frequently produced, as is found in clinical trials. Particularly, since a mouse-derived single-chain antibody (scFv) is used as an antigen-binding domain, in most cases, an undesirable immune response occurs, leading to a risk of inducing serious anaphylactic shock. Accordingly, it is required to provide a CAR having an excellent effect and safety. In view of this, use of a ligand-type CAR has been proposed as an alternative to conventional antibody-type CARs (Non Patent Literature 2).

CITATION LIST

Non Patent Literature

Non Patent Literature 1: Yozo Nakazawa, "the Shinshu Medical Journal" 2013, Vol. 61, No. 4, p. 197-203

Non Patent Literature 2: Donald R. Shaffer et al., "Medical Sciences," 2014, Vol. 2, p. 22-36

SUMMARY OF INVENTION

Technical Problem

In the ligand-type CAR, the target binding domain is a ligand specifically binding to a receptor protein expressed on a target cell. Examples of the ligands include a cytokine, an affibody, a natural receptor-derived ligand-binding domain, a soluble protein/peptide ligand of a receptor (for example, on tumor cells), a peptide and a vaccine for facilitating an immune response. Accordingly, it is expected that the ligand-type CAR exerts the same target cytotoxic activity as in conventional CARs as long as a receptor is expressed on a target cell surface. In addition, when an endogenous protein is used as a ligand, reduction of undesirable immune responses as mentioned above can be expected.

However, ligand-type CARs are now under development and clinically effective ligand-type CARs have not yet been found.

Solution to Problem

The present inventors' group focused on the fact that a GM-CSF receptor is highly expressed on the surface of tumor cells such as juvenile myelomonocytic leukemia (JMML) cells, and considered that a ligand-type CAR using the open reading frame of wild-type GM-CSF as a target binding domain, that is, a GM-CSF receptor-specific chimeric antigen receptor (hereinafter referred to as a "GMR.GAR"), may be possibly used in an adoptive immunotherapy for the disease (leukemia), and further conducted studies. As a result, we have found that T cells into which a GMR.CAR gene was introduced (hereinafter referred to as a "GMR.CAR-T cell") exert cytotoxic activity against CD34+ tumor cells derived from JMML patient.

We have further found that the GMR.CAR-T cell itself secretes GM-CSF over time when killing tumor cells; and that since the elevation of GM-CSF secretion may serve as a factor of preventing improvement of cytotoxic activity of the GMR.CAR-T cells, this issue must be addressed in developing the GMR.CAR for therapy use. Accordingly, we examined further to provide a GMR.CAR that suppresses the expression of GM-CSF gene in a GMR.CAR-T cell and has improved cytotoxic activity.

As a result, we have found that GM-CSF secretion from GMR.CAR-T cells can be suppressed by expressing a polynucleotide encoding a GMR.CAR simultaneously with a polynucleotide that can induce an RNAi effect against GM-CSF, in a host cell, and that the cytotoxic activity of the GMR.CAR-T cells against a target cell can be improved. Based on the finding, the present invention was accomplished.

More specifically, the present invention is as follows.

[1] A genetically modified cell comprising, introduced thereinto, a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain.

[2] A genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and (ii) a polynucleotide that induces RNAi to human GM-CSF.

[3] The cell according to [1] or [2] above, wherein the cell expresses a CAR that binds to a GM-CSF receptor on a cell membrane thereof.

[4] The cell according to any one of [1] to [3] above, wherein the CAR protein further comprises a co-stimulatory domain and/or an extracellular spacer domain.

[5] The cell according to any one of [1] to [4] above, wherein the intracellular signaling domain is human CD3ζ.

[6] The cell according to [4] or [5] above, wherein the co-stimulatory domain is human CD28 or human 4-1BB.

[7] The cell according to any one of [4] to [6] above, wherein the extracellular spacer domain comprises a hinge, CH2 and/or CH3 region of human IgG1 or a part thereof and/or an artificial spacer sequence.

[8] The cell according to any one off [1] to [7] above, wherein the target binding domain is a polypeptide consisting of an amino acid sequence represented by SEQ ID NO: 2 or an amino acid sequence having a sequence identity of 90% or more with the amino acid sequence of SEQ ID NO: 2.

[9] The cell according to any one of [2] to [8] above, wherein the polynucleotide that induces RNAi is an siRNA or an shRNA.

[10] A method for producing a chimeric antigen receptor (CAR) protein expressing cell, comprising introducing a polynucleotide encoding a CAR protein that specifically binds to a human GM-CSF receptor into a cell using a vector.

[11] A method for producing a chimeric antigen receptor (CAR) protein expressing cell, comprising introducing a polynucleotide encoding a CAR protein that specifically binds to a human GM-CSF receptor and a polynucleotide that induces RNAi to human GM-CSF into a cell using the same vector or different vectors.

[12] A vector comprising a polynucleotide encoding a chimeric antigen receptor (CAR) protein that specifically binds to a human GM-CSF receptor.

[13] A vector comprising: a polynucleotide encoding a chimeric antigen receptor (CAR) protein that specifically binds to a human GM-CSF receptor; and a polynucleotide that induces RNAi to human GM-CSF.

[14] A kit for producing a chimeric antigen receptor (CAR) protein expressing cell, comprising: a vector comprising a polynucleotide encoding a CAR protein that specifically binds to a human GM-CSF receptor; and a vector comprising a polynucleotide that induces RNAi to human GM-CSF.

[15] A therapeutic agent for a disease involving GM-CSF receptor expressing cells, comprising a cell according to any one of [1] to [9] above.

[16] A pharmaceutical composition comprising the therapeutic agent according to [15] above and a pharmaceutically acceptable carrier.

The description of the present application incorporates the contents disclosed in JP Patent Application No. 2016-182293 based on which this application claims for priority.

Advantageous Effects of Invention

The GMR.CAR-T cell of the present invention is expected to have an effect on an adoptive immunotherapy targeting various cells expressing a GM-CSF receptor on the cell surface, such as juvenile myelomonocytic leukemia (JMML) cells and acute myelogenous leukemia (AML) cells. Also, the genetically modified cell of the present invention, in which a polynucleotide encoding a GMR.CAR and a polynucleotide that induces RNAi to GM-CSF are expressed simultaneously, suppresses GM-CSF secretion from the genetically modified cell over time and exerts an excellent cytotoxic activity to target cells.

BRIEF DESCRIPTION OF DRAWINGS

FIG. 15 shows the antitumor-cell activity (%) of CAR-T 001, CAR-T 004 to CAR-T 007 and Mock-T cells, into which no polynucleotide was introduced, against THP-1 cells (A) and the ability of these cells to kill tumor THP-1 cells (B).

FIG. 17 shows the antitumor-cell activity (%) of CAR-T 001, CAR-T 004 to CAR-T 007 and Mock-T cells against shinAML-1 cells (A) and the ability of these cells to kill tumor shinAML-1 cells (B).

FIG. 18 shows the antitumor-cell activity (%) of CAR-T 001, CAR-T 004 to CAR-T 007 and Mock-T cells against MV4-11 cells (A) and the ability of these cells to kill tumor MV4-11 cells (B).

FIG. 20 shows the time-dependent change of GM-CSF concentration in the supernatant of the co-culture of any one of CAR-T 001, CAR-T 004 to CAR-T 007 and Mock-T cells, and shinAML-1 (A) or MV4-11 cells (B).

FIG. 30 shows the number of tumor cells in a well and E to T ratio combination in evaluation of the antitumor-cell activity persistence of CAR-T 001, CAR-T 008 to CAR-T 011 and Mock-T cells against THP-1 cells.

FIG. 31 shows the number of tumor cells in a well and E to T ratio combination in evaluation of the antitumor-cell activity persistence of CAR-T 001, CAR-T 008 to CAR-T 011 and Mock-T cells against MV4-11 cells.

FIG. 36 shows the number of tumor cells in a well and E to T ratio combination in evaluation of the antitumor-cells activity persistence of CAR-T 008, 010, 012, 014 and Mock-T cells against THP-1 cells.

FIG. 37 shows the number of tumor cells in a well and E to T ratio combination in evaluation of the antitumor-cell activity persistence of CAR-T 008, 010, 012, 014 and Mock-T cells against MV4-11 cells.

DESCRIPTION OF EMBODIMENTS

Figure 1:
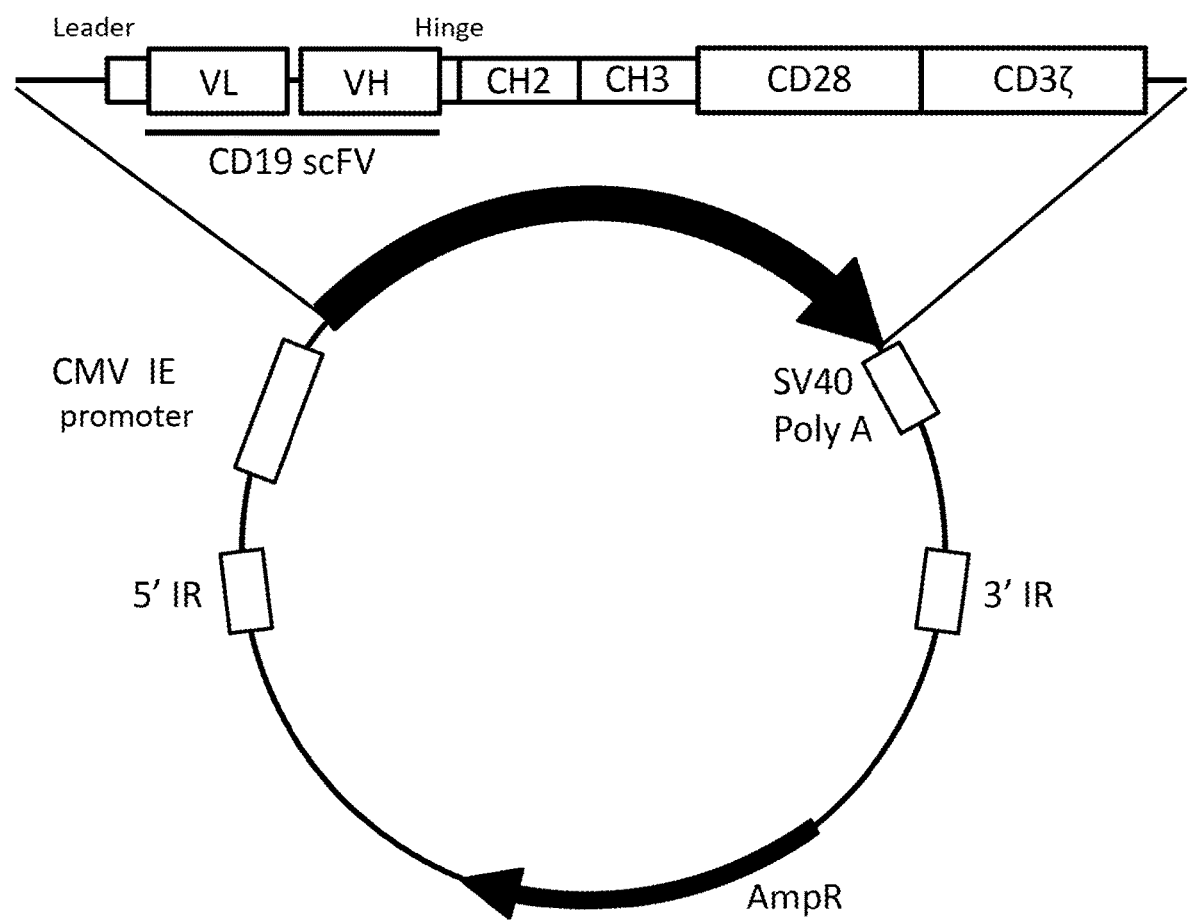
FIG. 1 shows an example of a vector map of a CD19.CAR.

Embodiments of the present invention will be more specifically described below.

As used herein, the "chimeric antigen receptor (CAR)" refers to a modified receptor, which can confer its target specificity to cells such as T cells (for example, naive T cells, central memory T cells, effector memory T cells or a combination thereof). The CAR is also known as an artificial T cell receptor, a chimeric T cell receptor or a chimeric immunoreceptor.

As used herein, the "domain" refers to a region within a polypeptide and folded in the form of a specific structure, independently of other regions.

"RNAi" (RNA interference) generally refers to a mechanism where a double-stranded RNA (dsRNA), which consists of a strand having a sequence homologous to mRNA of a target gene and a strand having a complementary sequence thereof, is introduced into, e.g., a cell to induce decomposition of the mRNA of the target gene, thereby suppressing the expression of the target gene. RNAi is a process of sequence-specific post-transcriptional gene suppression. In RNAi to mammalian cells, a short double-stranded RNA (siRNA) having a sequence corresponding to the target mRNA sequence is used.

As used herein, the "polynucleotide that induces RNAi" refers to a polynucleotide, which produces a desired siRNA (siRNA causing RNAi to a target gene) by intracellular processing upon introduction into a cell and, an shRNA (short hairpin RNA) can be used, for example. The shRNA has a structure in which a sense RNA and an antisense RNA are connected via a loop structure portion (hairpin structure). The cleavage of the loop structure portion within a cell results in a double-stranded siRNA and produces the RNAi effect. As used herein, the "polynucleotide that induces RNAi" may include an antisense RNA and a ribozyme.

The "polynucleotide" as used herein include, but are not limited to, a natural or synthetic DNA and RNA, for example, genomic DNA, cDNA (complementary DNA), mRNA (messenger RNA), rRNA (ribosome RNA), shRNA (small hairpin RNA, snRNA (small nuclear RNA, snoRNA (small nucleolar RNA), miRNA (micro RNA) and/or tRNA.

As used herein, the "coding region" refers to a region to be translated into a protein in mRNA region (coding region); whereas the "untranslated region" refers to a region positioned at both sides of the coding region and not to be translated into a protein. As the untranslated region, a 5'-untranslated region (5'-UTR) at the 5' terminal side and a 3'-untranslated region (3'-UTR) at the 3' terminal side are present. More specifically, in the sequence disclosed under SEQ ID NO: 1, which contains nucleotide sequences of 5'- and 3'-untranslated regions and a coding region of human GM-CSF, a polynucleotide at positions 1 to 32 corresponds to 5'-UTR, a polynucleotide at positions 33 to 467 corresponds to a coding region, and a polynucleotide at positions 468 to 800 corresponds to 3'-UTR.

As used herein, the term "encode (encodes, encoding)" means that a predetermined nucleotide sequence has a code for information of the amino acid sequence of a predetermined protein or (poly)peptide, as ordinarily used in the art, and both a sense strand and an antisense strand are used herein in the context of "encoding".

As described above, the present invention provides a genetically modified cell comprising, introduced thereinto, a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain.

The CAR protein of the present invention comprises a "target binding domain" that specifically binds to a human GM-CSF receptor. The target (GM-CSF receptor) binding domain shows a binding ability specific to the GM-CSF receptor, and can cause an immune response specific to target cells expressing the GM-CSF receptor on the cell surface.

Accordingly, a polypeptide having the amino acid sequence of GM-CSF, a cytokine that binds to a GM-CSF receptor, can be used as a GM-CSF receptor binding domain. As a preferable embodiment of the GM-CSF receptor binding domain, a polypeptide consisting of the amino acid sequence encoded by the open reading frame of human GM-CSF can be used. More specifically, GM-CSF protein comprising the amino acid sequence of SEQ ID NO: 2 can be used. Alternatively, a polypeptide consisting of an amino acid sequence having a sequence identity of 90% or more with the amino acid sequence of SEQ ID NO: 2 and having a binding ability to a human GM-CSF receptor can be used. For example, a polypeptide consisting of the amino acid sequence of SEQ ID NO: 4 can also be used. Furthermore, as long as a binding ability to a GM-CSF receptor is retained, fragments of these polypeptides, in other words, binding fragments can be used.

The phrase "having a binding ability to a human GM-CSF receptor" means that the association constant to a human GM-CSF receptor is, for example, 1 to 1000 nM or less. The binding ability may be relatively weak compared to an antigen-antibody binding ability.

The CAR protein herein may optionally comprise an "extracellular spacer domain". The extracellular spacer domain is desirably a sequence promoting CAR-antigen binding to facilitate signal transmission into a cell. For example, an Fc fragment of an antibody or a fragment or derivative thereof, a hinge region of an antibody or a fragment or derivative thereof, a CH2 region of an antibody, a CH3 region of an antibody, an artificial spacer sequence or a combination thereof can be used.

In an aspect of the present invention, as the extracellular spacer domain, (i) a hinge, CH2 and CH3 regions of IgG4, (ii) a hinge region of IgG4, (iii) a hinge and CH2 of IgG4, (iv) a hinge region of CD8a, (v) a hinge, CH2 and CH3 regions of IgG1, (vi) a hinge region of IgG1 or (vii) a hinge and CH2 of IgG1, or a combination thereof can be used. For example, as the hinge region of IgG1, the following region having the amino acid sequence (SEQ ID NO: 6) encoded by the nucleotide sequence represented by SEQ ID NO: 5 can be suitably used; however, the hinge region is not limited thereto.

UniProt No.: P01857 (99-110)
EPKSCDKTHTCP PCDPA EPKSPDKTHTCP
  hinge    spacer    hinge As the CH2 region of IgG1, the region having the amino acid sequence (SEQ ID NO: 8) encoded by the nucleotide sequence represented by SEQ ID NO: 7 can be suitably used. As the CH3 region, the region having the amino acid sequence (SEQ ID NO: 10) encoded by the nucleotide sequence represented by SEQ ID NO: 9 can be suitably used; however, the CH2 and CH3 regions are not limited thereto.

As a preferable aspect, human IgG1 hinge, CH2 and CH3 regions or a part thereof can be used as the extracellular spacer domain.

As a further preferable aspect, (i) human IgG1 hinge region alone (SEQ ID NO: 6) alone, (ii) a combination of human IgG1 hinge region (SEQ ID NO: 6) and CH3 region (SEQ ID NO: 10) and/or (iii) CH3 region alone (SEQ ID NO: 10) can be used as the extracellular spacer domain.

As one aspect of the present invention, as the artificial spacer sequence to be used as the extracellular spacer domain, a spacer sequence represented by the formula (G4S)n can be used. In the formula, n represents an integer of 1 to 10 and preferably, n=3. For example, the spacer sequence represented by SEQ ID NO: 42 can be suitably used. The spacer having such a spacer sequence is sometimes referred to as a peptide linker. Peptide linkers suitably used in the art can be appropriately used in the present invention. In this case, the constitution and chain length of the peptide linker can be properly selected as long as the function of the CAR protein to be obtained is not impaired.

As a further preferable aspect, a combination of human IgG1 hinge region (SEQ ID NO: 6) and a spacer sequence (SEQ ID NO: 42) represented by (G4S)3 can be used as the extracellular spacer domain.

The extracellular spacer domain can be appropriately selected from the above examples or further modified based on common technics knowledge in the art to be used for the present invention.

Nucleotide sequences encoding the respective amino acid sequences of domains are ligated and inserted into a vector and expressed in a host cell, such that the extracellular spacer domain can exist between the target binding domain and the transmembrane domain. Alternatively, the extracellular spacer domain can be modified using a polynucleotide encoding a plasmid CAR protein previously produced as a template.

Modification of the extracellular spacer domain is useful when considering, for example, improvement of a CAR gene expression rate in a CAR-T cell having a polynucleotide encoding a CAR introduced thereinto, signal transmission, aging of a cell, distribution in a tumor, antigen recognition or influence on in vivo activity.

The CAR protein of the present invention comprises: an extracellular domain present on the cell membrane including a target binding domain and optionally an extracellular spacer domain; a transmembrane domain; and an intracellular domain including an intracellular signaling domain and optionally a co-stimulatory domain. As well known in the art, the "transmembrane domain" is a domain having an affinity to a lipid bilayer constituting cell membrane; whereas the extracellular domain and intracellular domain are both hydrophilic domains. The transmembrane domain in the GMR.CAR of the present invention is not particularly limited as long as the CAR protein can be present on the cell membrane, and the target binding domain and the intracellular signaling domain are not functionally impaired; a polypeptide derived from the same protein as that of a co-stimulatory domain, which is described later, may play a role as a transmembrane domain.

In an aspect of the present invention, a transmembrane domain such as CD28, CD3ε, CD8α, CD3, CD4 or 4-1BB can be used as the transmembrane domain.

As a preferable aspect, human CD28 (Uniprot No.: P10747 (153-179)) can be used as the transmembrane domain. More specifically, human CD28 having the amino acid sequence (SEQ ID NO: 12) encoded by the nucleotide sequence represented by SEQ ID NO: 11 (NCBI) Accession No.: NM_006139.3 (679-759)) can be suitably used as the transmembrane domain.

The CAR protein of the present invention may optionally comprise a "co-stimulatory domain". The co-stimulatory domain specifically binds to a co-stimulation ligand, thereby mediating cellular co-stimulation responses such as growth of CAR-T cells, cytokine production, functional differentiation and target cell death, but the cellular co-stimulation responses are not limited thereto).

In an aspect of the present invention, the co-stimulatory domain that can be used include, for example, CD27, CD28, 4-1BB (CD137), CD134 (OX40), Dap10, CD2, CD5, CD30, CD40, PD-1, ICAM-1, LFA-1 (CD11a/CD18), TNFR-I, TNFR-II, Fas and Lck.

In a preferable aspect, e.g., human VD28 (Uniprot NO.: P10747 (180-220)) or 4-1BB (GenBank: U03397.1) can be used as the co-stimulatory domain. More specifically, those having the amino acid sequence (SEQ ID NO: 14) encoded by the nucleotide sequence represented by SEQ ID NO: 13 (NCBI Accession No.: NM_006139.3 (760-882) can be suitably used as the co-stimulatory domain.

The CAR protein of the present invention comprises an "intracellular signaling domain." The intracellular signaling domain transmits a signal required for the effector function of immune cells.

In an aspect of the present invention, as the intracellular signaling domain, for example, a human VD3ζ chain, FcγRIII, FcεRI, a cytoplasmic end of an Fc receptor, a cytoplasmic receptor having an immunoreceptor tyrosine activation motif (ITAM) or a combination thereof can be used.

In a preferable aspect of the intracellular signaling domain, a human CD3ζ chain (for example, nucleotides 299-637 of NCBI Accession No. NM_000734.3) can be used. More specifically, a human CD3ζ chain having the amino acid sequence (SEQ ID NO: 16) encoded by the nucleotide sequence represented by SEQ ID NO: 15 can be suitably used as the intracellular signaling domain.

The polynucleotide of interest can be easily produced in accordance with a routine method. The nucleotide sequences encoding the amino acid sequences of individual domains can be obtained form the NCBI RefSeq ID and GenBank Accession numbers. The polynucleotide of the present invention can be produced in accordance with standard molecular biological and/or chemical procedures. For example, nucleic acids can be synthesized based on these nucleotide sequences. Also, DNA fragments obtained through the polymerase chain reaction (PCR) from a cDNA library can be combined to produce the polynucleotide of the present invention.

Accordingly, the polynucleotide encoding a GMR.CAR of the present invention can be produced by ligating polynucleotides encoding aforementioned respective domains, and a GMR.CAR-T cell can be produced by introducing the polynucleotide thus constructed into a proper cell. Alternatively, the GMR.CAR can be produced by using a polynucleotide encoding a known CAR protein having the same structural components except a target binding domain, as a template, and recombining the target binding domain in accordance with a routine method.

Furthermore, depending on the purpose, one or more domains, for example, an extracellular spacer domain of a polynucleotide encoding a known CAR protein used as a template, can be modified by, e.g., an inverse-PCR (iPCR) method. The technique for modifying an extracellular spacer domain is described, for example, in Oncoimmunology, 2016, Vol. 5, No. 12, e1253656.

The present invention also provides a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and (ii) a polynucleotide that induces RNAi to human GM-CSF.

The polynucleotide that induces RNAi to human GM-CSF according to the present invention is a nucleic acid molecule that suppresses an expression process (including transcription, post-transcriptional regulation, translation, post-translational regulation) of GM-CSF gene. The "suppression of expression" according to the present invention may be transient suppression or permanent suppression.

To cause target-specific RNAi, an siRNA, which consists of a sense strand having complementarity to a part of mRNA sequence of a target gene and an antisense strand complementary to the sense strand, may be introduced into a cell or expressed within a cell. According to an embodiment of the present invention, an siRNA or an shRNA can be used as the polynucleotide that induces RNAi. The siRNA is a short-chain double-stranded RNA molecule and usually consists of 15 to 30 base pairs. The shRNA is a hairpin-type RNA, which can be processed in vivo by a dicer to produce an siRNA. The siRNA and shRNA can be introduced into a cell in vitro or in vivo with a transfection reagent such as lipofectamine. Alternatively, the siRNA and shRNA each may be integrated into a vector in the form of DNA such that they can be expressed in a cell and introduced into the cell.

The siRNA targeting GM-CSF gene is usually a double-stranded RNA, which is formed by hybridizing a sense strand consisting of a sequence homologous to a continuous region of the mRNA sequence of the gene and an antisense strand consisting of a complementary sequence of the sense strand. The "continuous region" herein has a length usually corresponding to 15 to 30 nucleotides. The "continuous region" may comprise a coding region and an untranslated region of GM-CSF gene, and a boundary between the coding region and the untranslated region. Although it is not particularly limited, the siRNA and shRNA which can be suitably used in the present invention are those targeting an untranslated region of mRNA of human GM-CSF gene.

The siRNA and shRNA can be easily designed and prepared by those skilled in the art based on, e.g., information of a target sequence. In designing an siRNA, a sequence (continuous sequence) unique to the target sequence is ordinarily used. Programs and algorithms for selecting an appropriate target sequence have been developed. Alternatively, as an siRNA and an shRNA for suppressing or inhibiting the expression of a certain target protein, commercially available siRNA and shRNA products can be obtained from suppliers such as Takara Bio Inc., Thermo Fisher Scientific K.K. and QIAGEN K.K.

Accordingly, although not particularly limited, examples of the polynucleotide that induces RNAi to human GM-CSF used in Examples by the present inventors include siRNAs having the sequences represented by SEQ ID NOs: 20 and 21, 23 and 24, and 26 and 27, and shRNAs having the nucleotide sequences represented by SEQ ID NOs: 22, 25 and 28.

Another aspect of the polynucleotide that induces RNAi is a vector that can express desired siRNA. Examples of the vector include a vector expressing an shRNA to be converted into siRNAs by later processing (called as stem-loop or short hairpin-type); and a vector separately expressing a sense RNA and an antisense RNA (called as tandem type). These vectors can be produced in accordance with routine methods by those skilled in the art.

In order to permanently suppress the expression of GM-CSF in a host cell, a vector expressing an shRNA within a cell as the polynucleotide that induces RNAi is preferably used.

The polynucleotide that induces RNAi of the present invention is expressed in a host cell simultaneously with a GMR.CAR having human GM-CSF as a target binding domain. Accordingly, the polynucleotide that induces RNAi of the present invention desirably suppresses expression of GM-CSF in a host cell without affecting the expression of the GMR.CAR in the host cell.

In view of the above feature, in one embodiment of the present invention, a nucleotide sequence consisting of 15 to 30 nucleotides, which has a nucleotide sequence consisting of 15 to 30 nucleotides having complementarity to any continuous region consisting of 15 to 30 nucleotides in the mRNA sequence of an untranslated region of GM-CSF, as a sense strand, and contains a nucleotide sequence complementary to the sense strand as antisense strand, can be used as an siRNA. As the untranslated region of GM-CSF, the untranslated region at the 5'-terminal side and the untranslated region at the 3'-terminal side are present, and either one of the untranslated regions may be used. More specifically, as the untranslated region of the 5'-terminal side, any region of 15 to 30 continuous nucleotides of the sequence at positions 1 to 32 in the full-length nucleotide sequence of human GM-CSF represented by SEQ ID NO: 1 can be selected. As the untranslated region of the 3'-terminal side, any region consisting of 15 to 30 continuous nucleotides of the sequence at positions 468 to 800 in the full-length nucleotide sequence of human GM-CSF represented by SEQ ID NO: 1 can be selected. More preferably, the untranslated region of the 5'-terminal side can be used.

In a further embodiment of the present invention, for example, siRNAs having the sequences represented by SEQ ID NOs: 20 and 21 can be used as a polynucleotide that induces RNAi.

In a further embodiment of the present invention, an shRNA having the sequence represented by SEQ ID NO: 22 can be used.

In the present invention, a polynucleotide encoding a chimeric antigen receptor protein that specifically binds to a human GM-CSF receptor and a polynucleotide that induces RNAi to human GM-CSF can be present in the same vector under control of a promoter suitable for expression in human cells, and may be present in different vectors. As an appropriate promoter, both of a constitutive promoter and an inducible promoter may be used. Preferable promoters may be derived from CMV and SV-40. When the polynucleotides are separately introduced by different vectors, a host cell can be transfected with these vectors simultaneously or consecutively.

In one embodiment of the present invention, it is possible to use a genetically modified cell comprising, introduced thereinto,
a polynucleotide encoding a chimeric antigen receptor (CAR) protein having a target binding domain that specifically binds to a human granulocyte-macrophage colony stimulating factor (GM-CSF) receptor comprising the amino acid sequence of SEQ ID NO: 1, a transmembrane domain comprising the amino acid sequence of SEQ ID NO: 12, and an intracellular signaling domain comprising the amino acid sequence of SEQ ID NO: 16.

In one embodiment of the present invention, it is possible to use a genetically modified cell comprising, introduced thereinto,
a polynucleotide encoding a chimeric antigen receptor (CAR) protein having a target binding domain that specifically binds to a human granulocyte-macrophage colony stimulating factor (GM-CSF) receptor comprising the amino acid sequence of SEQ ID NO: 1, an extracellular spacer domain comprising the amino acid sequences of SEQ ID NO: 6, SEQ ID NO: 8, SEQ ID NO: 10 and/or SEQ ID NO: 42, a transmembrane domain comprising the amino acid sequence of SEQ ID NO: 12, and an intracellular signaling domain comprising the amino acid sequence of SEQ ID NO: 16.

The phrase "comprising the amino acid sequences of SEQ ID NO: 6, SEQ ID NO: 8, SEQ ID NO: 10 and/or SEQ ID NO: 42" means that the domain comprises any one or any combination of two or more of the amino acid sequences of SEQ ID NO: 6, SEQ ID NO: 8, SEQ ID NO: 10 and SEQ ID NO: 42. The same applies hereinbelow.

In one embodiment of the present invention, it is possible to use a genetically modified cell comprising, introduced thereinto:
(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and
(ii) siRNA or shRNA having complementarity to the sequence of an untranslated region of the human GM-CSF, as a polynucleotide that induces RNAi to human GM-CSF.

In one embodiment of the present invention, it is possible to use a genetically modified cell comprising, introduced thereinto:
(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and
(ii) a polynucleotide that induces RNAi to human GM-CSF of SEQ ID NO: 22, SEQ ID NO: 25 or SEQ ID NO: 28.

In one embodiment of the present invention, it is possible to use a genetically modified cell comprising, introduced thereinto:
(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and (ii) siRNA or shRNA having complementarity to the sequence of the 5'-side untranslated region of human GM-CSF, as a polynucleotide that induces RNAi to human GM-CSF.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain and an intracellular signaling domain; and (ii) a polynucleotide that induces RNAi to human GM-CSF of SEQ ID NO: 22 or SEQ ID NO: 25.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequences of SEQ ID NO: 6, SEQ ID NO: 8, SEQ ID NO: 10 and/or SEQ ID NO: 42, a co-stimulatory domain comprising the amino acid sequence of SEQ ID NO: 14, and an intracellular signaling domain comprising the amino acid sequence of SEQ ID NO: 16; and (ii) siRNA or shRNA having complementarity to the sequence of the untranslated region of human GM-CSF, as a polynucleotide that induces RNAi to human GM-CSF.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, a co-stimulatory domain comprising the amino acid sequence of SEQ ID NO: 14, and an intracellular signaling domain comprising the amino acid sequence of SEQ ID NO: 16; and (ii) siRNA or shRNA having complementarity to the sequence of the untranslated region of human GM-CSF, as a polynucleotide that induces RNAi to human GM-CSF.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, SEQ ID NO: 8, SEQ ID NO: 10 and or SEQ ID NO: 42, a co-stimulatory domain comprising the amino acid sequence of SEQ ID NO: 14, and an intracellular signaling domain comprising the amino acid sequence of SEQ ID NO: 16; and (ii) a polynucleotide that induces RNAi to human GM-CSF of SEQ ID NO: 22, SEQ ID NO: 25 or SEQ ID NO: 28.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, a co-stimulatory domain comprising the amino acid sequence of SEQ ID NO: 14, and an intracellular signaling domain comprising the amino acid sequence of SEQ ID NO: 16; and (ii) a polynucleotide that induces RNAi to human GM-CSF of SEQ ID NO: 22, SEQ ID NO: 25 or SEQ ID NO: 28.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, SEQ ID NO: 8, SEQ ID NO: 10 and or SEQ ID NO: 42, a co-stimulatory domain comprising the amino acid sequence of SEQ ID NO: 14, and an intracellular signaling domain comprising the amino acid sequence of SEQ ID NO: 16; and (ii) siRNA or shRNA having complementarity to the sequence of the 5' side untranslated region of human GM-CSF, as a polynucleotide that induces RNAi to human GM-CSF.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, a co-stimulatory domain comprising the amino acid sequence of SEQ ID NO 14, and an intracellular signaling domain comprising the amino acid sequence of SEQ ID NO: 16; and (ii) siRNA or shRNA having complementarity to the sequence of the 5' side untranslated region of the human GM-CSF, as a polynucleotide that induces RNAi to human GM-CSF.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, SEQ ID NO: 8, SEQ ID NO: 10 and/or SEQ ID NO: 42, a co-stimulatory domain comprising the amino acid sequence of SEQ ID NO: 14, and an intracellular signaling domain comprising the amino acid sequence of SEQ ID NO: 16; and (ii) a polynucleotide that induces RNAi to human GM-CSF of SEQ ID NO: 22 or SEQ ID NO: 25.

In one embodiment of the present invention, it is possible to use a genetically modified cell comprising, introduced thereinto:

(i) a polynucleotide encoding a chimeric antigen receptor (CAR) protein having a target binding domain that specifically binds to a human granulocyte-macrophage colony stimulating factor (GM-CSF) receptor, a transmembrane domain, an extracellular spacer domain comprising the amino acid sequence of SEQ ID NO: 6, a co-stimulatory domain comprising the amino acid sequence of SEQ ID NO:

14, and an intracellular signaling domain comprising the amino acid sequence of SEQ ID NO: 16; and (ii) a polynucleotide that induces RNAi to human GM-CSF of SEQ ID NO: 22 or SEQ ID NO: 25.

As the cell into which the above polynucleotides are to be introduced, cells derived from mammals such as human or T cells derived from a non-human mammal, such as monkey, mouse, rat, pie, cow and dog, or a cell population containing the T cells can be used; for example, cells taken, isolated, purified or induced from blood (e.g., peripheral blood, umbilical cord blood), a body fluid such as bone marrow, a tissue or an organ can be used. Peripheral blood mononuclear cells (PBMCs), immune cells [dendritic cells, B cells, hematopoietic stem cells, macrophages, monocytes, NK cells or hemocyte cells (neutrophils, basophils)], umbilical blood mononuclear cells, fibroblasts, preadipocytes, stem cells, skin keratinocytes, mesenchymal cells, fatty liver cells, various cancer cell lines or neural stem cells can be used.

In a preferable embodiment of the present invention, for example, cells releasing a cytotoxic protein (e.g., perforin, granzyme) can be used. More specifically, for example, T cells, precursor T cells (e.g., hematopoietic stem cells, lymphocyte precursor cells), NK cells, NK-T cells or a cell population containing these cells can be used. Further, cells capable of differentiating into these cells include various stem cells such as ES cells and iPS cells T cells include CD8-positive T cells, CD4-positive T cells, regulatory T cells, cytotoxic T cells or tumor-infiltrating lymphocytes. The cell population containing T cells and precursor T cells includes PBMC. The above cells may be taken from a living body, and cells obtained by subjecting the cells to expansion culture or established as a cell strain from the cells may be used. When the cells expressing the produced CAR or cells differentiated from the cells are transplanted into a living body, it is desirable to introduce a nucleic acid into cells taken from the living body or a living body of the same species.

A method for introducing a polynucleotide for use in production of a genetically modified cell is not particularly limited as long as it is ordinarily used. In the case where a polynucleotide is introduced using a vector, examples of the vector that can be used include, but are not particularly limited to, a lentiviral vector, a retroviral vector, a foamy virus vector and an adeno-associated virus vector. As an aspect of a non-viral vector, a plasmid transposon can be used. A sleeping beauty transposon system (for example, described in Huang X, Guo H, et al Mol Ther. 2008; 16: 580-9; Singh H, Manuri P R, et al. Cancer Res. 2008; 68: 2961-71; Deniger D C, Yu J, et al. PLoS One, 2015; 10: e0128151; Singh H. Moyes J S, et al. Cancer Gene Ther. 2015: 22: 95-100; Hou X, Du Y, et al Cancer Biol Ther. 2015; 16: 8-16; Singh H, Huls H, et al Immunol Rev. 2014; 257: 181-90; and Maiti S N, Huls H, et al. J Immunother. 2013; 36: 112-23) or a piggybac transposon system (described in Nakazawa Y, Huye L E, et al. J Immunother. 2009: 32: 826-36; Galvan D L, Nakazawa Y. et al. J Immunother. 2009; 32: 837-44; Nakazawa Y, Huye L E, et al. Mol Ther. 2011; 19: 2133-43; Huye L E, Nakazawa Y, et al. Mol Ther. 2011; 19. 2239-48; Saha S. Nakazawa Y, et al. J Vis Exp. 2012; (69): e4235; Nakazawa Y, Saha S, et al. J Immunother. 2013; 36:3-10; and Saito S, Nakazawa Y, et al. Cytotherapy. 2014; 16: 1257-69) can be suitably used.

In a preferable aspect of the present invention, a non-viral vector, in particular, a piggybac transposon system can be used. Specific examples will be described in Examples.

The present invention also provides, as mentioned above, a method for producing a chimeric antigen receptor (CAR) protein expressing cell, comprising introducing a polynucleotide encoding a CAR protein that specifically binds to a human GM-CSF receptor into a cell using a vector.

As mentioned above, the present invention also provides, a method for producing a chimeric antigen receptor (CAR) protein expressing cell, comprising introducing a polynucleotide encoding a CAR protein that specifically binds to a human GM-CSF receptor and a polynucleotide that induces RNAi to human GM-CSF into a cell using the same vector or different vectors.

In a preferable embodiment of the present invention, the polynucleotide encoding a GMR.CAR and the polynucleotide that induces RNAi are desirably integrated into the same vector in order to enhance the simultaneous expression of the two polynucleotides in the host cell. In other words, it is desirable that the GMR.CAR is allowed to express in a host cell where the expression of GM-CSF is suppressed by the polynucleotide that induces RNAi. For example, a genetically modified cell can be produced using a polynucleotide at positions 33 to 467 in SEQ ID NO: 1 and a polynucleotide having any of the nucleotide sequences represented by SEQ ID NOs: 29 to 31.

A vector comprising the polynucleotide encoding a GMR.CAR of the present invention and optionally a polynucleotide that induces RNAi is not particularly limited; for example, it can be produced and maintained in an appropriate host cell such as *Escherichia coli*.

The genetically modified cell of the present invention can be produced and cultured in a medium and under culture conditions suitable for culturing T cells or a cell population comprising T cells or precursor T cells, based on the description of the present application and common technical knowledge in the art. When culturing, a proper cytokine, such as IL-15 and IL-7 can be added.

As described also in Examples, in culturing a genetically modified cell of the present invention, an activated T cell stimulated with an antibody, or a vital peptide-added/activated T cell stimulated with an antibody and then treated with a viral peptide antigen, may be added as a feeder cell, as disclosed, for example, in International Publication No. WO 2017/1161615. However, a method for culturing a genetically modified cell of the present invention is not particularly limited.

The cell of the present invention is activated by causing a receptor-specific immune response to a target cell expressing a GM-CSF receptor on the surface, thereby transmitting a signal into the cell. Activation of a cell expressing a CAR varies depending on the type of host cell and the intracellular domain of the CAR. Activation of the cell can be confirmed based on, for example, release of a cytokine, cell growth-rate improvement and/or a change of a cell-surface molecule as an index(es). The release of a cytotoxic protein (e.g., perforin, granzyme) destroys a cell expressing a receptor.

The present invention further provides a vector comprising a polynucleotide encoding a chimeric antigen receptor (CAR) protein that specifically binds to a human GM-CSF receptor. The present invention further provides a vector comprising: a polynucleotide encoding a chimeric antigen receptor (CAR) protein that specifically binds to a human GM-CSF receptor; and a polynucleotide that induces RNAi to human GM-CSF. The present invention further provides a kit for producing a chimeric antigen receptor (CAR) protein expressing cell, comprising a vector comprising: a polynucleotide encoding a CAR protein that specifically binds to a human GM-CSF receptor; and a vector comprising a polynucleotide that induces RNAi to human GM-CSF.

The vector and the kit of the present invention can be suitably used for producing the genetically modified cell of the present invention.

The expressing a GMR.CAR of the present invention can be used as a therapeutic agent for a disease. Accordingly, the present invention provides a therapeutic agent for a disease involving a GM-CSF receptor expressing cell, comprising the cell of the present invention. The therapeutic agent comprises a cell expressing a CAR protein as an active ingredient and may further comprise an appropriate excipient. The disease that is expectedly treated with the therapeutic agent of the present invention is not limited as long as it exhibits sensitivity to the cell; examples thereof include a disease involving a cell expressing, particularly highly expressing a GM-CSF receptor, such as a blood cancer (leukemia). Specific examples thereof include juvenile myelomonocytic leukemia (JMML) and acute myelogenous leukemia (AML). Further, examples thereof include a solid cancer. Specific examples thereof include glioma, neuroblastoma, glioblastoma, brain tumor, colorectal adenocarcinoma, a prostate cancer, a kidney cancer, melanoma and a small cell lung cancer.

The case of applying the above therapeutic agent to a solid cancer includes a disease, such as a case where a GM-CSF receptor expresses in a cell forming a microenvironment for target cells, for example, bone marrow-derived immunosuppressive cells (MDSCs). Such a disease, even if a GM-CSF receptor is not expressed in a target cell, the therapeutic agent can be used in combination with another therapeutic agent, in order to enhance, for example, tumor cytotoxic activity.

The phrase "expressing, particularly highly expressing GM-CSF receptor" herein may refer to a case where expression intensity is high (for example, median fluorescence intensity (MFI) determined by flow cytometry is high) or a case where the expression rate (positive rate) is high. The case where the expression rate in a cell is high refers to, for example, a cell having an expression rate (positive rate) of CD33/CD116 of 40% or more, and preferably, 80% or more.

An aspect of the therapeutic agent of the present invention is an anticancer drug against tumor cells expressing a GM-CSF receptor. The therapeutic agent or anticancer drug of the present invention can be used alone or in combination with an agent and or a therapy having different action mechanism.

Accordingly, the therapeutic agent of the present invention can be formulated alone or in combination with other active ingredients into a pharmaceutical composition. The therapeutic agent or the pharmaceutical composition of the present invention can be topically or systemically administered. Although the dosage form is not limited, intravenous administration is preferable for treating leukemia, for example. The pharmaceutical composition may comprise, other than the therapeutic agent of the present invention and other active ingredients, a carrier, an excipient, a buffer and a stabilizer which are ordinarily used in the art, depending on the dosage form. The dose of the therapeutic agent of the present invention varies depending on the body weight and age of the patient, and the severity of the disease, and is not particularly limited. For example, the dose falls within the range of $10^4$ to $10^{10}$ CAR-positive cells/body weight (kg) and can be administered once to several times per day, every 2 days, every 3 days, weekly, every 2 weeks, monthly, every 2 months or every 3 months.

EXAMPLES

The present invention is more specifically described by way of Examples below; however, the present invention is not limited to the following Examples.

Example 1 Production of GMR.CAR Expression Plasmid (CAR 001)

A PGR product, which was prepared by adding an EcoRI site and a BclI site to both ends of human GM-CSF (coding region of NCBI Accession No.: NM_000758 (SEQ ID NO: 1, 33 to 464 nucleotides: prior to stop codon)), was subcloned to a pTA2 cloning vector (TOYOBO). The pTA2 cloning vector to which the human GM-CSF sequence was subcloned was double-digested with EcoRI and BclI to cleave the human GM-CSF sequence. Separately, a pSL1190 vector (Amersham) was double-digested with EcoRI and BamHI. The human GM-CSF sequence cleaved above was then ligated to the pSL1190 vector using compatible sites (pSL1190-GMR.CAR). Subsequently, the pSL1190-GMR.CAR was double-digested with NotI and EcoRI to cleave a GMR.CAR sequence portion.

Then, to obtain a transposon plasmid from pIRES2-eGFP (Ciomech), a 5' side inverse iteration sequence and a 3' side inverse iteration sequence were insetted to obtain a transposon plasmid, i.e., pIR-eGFP vector. Then, a puromycin resistance gene was removed from the pIR-eGFP vector to obtain a pIRII-eGFP vector. The SFG-CD19 CAR retroviral vector produced in Baylor College of Medicine was double-digested with EcoRI and NotI to obtain an anti-CD19 scFv (FMC63; Zola H. et al. Immunol Cell Biol. 1991 December; 69 (Pt 6): 411-22)-CD28-CD3ζ fragment. The pIRII-eGFP vector was also double-digested with EcoRI and NotI and ligated with the anti-CD19 scFv (FMC63)-CD28-CD3ζ to produce a pIRII-CD19.CAR. After the resultant pIRII-CD19.CAR (Mol Ther. 2011; 19: 2239-48 and Cytotherapy. 2014; 16: 1257-69) was double-digested with NotI and EcoRI, the GMR.CAR sequence cleaved above was Heated thereto to obtain a GMR.CAR expression plasmid (CAR 001).

Figure 2:
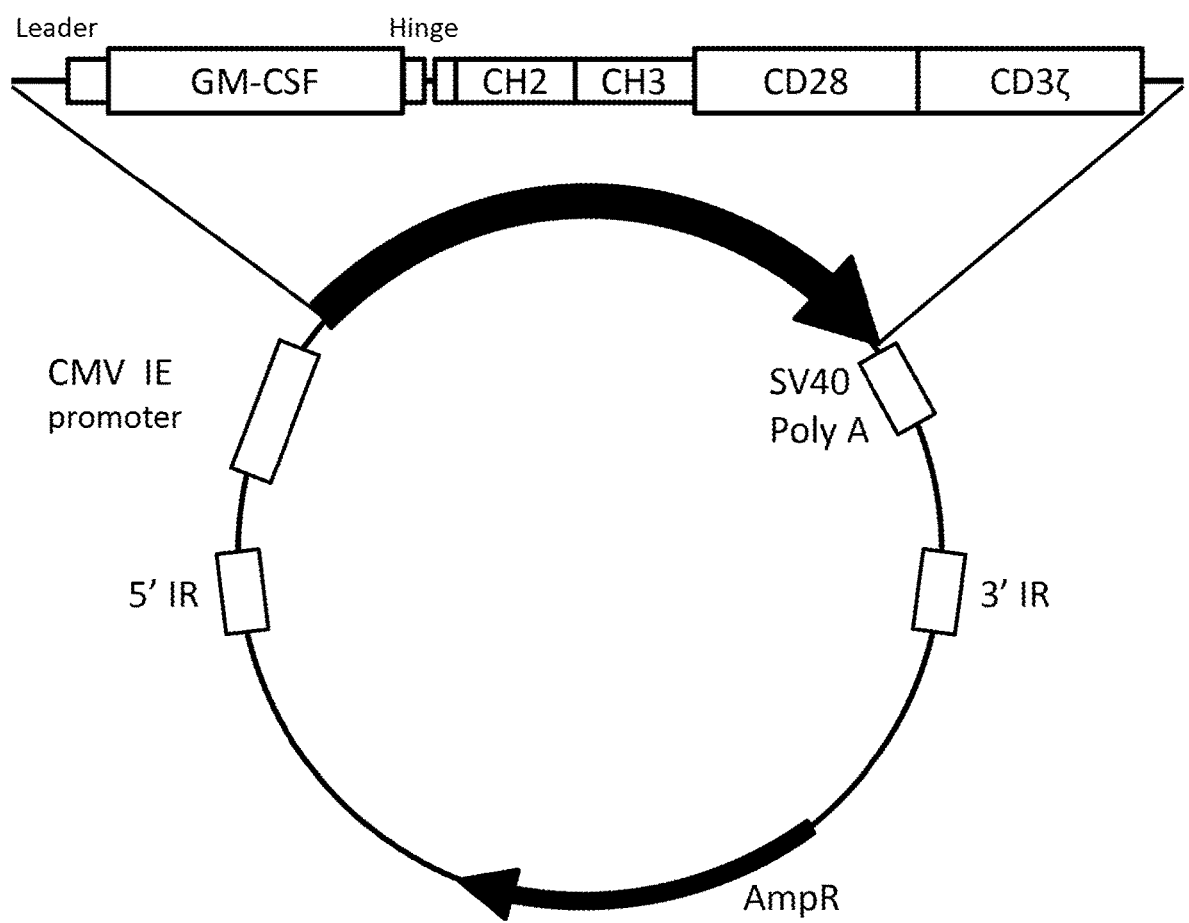
FIG. 2 shows an example of a vector map of a GMR.CAR of the present invention.
Figure 3:
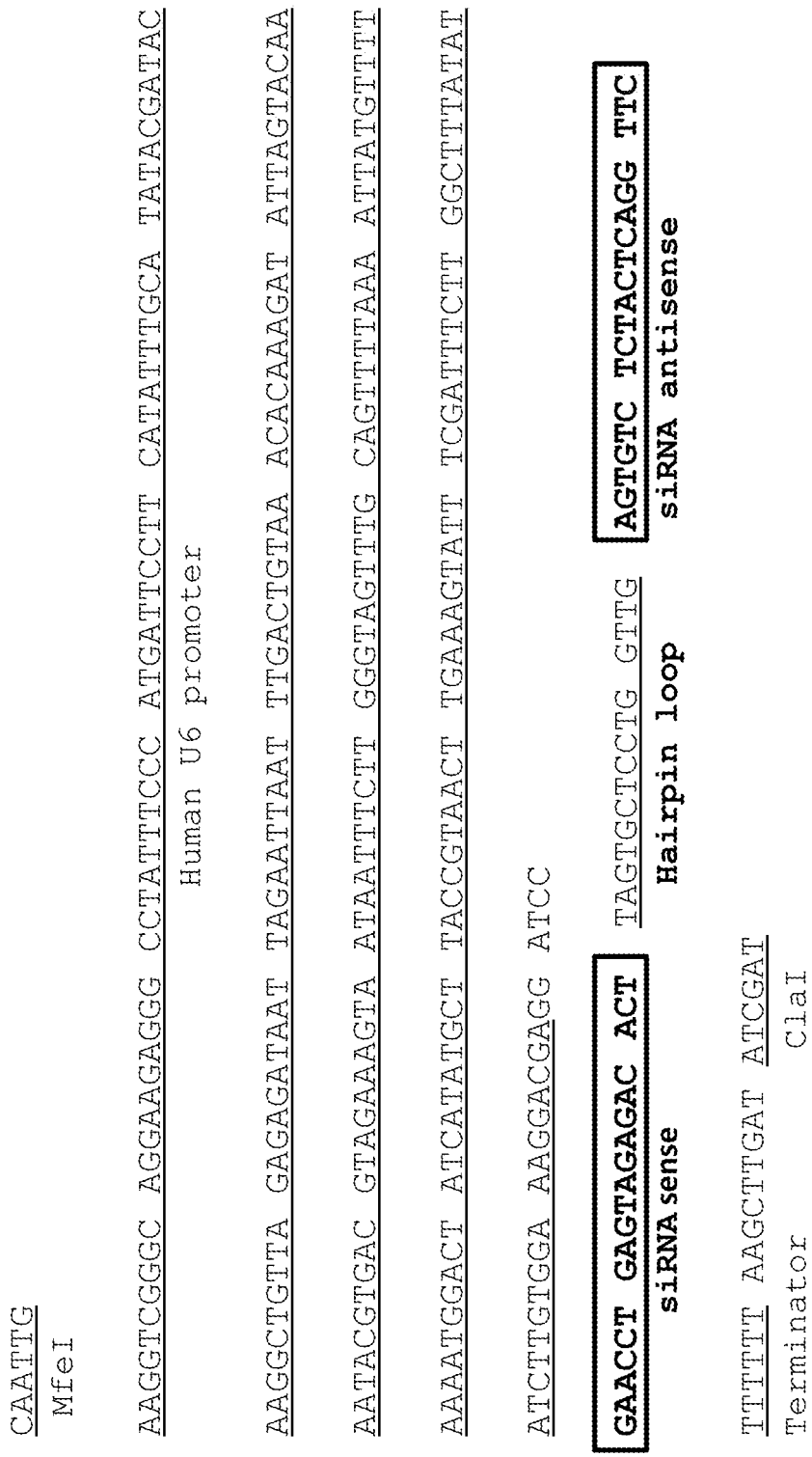
FIG. 3 shows a constitutional example of a synthesized sequence (SEQ ID NO: 19) containing a polynucleotide that induces RNAi.
Figure 4:
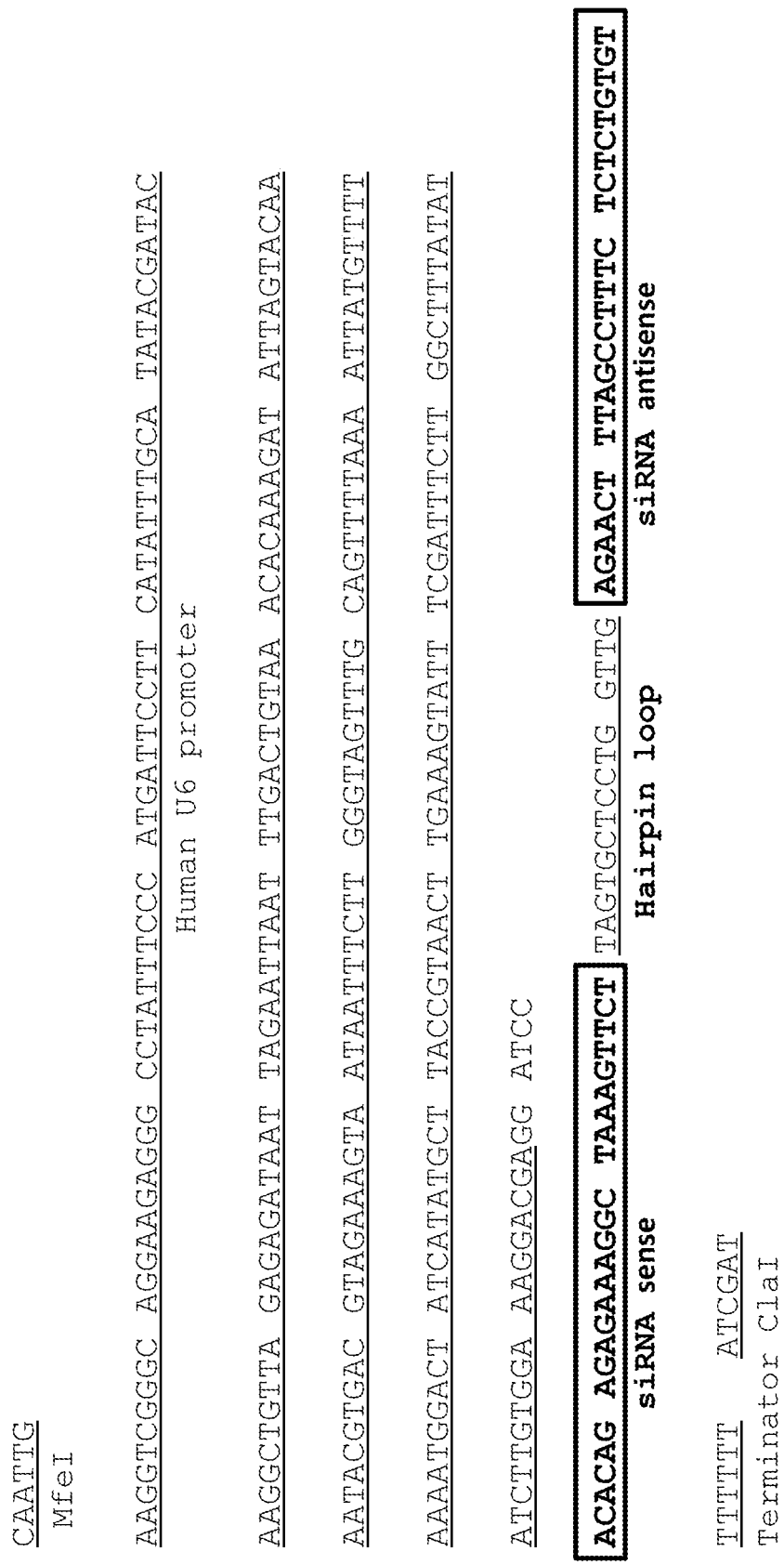
FIG. 4 shows a constitutional example of a synthesized sequence (SEQ ID NO: 29) containing a polynucleotide (SEQ ID NO: 22) that induces RNAi.
Figure 5:
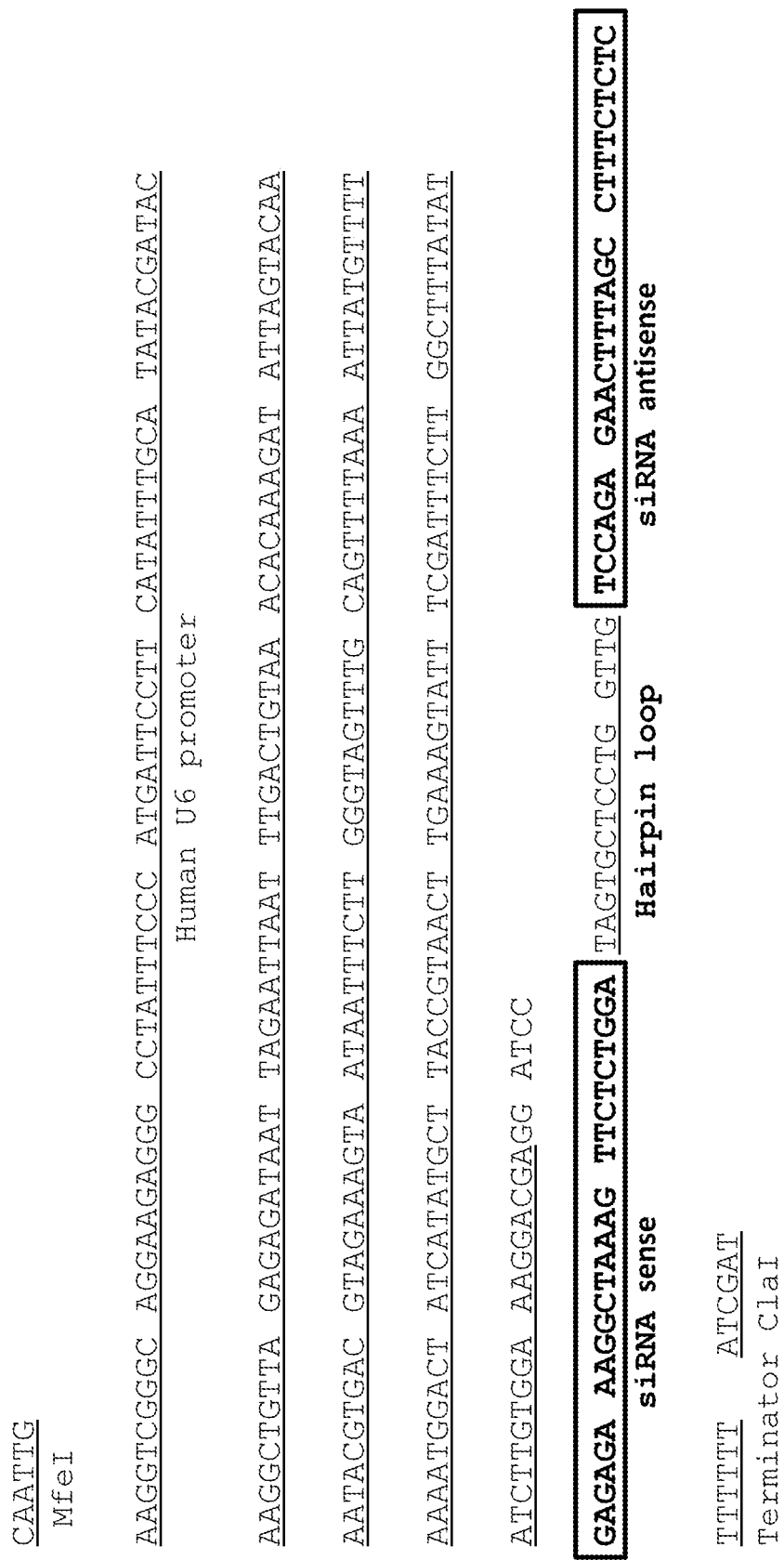
FIG. 5 shows a constitutional example of a synthesized sequence (SEQ ID NO: 30) containing a polynucleotide (SEQ ID NO: 25) that induces RNAi.
Figure 6:
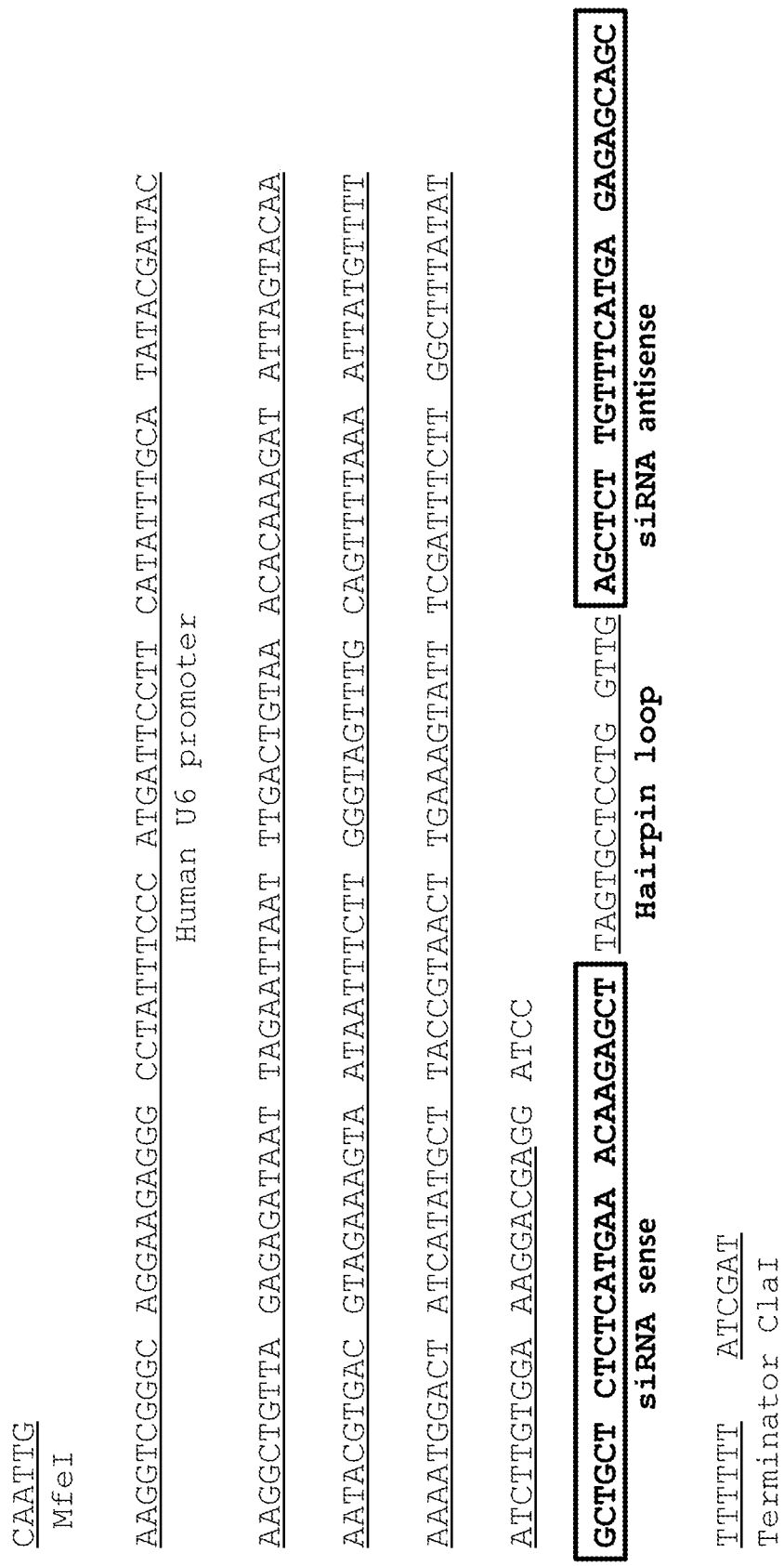
FIG. 6 shows a constitutional example of a synthesized sequence (SEQ ID NO: 31) containing a polynucleotide (SEQ ID NO: 28) that induces RNAi.

FIG. 1 shows a vector map of pIRII-CD19.CAR, based on which CAR 001 was produced. FIG. 2 shows a vector map of CAR 001 produced.

Example 2 Design of siRNA and Synthesis of shRNA

Based on the sequence of human GM-CSF (NCBI Accession No.: NM_000758.3, SEQ ID NO: 1), a pair of siRNAs (SEQ ID NOs: 17 and 18) specific to the mRNA within a coding region was designed by outsourcing to Takara Bio Inc.

Separately, siRNAs specific to the mRNA sequence in 5'-untranslated region (5'-UTR) or 3'-untranslated region (3'-UTR) of human GM-CSF were designed using BLOCK-iT® RNAi Designer (Thermo Fisher Scientific K.K.) and three pairs of siRNAs were arbitrarily selected (SEQ ID NOs: 20 and 21, 23 and 24, 26 and 27).

Figure 7:
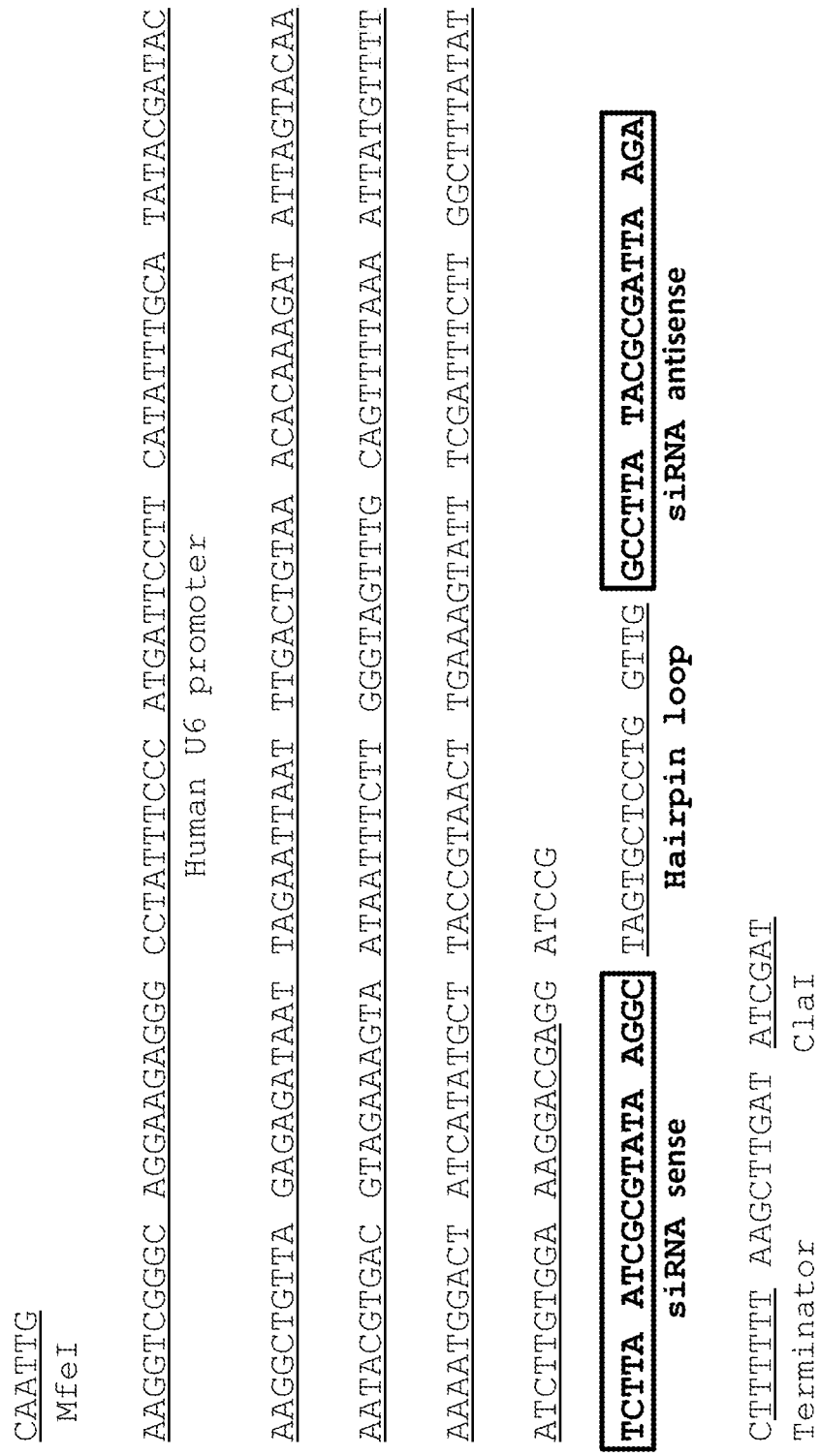
FIG. 7 shows a constitutional example of a synthesized sequence (SEQ ID NO: 32) containing a polynucleotide (SNC1-C (Takara Bio Inc.)) that induces RNAi.

DNA sequences were artificially synthesized by ligating the sense strand and antisense strand of respective siRNAs mentioned above to a portion immediately downstream of a human U6 promoter sequence, via a hairpin loop (outsourced to Takara Bio Inc. or Eurofins Genomics K.K.). A sequence to be cleaved with a restriction enzyme MunI (MfeI) was added to the 5' side of the artificially synthesized gene, and a sequence to be cleaved with a restriction enzyme ClaI was added to the 3' side thereof. The synthesized sequences were shown in SEQ ID NOs: 19 and 29 to 31 (FIGS. 3 to 6). As a negative control sequence, SNC1-C (Takara Bio Inc.) having sequences to be cleaved with MunO (MfeO) and ClaI added in the same manner was used (FIG. 7, SEQ ID NO: 32).

Example 3 Production of GMR.CAR+siRNA Construct

DNAs artificially synthesized in Example 2 (SEQ ID NOs: 29 to 31) and SNC1-C (Takara Bio Inc., SEQ ID NO: 32) having sequences to be cleaved with MunI (MfeI) and ClaI added were integrated into a pTAKN-2 vector (BioDynamics Laboratory Inc.) or pBAsi vector (Takara Bio Inc.). The obtained vector was dissolved so as to obtain a concentration of 100 ng/μL. *Escherichia coli* HST04 strain (Takara Bio Inc.) was transformed using the aliquot (1 μL (corresponding to 100 ng)) from the solution, and cultured on an LB agar medium containing 50 μg/mL kanamycin for about 16 hours. Separately, HST04 strain was also transformed with the GMR.CAR expression pasmid produced in Example 1 (CAR 001) and cultured on an LB agar medium containing 50 μg/mL ampicillin for about 16 hours.

Colonies emerged were further cultured in an LB liquid medium containing 50 μg/mL kanamycin or ampicillin for about 16 hours. From *Escherichia coli* culture solutions, individual plasmids were purified using QIAprep Spin Miniprep Kit (QIAGEN K.K.). The purified plasmids (corresponding to 0.5 to 1 μg) were each digested with restriction enzymes MfeI and ClaI (New England Biolabs, Inc.) for about 3 hours. The reaction solutions treated with the enzymes were each separated by 1% agarose gel electrophoresis. The insert fragment cut out from the pTAKN-2 vector and a fragment of CAR 001 treated with the enzymes were excised out from the gel, and purified using Nucleo-Spin Gel and PCR Clean-Up® (MACHEREY-NAGEL GmbH & Co. KG, Takara Bio Inc.). The purified insert fragment and vector fragment were ligated using DMA Ligation Kit <Mighty Mix> (Takara Bio Inc.). An *Escherichia coli* DH5α (Toyobo Co., Ltd.), TOP10 (Thermo Fisher Scientific K.K.) or HST04 strain was transformed by the ligated circular vector and cultured on an LB agar medium containing 50 μg/mL ampicillin for about 16 hours.

Figure 8:
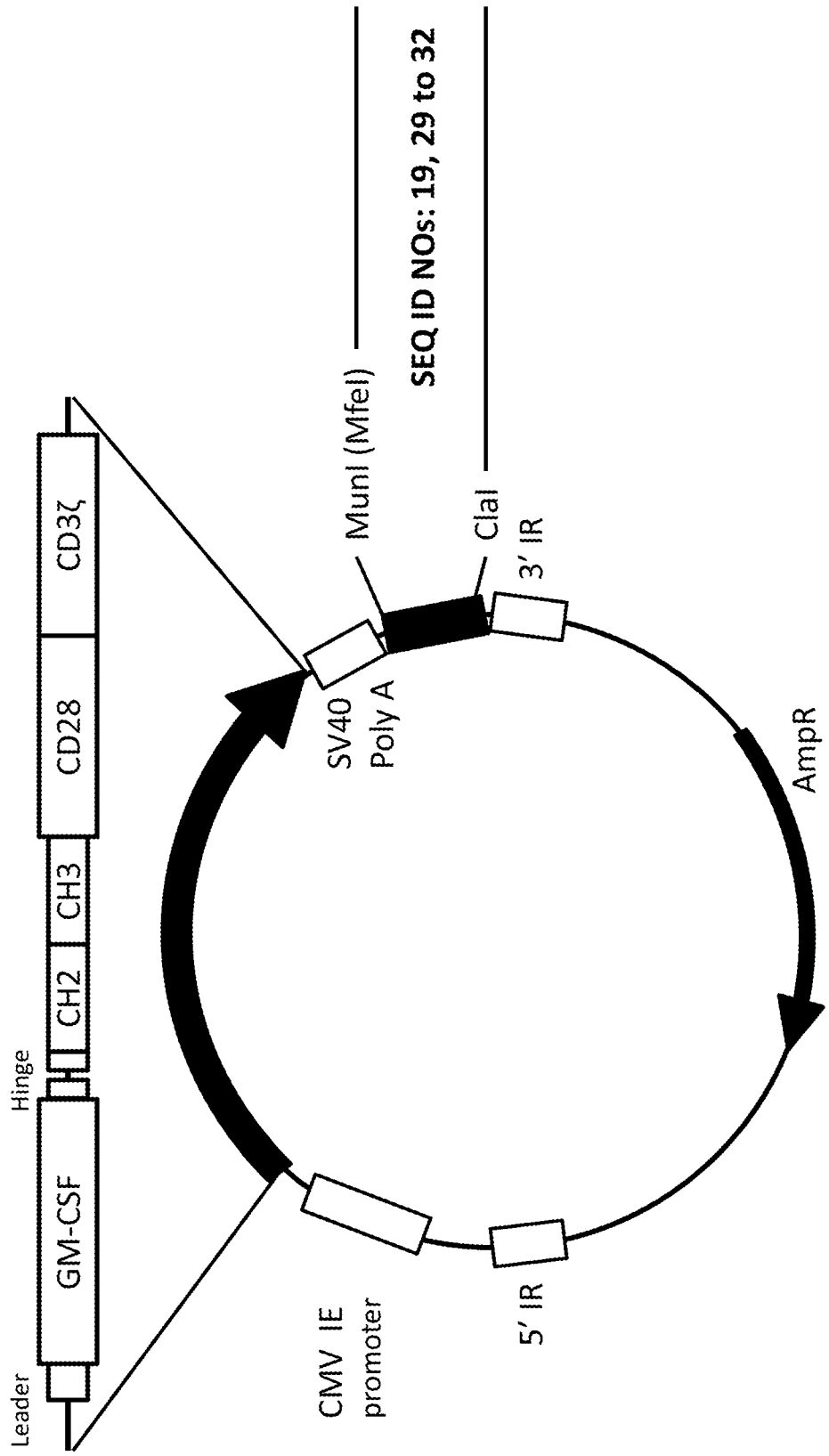
FIG. 8 shows an example of a vector map of a GMR.CAR+shRNA of the present invention.

Colonies emerged were further cultured in an LB liquid medium containing 50 μg/mL ampicillin for about 16 hours. From the *Escherichia coli* culture solution, individual plasmids were purified using QIAprep Spin Miniprep Kit (QIAGEN K.K.). The purified plasmids (corresponding to 0.5 to 1 μg) were digested with a restriction enzyme BamHI (New England Biolabs. Inc.) for about 3 hours. Presence of the inserted fragment was checked by 1% agarose gel electrophoresis. Samples in which the inserted fragment was confirmed were subjected to sequencing. The samples containing nucleotide sequences completely matched with the sequences represented by SEQ ID NOs: 29 to 32 were determined as GMR.CAR+shRNA insert expression plasmids [designated as CAR 004 (GMR.CAR+5'-UTR_1), CAR 005 (GMR.CAR+5'-UTR_6), CAR 006 (GMR.CAR+3'-UTR_500) and CAR 007 (GMR.CAR+SNC1-C)] (FIG. 8).

For the following study, *Escherichia coli* containing a GMR.CAR+shRNA insert expression plasmid or a mutant GMR.CAR+shRNA insert expression plasmid was cultured, and a plasmid solution, which was purified using Endofree Plasmid Maxi Kit (QIAGEN K.K.). was used.

Comparative Example 1 GM-CSF Mutant GMR.CAR Expression Plasmid

Since siRNAs to a coding region may possibly affect the expression of GM-CSF, a target binding domain of GMR.CAR, a mutation inhibiting amino acid substitutions was introduced into the GM-CSF mRNA sequence (159 to 179 nucleotides of NCBI Accession No.: NM_000758.3 (SEQ ID NO: 1)) portion (SEQ ID NOs: 3 and 4). More specifically, the nucleotide sequence at positions 159 to 179 in the nucleotide sequence of SEQ ID NO: 1 was mutated into the nucleotide sequence at positons 127 to 147 in the nucleotide sequence of SEQ ID NO: 3. This mutant was produced by replacing the wild type GM-CSF sequence of CAR 001 with an artificially synthesized gene prepared by introducing a mutation into nucleotides of the mRNA sequence to which an siRNA is to be bound. More specifically, an XhoI-secretory signal sequence-GM-CSF mutant-hinge sequence-DraIII fragment having a sequence to be cleaved with a restriction enzyme XhoI at the 5' side and a sequence to be cleaved with a restriction enzyme DraIII at the 3' side was artificially synthesized (outsourced to Eurofins Genomics K.K.). This fragment was connected to a fragment obtained by treating CAR 001 with XhoI and DraIII to produce a GM-CSF mutant GMR.CAR expression plasmid.

Comparative Example 2 Production of GM-CSF Mutant GMR.CAR+siRNA Construct

The DNA artificially synthesized in Example 2 (SEQ ID NO: 19) and SNC1-C (Takara Bio Inc., SEQ ID NO: 32) having sequences to be cleaved with MunI (MfeI) and ClaI added were separately integrated into pBAsi vectors (Takara Bio Inc.). An *Escherichia coli* HST04 strain (Takara Bio Inc.) was transformed in the same manner as in Example 3 and then cultured on an LB agar medium containing 50 μg/mL kanamycin for about 16 hours. Separately. HST04 strain was also transformed with a GM-CSF mutant GMR.CAR expression plasmid (CAR 002) produced in Comparative Example 1 and cultured on an LB agar medium containing 50 μg/mL ampicillin for about 16 hours.

Colonies emerged were further cultured in an LB liquid medium containing 50 μg/mL kanamycin or ampicillin for about 16 hours. The samples containing nucleotide sequences completely matched with those of SEQ ID NOs: 19 and 32 were determined as GM-CSF mutant GMR.CAR+shRNA insert expression plasmids [designated as CAR 002 (mutant GMR.CAR+shRNA) and CAR 003 (mutant GMR.CAR+SNC1-C)], in the same manner as in Example 3.

Example 4 Confirmation of Expression of GM-CSF Mutant GMR.CAR+shRNA Insert Expression Plasmids (CAR 002 and CAR 003) or GMR.CAR+shRNA Insert Expression Plasmids (CAR 004 to CAR 007)

HEK293T cells (strain derived from human embryonic kidney cell HEK293 cells expressing an SV40 Large T antigen, RIKEN) were diluted with D-MEM containing 10% FBS (Wako Pure Chemical Industries, Ltd.), seeded in a 24-well treatment culture plate at a ratio of $4 \times 10^5$ cells/well (500 μL) and cultured overnight. To the cells cultured overnight, a solution mixture, which was prepared by adding a plasmid diluent containing 0.8 μg of each of CAR 001 to 007 in 50 μL Opti-MEM (Thermo Fisher Scientific K.K.), and 2 μL of a lipofectamine 2000 reagent (Thermo Fisher Scientific K.K.) in 50 μL Opti-MEM in the same mounts, was allowed to stand still at room temperature for 20 minutes and added to the seeded cells in an amount of 100 μL/well. The cells were further cultured for about 48 hours in a $CO_2$ incubator. As controls, a group to which Opti-MEM (100 μL) was added and a group to which a lipofectamine reagent alone not containing a plasmid was added were employed.

After 48 hours, cells were recovered and centrifuged. Then, 2.5 μL of PE Rat Anti-Human GM-CSF antibody (BD Pharmingen) and 5 μL of APC Anti-Human CD116 antibody (Miltenyi Biotec GmbH) were added and suspended, and an antibody labeling reaction was carried out at 4° C. in the dark for 20 minutes. After 20 minutes, the cells were washed with an appropriate amount of D-PBS and centrifuged to precipitate the cells. After the supernatant was removed, the cells were resuspended in an appropriate amount of D-PBS. The resuspension sample was analyzed using FACSCalibur (BD) to determine the expression rate of a GM-CSF/CD3-positive GMR.CAR.

Figure 9:
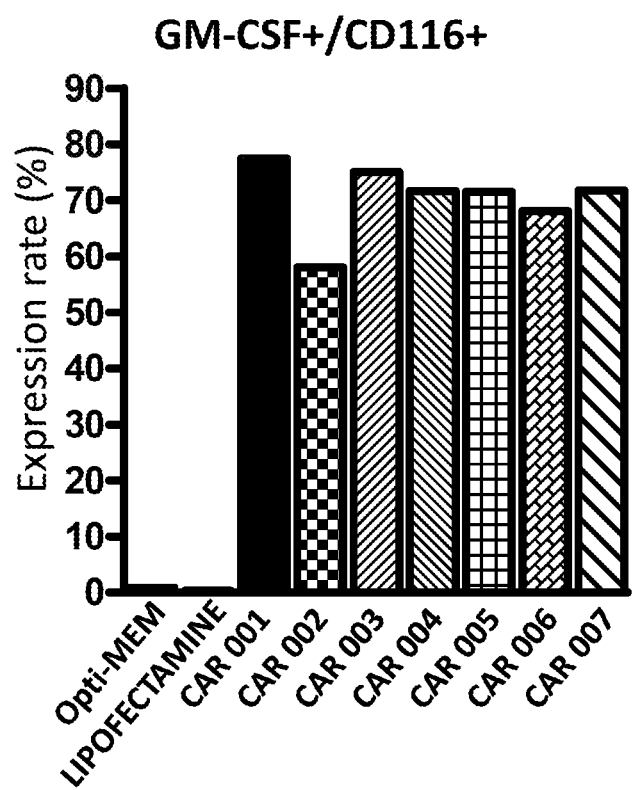
FIG. 9 shows the expression rate of GMR.CAR (%) in HEK293T cells into which a polynucleotide encoding a GMR.CAR and a polynucleotide that induces RNAi were introduced.

FIG. 9 shows the expression rates (%) of a GM-CSF-positive GMR.CAR 48 hours after CAR 001 to 007 were gene-introduced to HEK293T cells. As a result, in the case of introducing CAR 002, that can induce RNAi to the coding region of GM-CSF gene, the expression rate of a GMR.CAR was the lowest compared to the others. In contrast, the expression rates of GMR.CARs in the cases of introducing negative control shRNA inserts (CAR 003 and CAR 007) and untranslated region shRNA inserts (CAR 004 to 006) rarely declined. CAR 002 is a mutant prepared by inserting an shRNA specific to the coding region of GM-CSF mRNA and introducing a nucleotide mutation in the siRNA recognition portion of the GM-CSF gene sequence; however, the possibility that, even if the nucleotide mutation is introduced, the siRNA exerts a certain level of knockdown effect and suppresses expression of GMR.CAR itself, was considered.

Example 5 Culture/Amplification of GMR.CAR-T Cell_1

<Day 0: Isolation of Human Peripheral Blood Mononuclear Cells (PBMCs) and Electrical Introduction of GMR. CAR Expression Vector>

Peripheral blood was taken from a healthy adult donor, diluted by a factor of 2 with D-PBS (Wako Pure Chemical Industries, Ltd.), and then overlayered on Ficoll-Paque PLUS (GE Healthcare) and centrifuged at 400×g for 30 minutes to collect PBMCs. The collected PBMCs were washed twice with D-PBS and isolated by centrifugation. $10 \times 10^6$ PBMCs were used for introduction of the GMR. CAR expression plasmid (CAR 001). More specifically. CAR 001 (5 μg), pCMV-piggyBac plasmid (5 μg) and P3 Primary Cell solution (100 μL) in P3 Primary Cell 4D-Nucleofector™ X Kit (Lonza Japan Ltd.) were mixed, and $10 \times 10^6$ PBMCs were suspended. The total amount of the suspended cells was transferred to Nucleocuvette and electrical gene introduction was carried out by 4D-Nucleofection (Program No: FI-115). The cells to which the electrical gene introduction was applied were allowed to stand still at room temperature for 10 minutes, and the total amount of the cells was cultured in a pre-warmed 24-well treatment culture plate containing TexMACS medium (Miltenyi Biotec GmbH) (2 mL/well) supplemented with 10 ng/mL IL-7 and 5 ng/mL IL-15. $1 \times 10^6$ Mock-T cells to which gene introduction operation was not applied were cultured in the same manner. Medium exchange was appropriately carried out by discarding a half amount of the culture medium and adding a half amount of TexMACS medium supplemented with 20 ng/mL IL-7 and 10 ng/mL IL-15 (double concentration).

<Days 1 to 4: Stimulation of Gene-Introduced Cells With Nonspecific Antibody>

A 24-well non-treatment culture plate was treated with D-PBS containing an anti-CD3 antibody and an anti-CD28 antibody (Miltenyi Biotec GmbH) at 37° C. for 2 hours to be coated with the antibodies. The total amount of the culture solution of day 0 was transferred to the a mi body-coated plate and nonspecific antibody stimulation for T cells was applied until day 4.

<Day 4: Amplification of T Cells>

The T cells to which nonspecific antibody stimulation was applied from day 1 were returned to a 24-well treatment culture plate, continued to culture and amplified.

<Day 7: Amplification of CAR-T Cells>

The total amount of the cell suspension was transferred to G-Rex 10 (Wilson Wolf Corporation) filled with TexMACS medium (30 mL) supplemented with 10 ng/mL IL-7 and 5 ng/mL IL-15, and CAR-T cells were amplified until day 14. The expression rate of GMR.CAR cells amplified until day 14 was determined by the following method. Mock-T cells were continuously cultured on a 24-well treatment culture plate, and medium exchange and amplification were carried out depending on the cell proliferation rate.

<Day 14: Evaluation of GMR.CAR Expression Rate>

Cells were counted and 1 to $2 \times 10^5$ cells were subjected to flow cytometric analysis to evaluate the expression rate of GMR.CAR-T. 1 to $2 \times 10^5$ cells were taken and 2 μL of FITC Goat Anti-Human IgG (H+L) antibody (Jackson ImmunoResearch Inc.) or 2.5 μL of PE Rat Anti-Human GM-CSF antibody (BD Pharmingen) and 5 μL of APC Anti-Human CD3 antibody (Miltenyi Biotec GmbH) were added and suspended, and an antibody labeling reaction was carried out at 4° C. in the dark for 20 minutes. After 20 minutes, the cells were washed with an appropriate amount of D-PBS and precipitated by centrifugal ion. After the supernatant was removed, the cells were resuspended in an appropriate amount of D-PBS. The resuspension sample was analyzed using FACSCalibur (BD) to determine the expression rate of IgG1 CD3-positive or GM-CSF/CD3-positive GMR.CAR. GMR.CAR-T cells obtained by electrical introduction of GMR.CAR expression plasmid (CAR 001) into PBMCs and T cell culture/amplification were defined as CAR-T 001.

Figure 10:
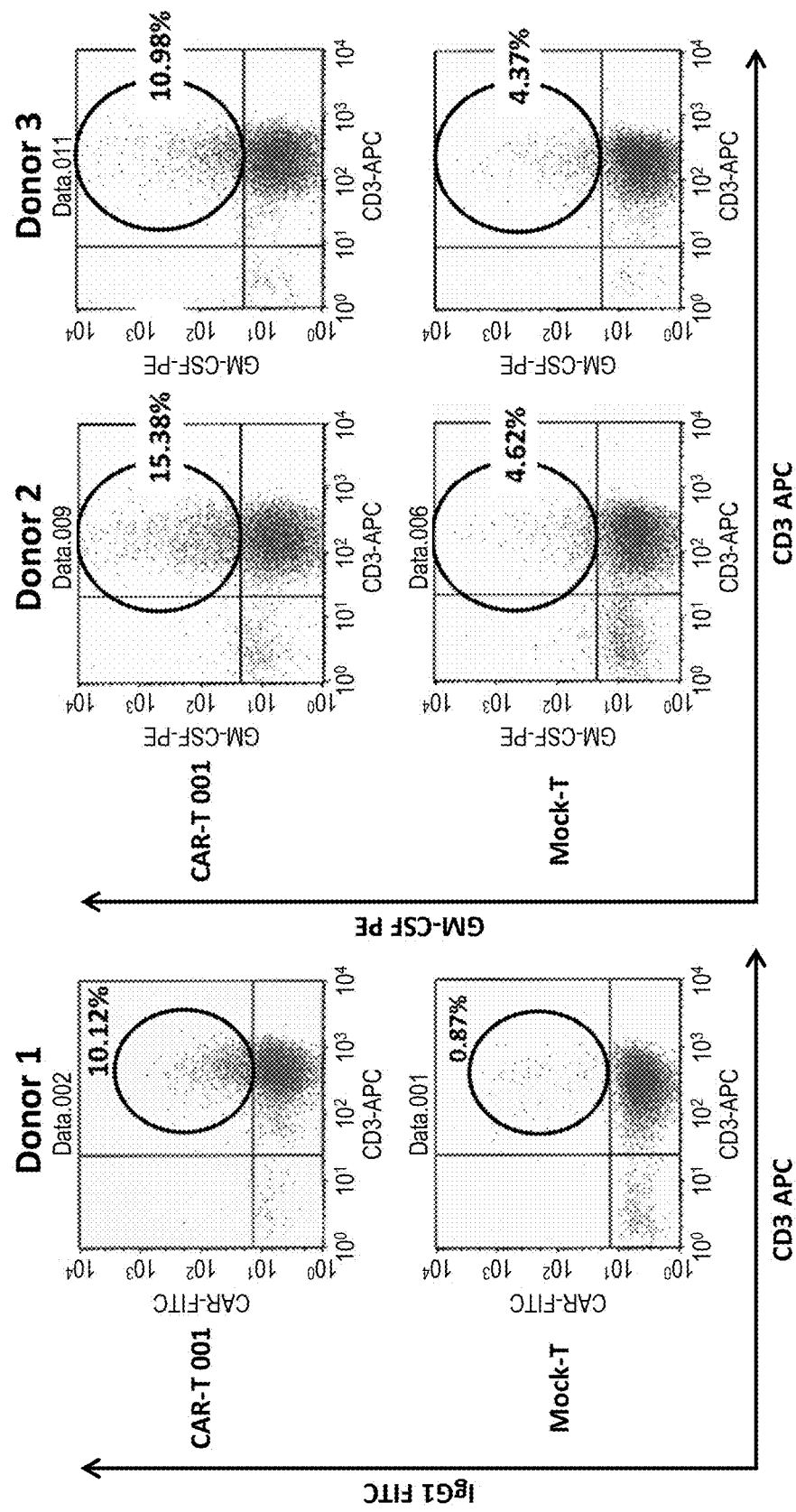
FIG. 10 shows the expression rate of GMR.CAR (%) on day 14 in GMR.CAR-T cells (CAR-T 001) into which a polynucleotide encoding a GMR.CAR was introduced.

FIG. 10 shows the results of expression analysts for CAR-T 001 produced from three healthy adult donors on day 14. The GMR.CAR expression rate in CAR-T 001 was as follows: donor 1: 10.12% (IgG/CD3-positive rate), donor 2: 15.38% and donor 3: 10.98% (both are GM-CSF/CD3-positive rates), which were higher than the expression rates in Mock-T cells corresponding to respective donors (donor 1: 0.87%, donor 2: 4.62% and donor 3: 4.37%), indicating that the GMR.CAR-expressing T cells (CAR-T 001) were successfully produced.

Example 6 Evaluation of Antitumor-Cell Activity of CAR-T 001 and Secretion Level of GM-CSF <Evaluation of Antitumor-Cell Activity>

To evaluate the tumor cytotoxic activity of CAR-T 001, a co-culture test with tumor cells was carried out. More specifically, THP-1, Kasumi-1 or K562 cells (American Type Culture Collection (ATCC)) were used, and these tumor cells [target (T)] were controlled with an RPMI 1640 medium containing 10% FBS (Thermo Fisher Scientific K.K.) such that $10\times10^5$ cells/mL were present, and seeded in a 48-well treatment culture plate at a ratio of 500 µL/well (the number of cells per well is $5\times10^5$). CAR-T 001 [effector (E)] was diluted with an RPMI 1640 medium containing 10% FBS so as to obtain an E to T ratio of 1:5 to 1:50. More Specifically, in the case of the E to T ratio=1:5, CAR-T 001 was controlled such that $2\times10^5$ cells/mL were present, and added to the 48-well treatment culture plate having the tumor cells seeded therein, at a ratio of 500 µL/well (the number of cells per well is $1\times10^5$). Also, in the case of the E to T ratio=1:50, CAR-T 001 was controlled such that $0.2\times10^5$ cells/mL were present, and added to the 48-well treatment culture plate having the tumor cells seeded therein, at a ratio of 500 µL/well (the number of cells per well is $0.1\times10^5$).

The co-culture test was carried out for 5 days. Mock-T cells were also subjected to the same co-culture test. As a control group, tumor cells alone of the same number of cells were employed (CAR-T non-addition group). On day 5 of the co-culture test cells were collected from individual wells and stained with trypan blue, and then, viable cells were counted. The cells were centrifuged, and 5 µL of APC Anti-Human CD3 antibody (Miltenyi Biotec GmbH) and 5 µL of PE Anti-Human CD33 antibody were added and suspended, and an antibody labeling reaction was carried out at 4° C. in the dark for 20 minutes. After 20 minutes, the cells were washed with an appropriate amount of D-PBS and precipitated by centrifugation. After the supernatant was removed, the cells were resuspended in an appropriate amount of D-PBS. The resuspension sample was analyzed using FACSCalibur. The CD33-positive rate was determined and the antitumor-cell activity (%) of CAR-T 001 or Mock-T cells was calculated in accordance with the following formulae.

<Calculation of Antitumor-Cell Activity>
Formulae:

Number of CD33-positive cells=(number of trypan blue-stained viable cells×CD33-positive rate (%) in FACS)/100

Antitumor-cell activity (%)=100−(number of CD33-positive cells in CAR-T addition group)/(number of CD33-positive cells in CAR-T non-addition group)×100

Figure 11:
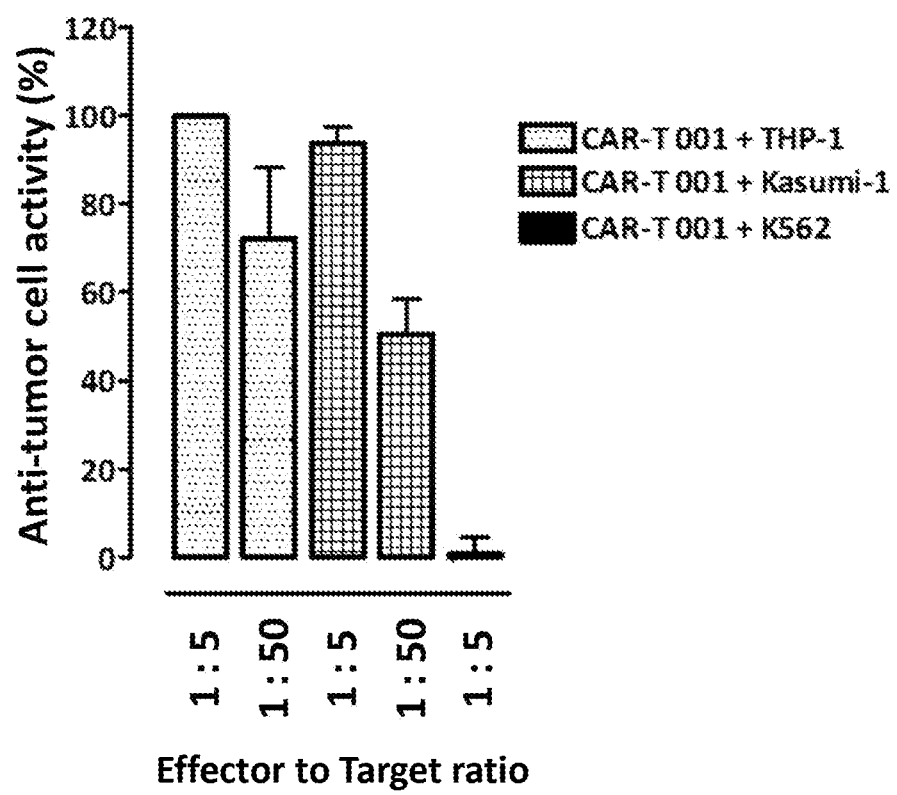
FIG. 11 shows the antitumor-cell activity (%) of GMR.CAR-T cells (CAR-T 001) against THP-1, Kasumi-1 or K562 cells.

FIG. 11 shows the results of the antitumor-cell activity (%) of CAR-T 001, which was produced using cells derived from three healthy adult donors, against THP-1, Kasumi-1 or K562 cells. Data were average values of antitumor-cell activities (%) of CAR-T 001 from three donors. It was confirmed that CAR-T 001 completely kills THP-1 and Kasumi-1 cells at an E to T ratio of 1.5 and has a strong antitumor-cell activity even at an E to T ratio of 1:50. In contrast, K562 cells not expressing CD116, which is a GM-CSF receptor α chain, were not killed at all by CAR-T 001.

<Evaluation of GM-CSF Secretion Level>

The culture supernatant from the sample of E to T ratio of 1:5 from day 1 to day 5 in the similar co-culture test as in the above antitumor-cell activity evaluation was collected and cryopreserved at −30° C. until use for measurement. After the cryopreserved culture supernatant was thawed and diluted 10 fold with D-PBS, the secretion level of GM-CSF in the culture supernatant was measured using Himan GM-CSF Quantikine ELISA Kit (R&D Systems. Inc.).

Figure 12:
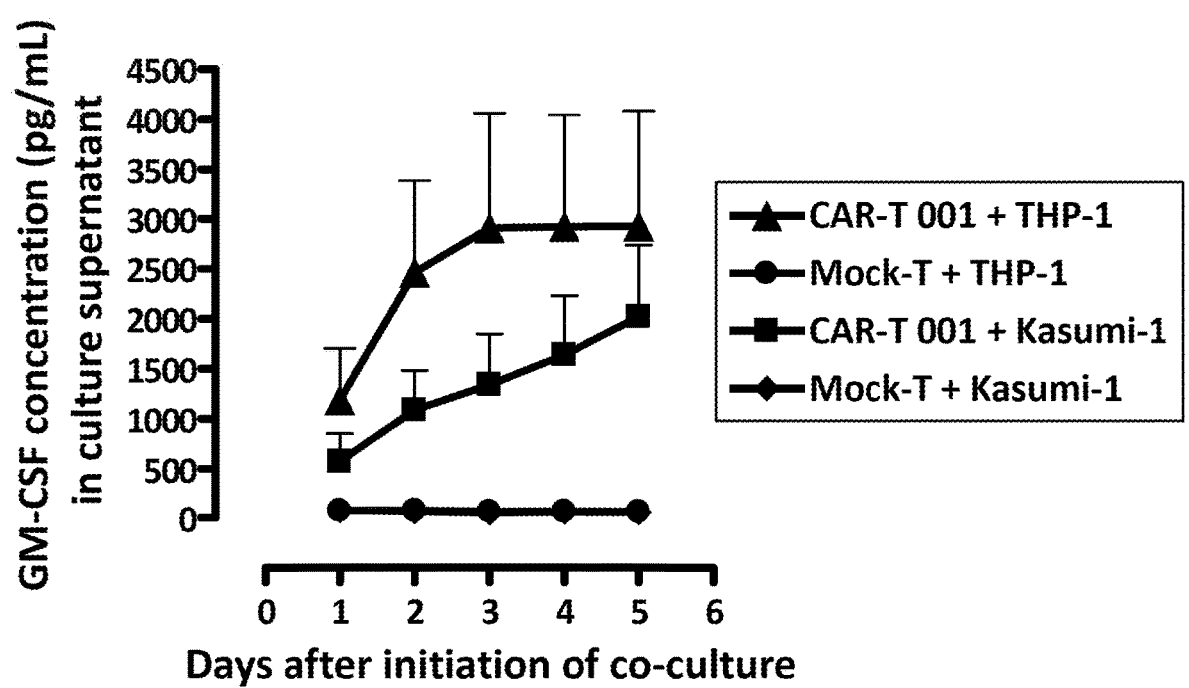
FIG. 12 shows the time-dependent change of the secretion level of GM-CSF in the supernatant of the co-culture of GMR.CAR-T cells (CAR-T 001) and THP-1 or Kasumi-1 cells.

FIG. 12 shows the results of GM-CSF secretion level in the co-culture supernatant of CAR-T 001 and THP-1 or Kasumi-1 cells. It was continued that CAR-T 001 secretes GM-CSF on day 1 of the co-culture with THP-1 or Kasumi-1 cells, and that the amount of GM-CSF secreted significantly increases until day 3 (peak) in the co-culture with THP-1 cells, and until day 5 in the co-culture with Kasumi-1 cells. In contrast, in the co-culture with Mock-T to which gene introduction operation was not applied, an increase in the amount of GM-CSF was not confirmed in both culture supernatants.

Example 7 Effect of Co-Presence of GM-CSF on Antitumor-Cell Activity of CAR-T 001

In the 5-day co-culture test of CAR-T 001 and THP-1 or Kasumi-1 cells, the effect of co-presence of GM-CSF on the antitumor-cell activity of CAR-T 001 was evaluated by artificially adding GM-CSF (0 to 10 ng/mL).

Figure 13:
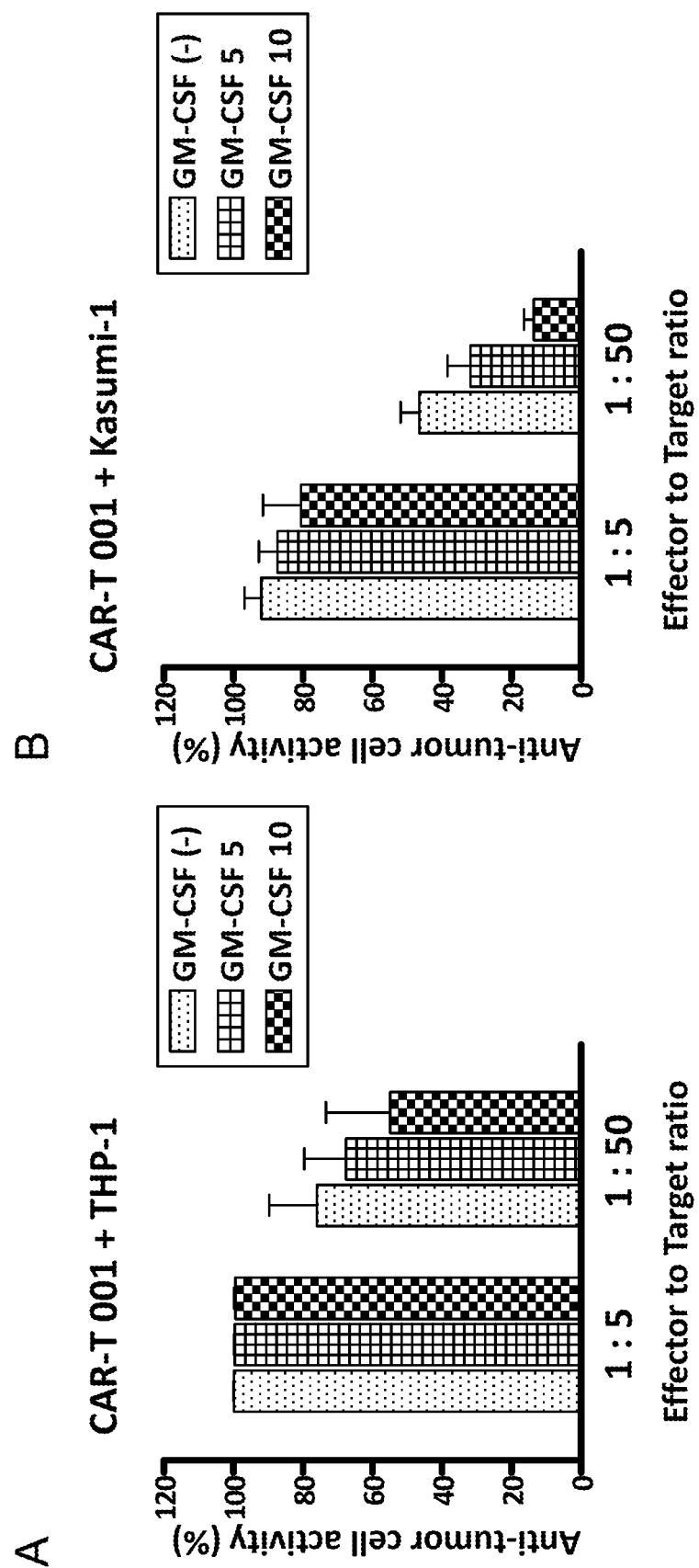
FIG. 13 shows the antitumor-cell activity (%) of GMR.CAR-T cells (CAR-T 001) against THP-1 (A) or Kasumi-1 cells (B) in the presence of GM-CSF (0, 5 or 10 ng/ml).

FIG. 13 shows the anti-tumor cell activity of CAR-T 001 against THP-1 or Kasumi-1 cells in the co-presence of GM-CSF. It was confirmed that the effect of the co-presence of GM-CSF on the anti-tumor cell activity of CAR-T 001 against THP-1 cells at an E to T ratio of 1:5 was not observed; however, the anti-tumor cell activity decreases depending on the concentration of GM-CSF at an E to T ratio of 1:50. It was also confirmed that the anti-tumor cell activity of CAR-T 001 against Kasumi-1 cells decreases depending on the concentration of GM-CSF at an E to T ratio of 1:5 and 1:50.

Example 8 Culture/Amplification of GMR.CAR-T Cell_2

<Day 3: Isolation of PBMCs and Production of T Cell-Nonspecific Stimulated OKT 3 Blast (Blast Cells Stimulated Non-Specifically with Anti-CD3 Antibody)>

3 days before gene introduction operation, peripheral blood was taken from a healthy adult donor, diluted by a factor of 2 with D-PBS (Wako Pure Chemical Industries, Ltd.), and then overlayered on Ficoll-Paque PLUS and centrifuged at 400×g for 30 minutes to collect PBMCs. The collected PBMCs were washed twice with D-PBS and isolated by centrifugation. The isolated PBMCs were suspended in TexMACS medium supplemented with 5 ng/mL IL-15 such that 2 to $4\times10^6$ cells/well/2 mL were present. A 24-well non-treatment culture plate was treated with D-PBS containing an anti-CD3 antibody and an anti-CD28 antibody at 37° C. for 2 hours. In this manner, the plate was coaled with the antibodies. The cell suspension was supplied at a ratio of 2 mL/well to carry out specific stimulation of T cells to produce OKT3 blast.

<Day 0: Viral Peptide Pulse of OKT3 Blast>

OKT3 blast to which nonspecific antibody stimulation was applied on day −3 was collected and subjected to viral peptide stimulation using PepTivalor® peptide pool (Miltenyi Biotec GmbH). More specifically, OKT3 blast was suspended in the peptide pool, in which 0.05 µg/µL each of AdV5 Hexon, CMV pp65, EBV BZLF1 and EBV EBNA-1 were added in D-PBS (50 µL), and subjected to viral peptide stimulation at 37° C. for 30 minutes. This method was defined as ACE method by taking initial letters of the names of these viral peptides. 30 minutes later, an appropriate amount of D-PBS was added to OKT3 blast and suspended, and then, UV irradiation was applied for 4 minutes. The UV-irradiated OKT3 blast was collected and the cells were counted. The cells were then suspended in TexMACS medium supplemented with 10 ng/mL IL-7 and 5 ng/mL IL-15 such that 0.5 to $2\times10^6$ cells/well/2 mL were present, and transferred to a 24-well treatment culture plate as feeder cells. The rest of OKT3 blast exposed to neither viral peptide pulse nor UV irradiation was continuously cultured in a 24-well treatment culture plate containing TexMACS medium supplemented with 5 ng/mL IL-15.

<Day 0: Isolation of PBMCs and Gene Introduction Operation>

Peripheral blood was taken from a healthy adult donor and diluted by a factor of 2 with D-PBS (Wako Pure Chemical Industries, Ltd.), and then overlayered on Ficoll-Paque PLUS (GE Healthcare) and centrifuged at 400×g for 30 minutes to collect PBMCs. The collected PBMCs were washed twice with D-PBS and isolated by centrifugation. $10\times10^6$ PBMCs were used for introduction of a GMR.CAR expression plasmid. More specifically, any one of CAR 001 and CAR 004 to CAR 007 (5 µg), pCMV-piggyBac plasmid (5 µg) and P3 Primary Cell solution (100 µL) in P3 Primary Cell 4D-Nucleofector™ X Kit (Lonza Japan Ltd.) were mixed, and $10\times10^6$ PBMCs were suspended. The total amount of the suspended cells was transferred to Nucleocuvette and electrical gene introduction was carried out by 4D-Nucleofection (Program No: FI-115). The cells to which the electrical gene introduction was applied were allowed to stand still at room temperature for 10 minutes. The total amount of the cells was transferred to the 24-well treatment culture plate containing feeder cells and culture was initiated. $1\times10^6$ Mock-T cells from each donor to which gene introduction operation was not applied were similarly cultured. Medium exchange was appropriately carried out by discarding a half amount of the culture medium and adding a half amount of TexMACS medium supplemented with 20 ng/mL IL-7 and 10 ng/mL IL-15 (double concentration). The Mock-T cells were continuously cultured on a 24-well treatment culture plate and medium exchange and amplification were carried out depending on the cell proliferation rate.

<Day 7: Amplification of CAR-T Cells>

The total amount of the cell suspension was transferred to G-Rex 10 filled with TexMACS medium (30 mL) supplemented with 10 ng/mL IL-7 and 5 ng/mL IL-15 and containing $2\times10^6$ feeder cells produced in the same manner as in the operation on day 0. GMR.CAR-T cells were amplified until day 14. The expression rate of the GMR.CAR-T cells amplified until day 14 was determined by the following method.

<Day 14: Evaluation of GMR.CAR Expression Rate>

Cells were counted, and 1 to $2\times10^5$ cells were subjected to flow cytometric analysis to evaluate the expression rate of GMR.CAR-T. 1 to $2\times10^5$ cells were taken and PE Rat Anti-Human GM-CSF antibody (2.5 µL) and APC Anti-Human CD3 antibody (5 µL) were added and suspended, and an antibody labeling reaction was earned out at 4° C. in the dark for 20 minutes. After 20 minutes, the cells were washed with an appropriate amount of D-PBS and precipitated by centrifugation. After the supernatant was removed, the cells were resuspended in an appropriate amount of D-PBS. The resuspension sample was analyzed using FACSCalibur to determine the expression rate of GM-CSF/CD3-positive GMR.CAR. GMR.CAR-T cells obtained by electrical introduction using a GMR.CAR expression plasmid (CAR 001) and GMR.CAR+shRNA insert expression plasmids (CAR 004, CAR 005, CAR 006 and CAR 007) into PBMCs and T cell culture/amplification operation were designated as CAR-T 001, CAR-T 004, CAR-T 005, CAR-T 006 and CAR-T 007, respectively.

<Results of CAR-T 001 and 004 to 007 Produced by ACE Method>

Figure 14:
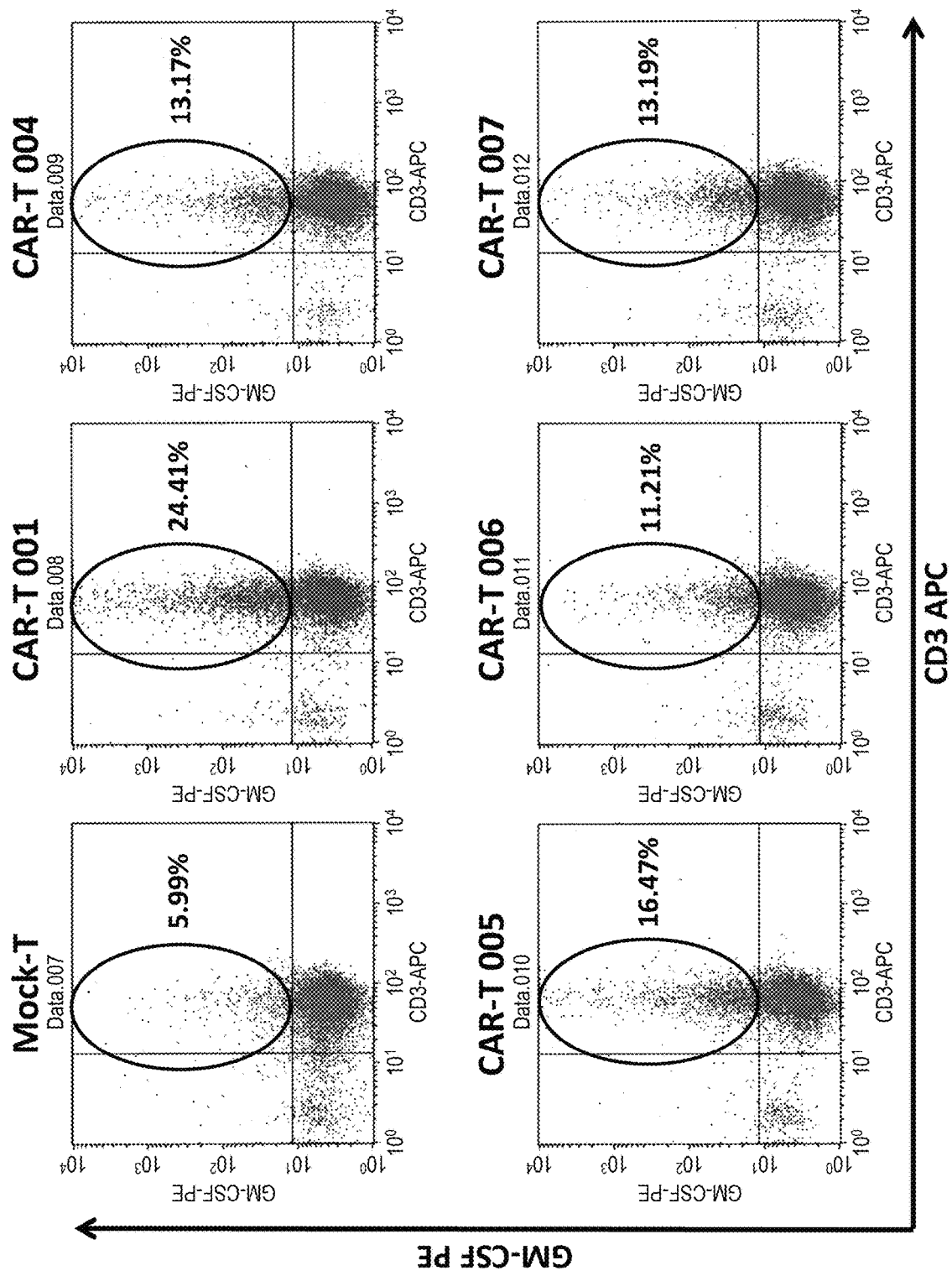
FIG. 14 shows the results of GM-CSF expression analysis on day 14 in GMR.CAR-T cells (CAR-T 001), into which a polynucleotide encoding a GMR.CAR was introduced, and in GMR.CAR-T cells (CAR-T 004 to 007) into which a polynucleotide encoding a GMR.CAR and a polynucleotide that induces RNAi were introduced.

FIG. 14 shows the results of expression analysis in CAR-T 001 and 004 to 007 on day 14 produced by the ACE method from PBMCs of a single healthy adult donor. The expression rates of GMR.CAR in CAR-T 001 and 004 to 007, which were produced by the ACE method, were as follows: CAR-T 001: 24.41%. CAR-T 004: 13.17%, CAR-T 005: 16.47%, CAR-T 006: 11.21% and CAR-T 007: 13.19, which were higher than the expression rate in the corresponding Mock-T cells (5.99%). It was confirmed that CAR-T 001 and 004 to 007 are produced by the AGE method.

Example 9 Expression Analysis of GMRα (CD116) on Tumor Cell Surface

The expression rate of GMRα (CD116) on the cell surface of tumor cell lines used in evaluation of the anti-tumor cell activity of CAR-T 001 and 004 to 007 was analyzed by flow cytometry. Acute myelogenous leukemia (AML) cell lines: THP-1, Kasumi-1, MV4-11 strains (American Type Culture Collection (ATCC)), shinAML-1 strain (a cell strain established from an AML patient in Shinshu University Hospital) or a chronic myelogenous leukemia (CML) cell strain: K562 cells were analyzed. More specifically, 1 to $2\times10^5$ cells were taken and 5 µL of APC Anti-Human CD116 antibody (Miltenyi Biotec GmbH) and 5 µL of PE Anti-Human CD33 antibody (Miltenyi Biotec GmbH) were added and suspended, and an antibody labeling reaction was carried out at 4° C. in the dark for 20 minutes. After 20 minutes, the cells were washed with an appropriate amount of D-PBS and precipitated by centrifugation. After the supernatant was removed, the cells were resuspended in an appropriate amount of D-PBS. The resuspension sample was analyzed using FACSCalibur to determine the expression rate of CD33/CD116.

The expression rate: CD33/CD116 on the surfaces of various tumor cells are shown in Table 1. CD33/CD116-positive rates in all of THP-1, Kasumi-1, shinAML-1 and MV4-11 cells were 90% or more. In contrast CD33/CD116-positive rate in K562 cells was as low as 4.29%. From this, it was confirmed that the expression of GM-CSF receptor α chain is low on the K562 cell surface.

TABLE 1

| Cell line | CD33-positive/CD116-positive rate (%) |
| --- | --- |
| THP-1 | 99.21 |
| Kasumi-1 | 94.24 |
| shinAML-1 | 98.93 |
| MV4-11 | 99.84 |
| K562 | 4.29 |

Example 10 Anti-Tumor Cell Activity of ACE CAR-T 001 and 004 to 007

To evaluate the tumor cytotoxic activity of CAR-T 001 and 004 to 007, co-culture tests with tumor cells were carried out. More specifically, THP-1, Kasumi-1, shinAML-1 or MV4-11 cells were used, and these tumor cells [target (T)] were controlled with an RPMI 1640 culture medium containing 10% FBS (Thermo Fisher Scientific K.K.) such that $5\times10^5$ cells/mL were present, and seeded in a 48-well treatment culture plate at a ratio of 500 µL/well. CAR-T 001 and 004 to 007 [effector (E)] each obtained in Example 8 were diluted with an RPMI 1640 culture medium containing 10% FBS so as to obtain an E to T ratio of 1:5 to 1:100.

More specifically, in the case where the E to T ratio=1.5, GMR.CAR-T cells were controlled such that 1×10⁵ cells/mL were present, and added to the 48-well treatment culture plate having the tumor cells seeded therein, at a ratio of 500 μL/well. Similarly, in the cases where the E to T ratio=1:50 and 1:100, GMR.CAR-T cells were controlled such that 0.1×10⁵ cells/mL and 0.05×10⁵ cells/mL were respectively present, and added to the 48-well treatment culture plate having the tumor cells second therein, at a ratio of 500 μL/well. The co-culture test was carried out for 5 days. Mock-T cells were also subjected to the same co-culture test. As a control group, tumor cells alone of the same number of cells were cultured (CAR-T non-addition group). The numbers of effector cells and target cells in a well and combinations E K to T ratio were summarized in Table 2.

TABLE 2

| Target (T) | | Number of effector (E) cells (CAR-T 001 and 004 to 007) E to T ratio | | |
|---|---|---|---|---|
| Cell line | Number of cells | 1:5 | 1:50 | 1:100 |
| THP-1 | 2.5 × 10⁵ cells | 0.5 × 10⁵ cells | 0.05 × 10⁵ cells | 0.025 × 10⁵ cells |
| Kasumi-1 | 2.5 × 10⁵ cells | 0.5 × 10⁵ cells | 0.05 × 10⁵ cells | 0.025 × 10⁵ cells |
| shinAML-1 | 2.5 × 10⁵ cells | 0.5 × 10⁵ cells | 0.05 × 10⁵ cells | 0.025 × 10⁵ cells |
| MV4-11 | 2.5 × 10⁵ cells | 0.5 × 10⁵ cells | 0.05 × 10⁵ cells | 0.025 × 10⁵ cells |

On day 5 of the co-culture test, cells were collected from individual wells and stained With trypan blue, and viable cells were counted. The cells were centrifuged and 5 μL of APC Anti-Human CD3 antibody and 5 μL of PE Anti-Human CD33 antibody were added and suspended, and an antibody labeling reaction was carried out at 4° C. in the dark for 20 minutes. After 20 minutes, the cells were washed with an appropriate amount of D-PBS and precipitated by centrifugation. After the supernatant was removed, the cells were resuspended in an appropriate amount of D-PBS. The resuspension sample was analyzed using FACSCalibur. The CD33-positive rate was determined and the anti-tumor cell activity (%) of CAR-T 001 and 004 to 007 or Mock-T cells was calculated in accordance with the following formulae.

<Calculation of Anti-Tumor Cell Activity>
Formulae:

Number of CD33-positive cells=(number of trypan blue-stained viable cells×CD33-positive rate (%) in FACS)/100

Anti-tumor cell activity (%)=100−(number of CD33-positive cells in CAR-T addition group)/(number of CD33-positive cells in CAR-T non-addition group)×100

<Calculation of Ability of CAR-T Cells to Kill Tumor Cells (Number of Tumor Cells Killed by a Single CAR-T Cell)>

Number of CAR-T cells=number of effector cells× GM-CSF-positive rate (%)/100

Number of dead cells=number of CD33-positive cells in CAR-T non-addition group−number of CD33-positive cells in CAR-T addition group Number of tumor cells killed by a single CAR-T cell=number of dead cells/number of CAR-T cells FIG. 15 shows the anti-tumor cell activity of CAR-T 001 and 004 to 007 or Mock-T cells against THP-1 cells (A) and the ability of these cells to kill tumor THP-1 cells (B). The anti-tumor cell activity of CAR-T 004 was Stranger than those of CAR-T 001, 005, 006 and 007 and 90% or more activity was retained even at an E to T ratio of 1:100. Regarding the ability to kill the tumor cells, CAR-T 004 was the strongest, and about twice us strong as the ability of CAR-T 001 into which an shRNA was not introduced or CAR-T 007 (negative control).

Figure 16:
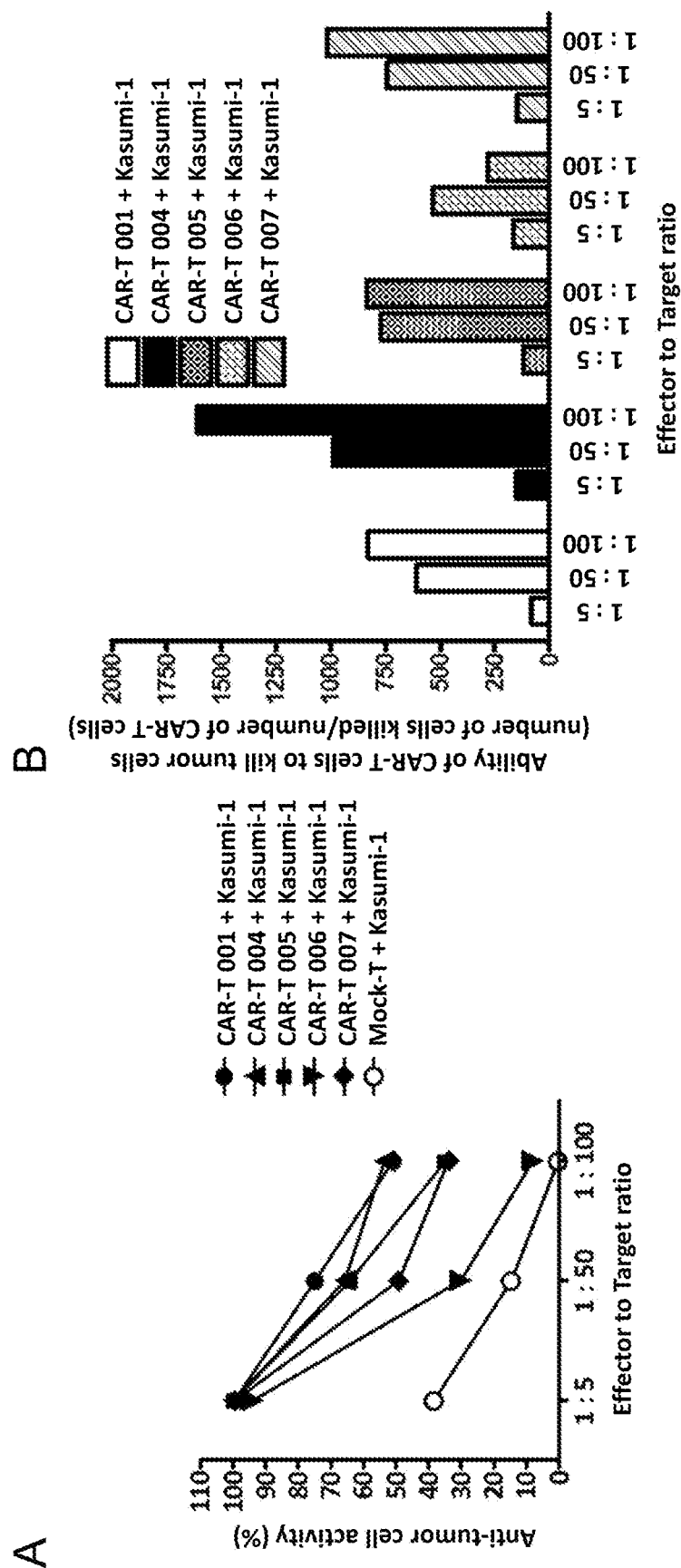
FIG. 16 shows the antitumor-cell activity (%) of CAR-T 001, CAR-T 004 to CAR-T 007 and Mock-T cells against Kasumi-1 cells (A) and the ability of these cells to kill tumor Kasumi-1 cells (B).

FIG. 16 shows the anti-tumor cell activity of CAR-T 001 and 004 to 007 or Mock-T cells against Kasumi-1 cells (A) and the ability of these cells to kill tumor Kasumi-1 cells (B). Regarding the ability to kill the tumor cells, CAR-T 004 was the strongest, and about 1.5 times as strong as the ability of CAR-T 001 into which an shRNA was not introduced or CAR-T 007 (negative control).

FIG. 17 shows the anti-tumor cell activity of CAR-T 001 and 004 to 007 or Mock-T cells against shinAML-1 cells (A) and the ability of these cells to kill tumor shinAML-1 cells (B). The anti-tumor cell activity of CAR-T 004 was stronger than those of CAR-T 001, 005, 006 and 007 and 80% or more activity was retained even at an E to T ratio of 1:100. Regarding the ability to kill tumor cells, CAR-T 004 was the strongest, and twice or more as strong as the ability of CAR-T 001 into which an shRNA was not introduced 01 CAR-T 007 (negative control).

FIG. 18 shows the anti-tumor cell activity of CAR-T 001 and 004 to 007 or Mock-T cells against MV4-11 cells (A) and the ability of these cells to kill tumor MV4-11 cells (B). The anti-tumor cell activity of CAR-T 004 was stronger than those of CAR-T 001, 005, 006 and 007 and 70% or more activity was retained even at an E to T ratio of 1:100. Regarding the ability to kill tumor cells. CAR-T 004 was the strongest, and about 1.5 times as strong as the ability of CAR-T 001 into which an shRNA was not introduced or CAR-T 007 (negative control).

Example 11 Evaluation of Secretion Level of GM-CSF

The culture supernatant in the co-culture test carried out in Example 10 at an E to T ratio of 1:5 was taken from day 1 to day 5, and cryopreserved at −30° C. until use for measurement. After the culture supernatant cryopreserved was thawed and diluted 10 fold with D-PBS, the secretion level of GM-CSF in the culture supernatant was measured using Human GM-CSF Quantikine ELISA Kit (R&D Systems, Inc.). The amounts of secreted GM-CSF from CAR-T 001 and 004 to 007 were corrected based on GM-CSF-positive rate (%) of CAR-T cells.

Figure 19:
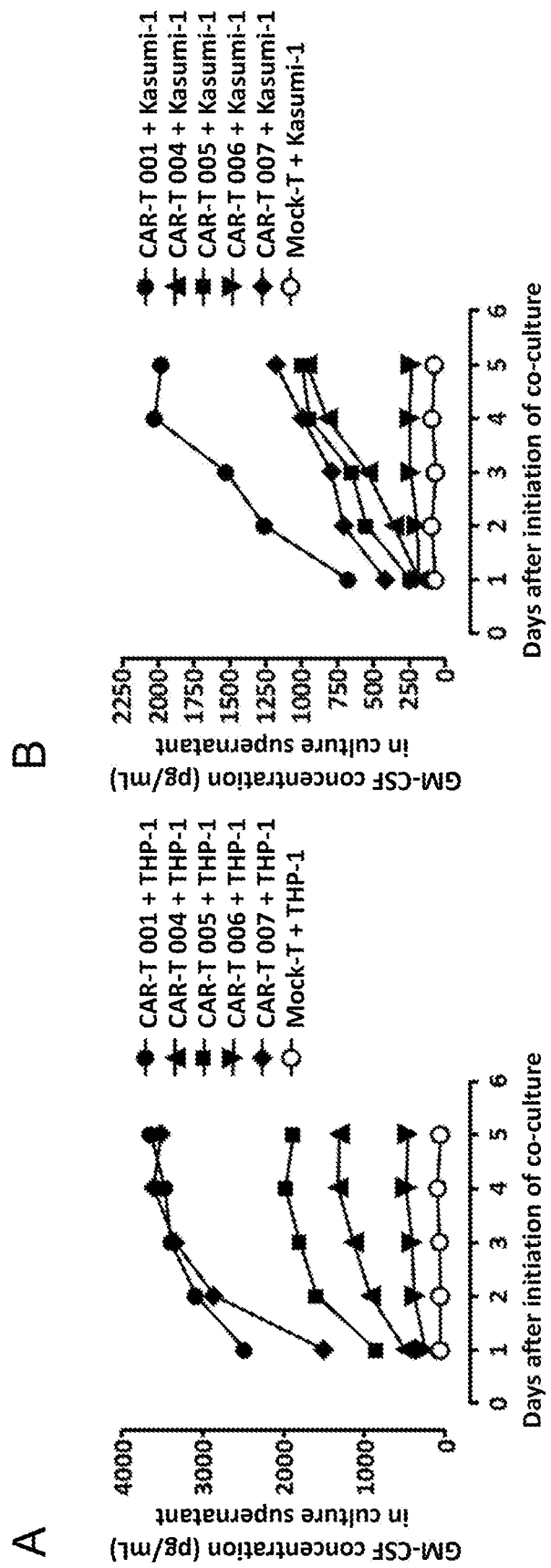
FIG. 19 shows the time-dependent change of GM-CSF concentration in the supernatant of the co-culture of any one of CAR-T 001, CAR-T 004 to CAR-T 007 and Mock-T cells, and THP-1 (A) or Kasumi-1 cells (B).

FIGS. 19 and 20 show the measurement results of GM-CSF concentration in the supernatant of the co-culture of any one of CAR-T 001 and 004 to 007 with THP-1, Kasumi-1, shinAML-1 or MV4-11 cells. In the co-culture of CAR-T 001, into which an shRNA was not introduced, with any one of the tumor cells, an increase in the amount of secreted GM-CSF was observed. In contrast, in the co-culture of CAR-T 004, 005 and 006, into which an shRNA to the untranslated region of GM-CSF was inserted, with any one of the tumor cells, the amount of secreted GM-CSF decreased compared to that of CAR-T 001, indicating GM-CSF knockdown effect in the case where any one of shRNAs of SEQ ID NOs: 29 to 31 was used. However, such a knockdown effect was rarely observed in CAR-T 007 into which a negative control shRNA was introduced.

The CAR-T cell where the GM-CSF knockdown effect is most strongly correlated with an increase in the anti-tumor cell activity of CAR-T cells was CAR-T 004. CAR-T 006 where the GM-CSF knockdown effect is considered to be the strongest is inferior in anti-tumor cell activity to any one of other CAR-T cells, suggesting the possibility that secretion of the cytokine itself decreases with tumor cell killing, rather than the possibility of higher knockdown effect by an siRNA.

Example 12 Production of GMR.CAR Spacer-Modified Expression Plasmids (CAR 008 to 011)

Figure 21:
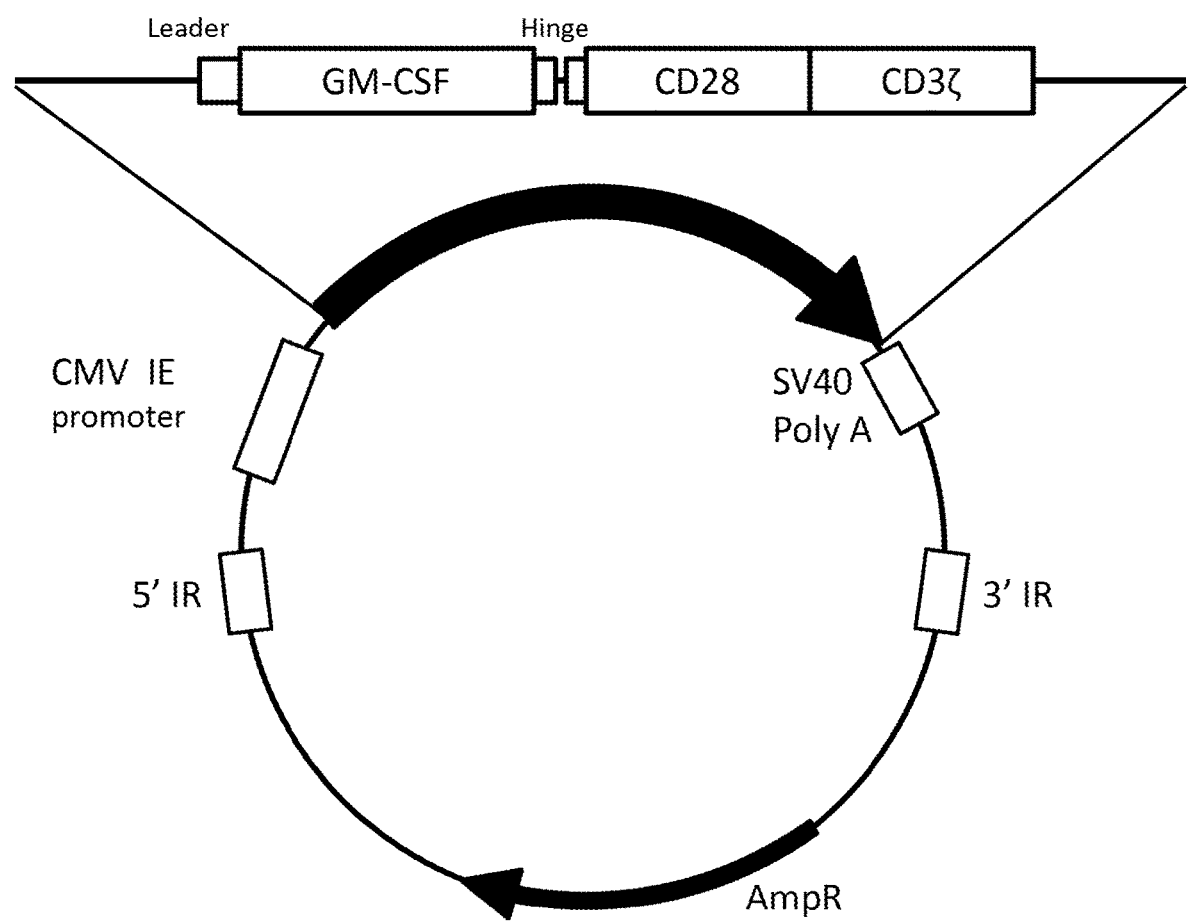
FIG. 21 shows an example of a vector map of a GMR.CAR of the present invention having a modified spacer domain (vector having a CH2CH3 deletion: GMR.CARdCH2CH3).
Figure 22:
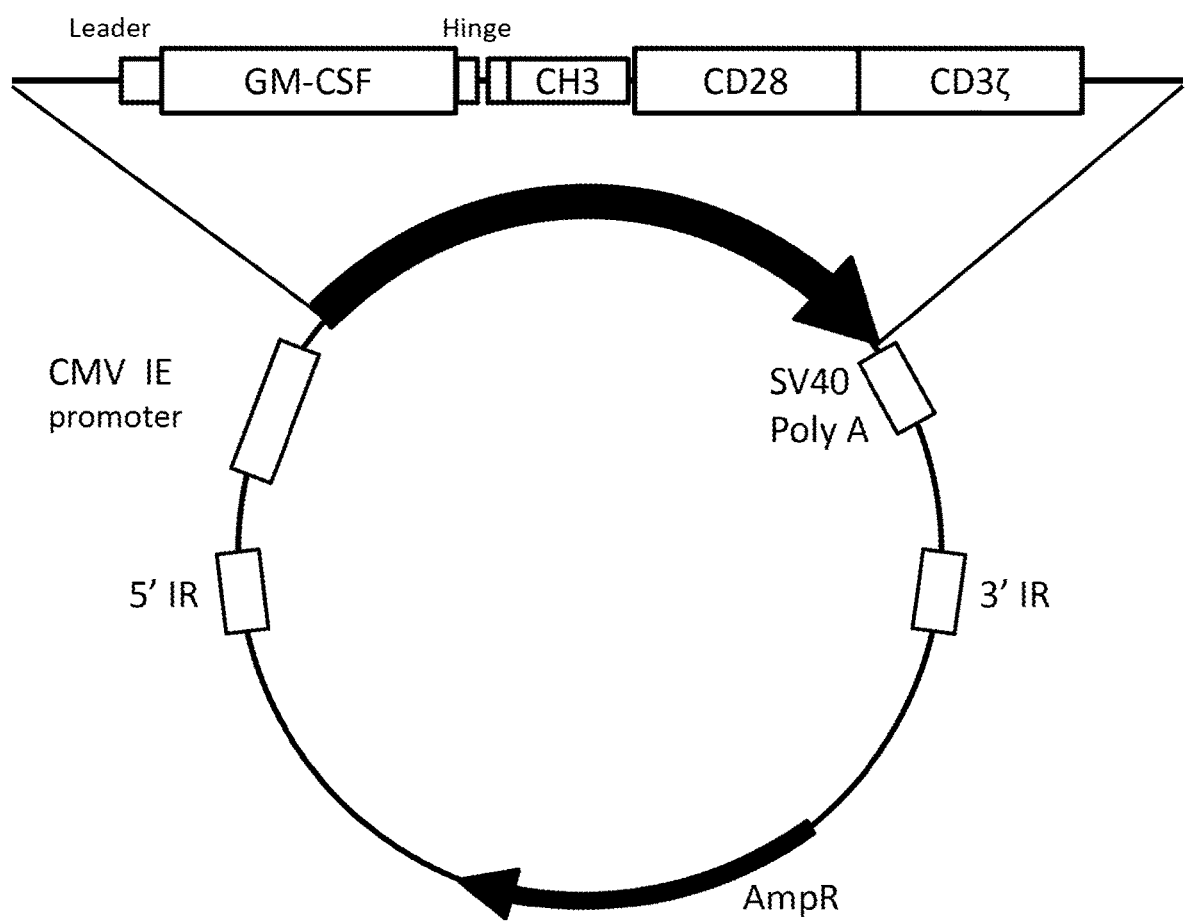
FIG. 22 shows an example of a vector map of a GMR.CAR of the present invention having a modified spacer domain (vector having a CH2 deletion: GMR.CARdCH2).
Figure 23:
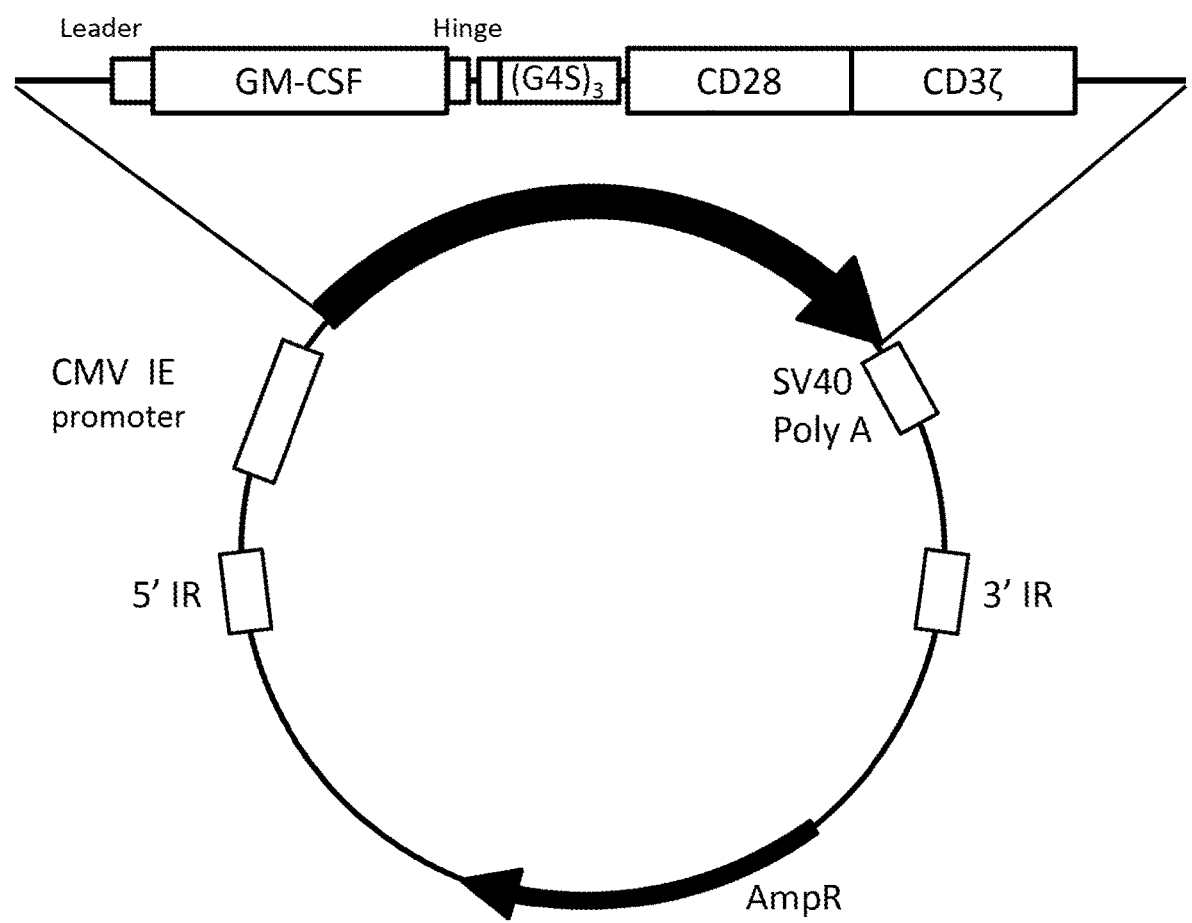
FIG. 23 shows an example of a vector map of a GMR.CAR of the present invention having a modified spacer domain (vector having a CH2CH3 deletion and a (G4S)3 insert: GMR.CARdCH2CH3+)G4S)3).
Figure 24:
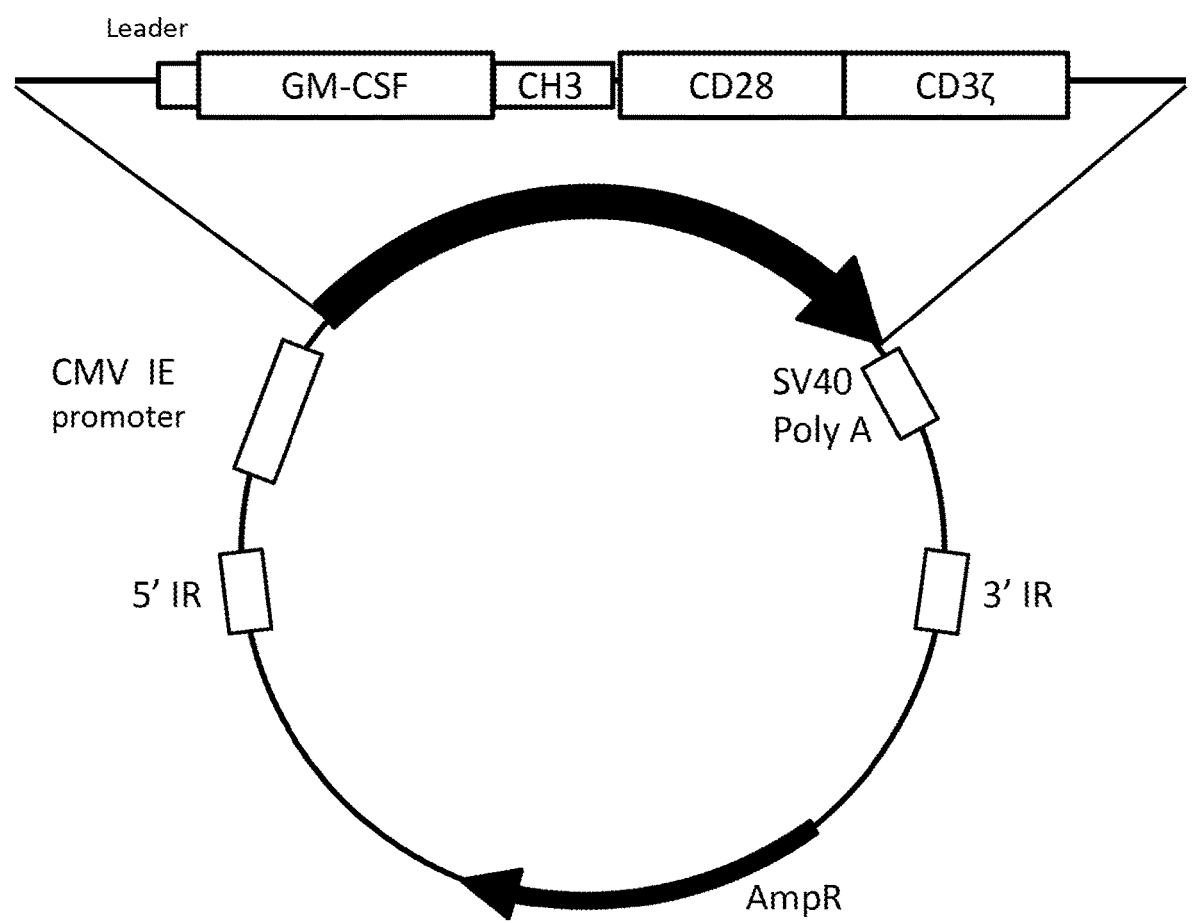
FIG. 24 shows an example of a vector map of a GMR.CAR of the present invention having a modified spacer domain (vector having a hinge-CH2 deletion: GMR.CAR-dhingeCH2).

GMR.CAR expression plasmids each having a modified extracellular spacer domain were produced using CAR 001 as a template, in accordance with the inverse-PCR method. More specifically, a plasmid having a partial deletion of CH2CH3 (FIG. 21), a plasmid having a partial deletion of CH2 (FIG. 22), a plasmid having a partial deletion of CH2CH3 and an insert of (G4S)3 (FIG. 23), and a plasmid having a partial deletion of hinge and CH2 (FIG. 24) were produced, vector maps of which are separately shown in FIGS. 21 to 24.

PCR primers to be used for the inverse-PCR are shown below: primers for a partial deletion of CH2CH3 (SEQ ID NOs: 33 and 34), primers for a partial deletion of CH2 (SEQ ID NOs: 35 and 36), primers for a partial deletion of CH2CH3 and an insert of (G4S)3 (SEQ ID NOs: 37 and 38) and primers for a partial deletion of hinge and CH2 (SEQ ID NOs: 39 and 40), were separately designed and synthesized (outsourced to Eurofins Genomics K.K.).

```
<Primers for a partial deletion of CH2CH3>
Forward primer:
                                         (SEQ ID NO: 33)
5'-TTTTGGGTGCTGGTGGTGGTTGGTGGAGTC-3'

Reverse primer:
                                         (SEQ ID NO: 34)
5'-TGGGCATGTGTGAGTTTTGTCAGGAGAT-3'

<Primers for a partial deletion of CH2>
Forward primer:
                                         (SEQ ID NO: 35)
5'-GGGCAGCCCCGAGAACCACAGGTGTAC-3'

Reverse primer:
                                         (SEQ ID NO: 36)
5'-TGGGCATGTGTGAGTTTTGTCAGGAGATTTGGGC-3'

<Primers for a partial deletion of CH2CH3 and an
insert of (G4S)3>
Forward primer:
                                         (SEQ ID NO: 37)
5'-GGTGGTGGTGGATCCGGCGGCGGCGGCTCCGGTGGTGGTGGTTCTAA

AGATCCCAAATTTTGGGTGCTGG-3'

Reverse primer:
                                         (SEQ ID NO: 38)
5'-TGGGCATGTGTGAGTTTTGTCAGGAGATTTGGG-3'

<Primers for a partial deletion of hinge and CH2>
Forward primer:
                                         (SEQ ID NO: 39)
5'-GGGCAGCCCCGAGAACCACAGGTGTAC-3'

Reverse primer:
                                         (SEQ ID NO: 40)
5'-CTCCTGGACTGGCTCCCAGCAGTC-3'
```

CAR 001 was prepared at 50 ng/μL and used as a template. Individual PCR primers were prepared to be 0.2 or 0.3 μM in a reaction solution. Inverse-PCR was carried out using KOD-Plus-Mutagenesis Kit (Toyobo Co., Ltd.), and the reaction composition was prepared in accordance with the protocol attached to the kit. The reaction conditions were as follows: (i) 94° C., 2 minutes, (ii) 98° C., 10 seconds, and (iii) 68° C., 7 minutes; and a cycle of (ii) and (iii) was repeated 10 times.

After PCR, an aliquot was taken from the sample and subjected to 1 to 1.2% agarose gel electrophoresis and separated. In this manner, the production of a linear plasmid having a desired size was confirmed. Then, the rest of the sample after PCR was subjected to a treatment with Dpn I in accordance with the protocol attached to the kit. With the treatment, a reaction for cutting and eliminating methylated template plasmid CAR 001 was carried out. Thereafter, the linear plasmid was allowed to self-ligate with T4 Polynucleotide Kinase in the kit to form a circular plasmid. *Escherichia coli* DH5α (Toyobo Co., Ltd.) was transformed with each circular plasmid obtained and cultured on an LB agar medium containing 50 μg/mL ampicillin for about 16 hours.

Colonies emerged were further cultured in an LB liquid medium containing 50 μg/mL ampicillin for about 16 hours. Each plasmid was purified from the *Escherichia coli* culture solution using QIAprep Spin Miniprep Kit (QIAGEN K.K.) and sequenced. In this manner, plasmids, which were confirmed to have a desired nucleotide sequence modification, more specifically, CAR 008 (GMR.CAR dCH2CH3), CAR 009 (GMR.CAR dCH2, CAR 010 (GMR.CAR dCH2CH3+ (G4S)3) and CAR 011 (GMR.CAR dHingeCH2) were obtained. Regarding the extracellular spacer domains of the obtained plasmids, the extracellular spacer domain of CAR 008 contains a hinge region consisting of the amino acid sequence of SEQ ID NO: 6; the extracellular spacer domain of CAR 009 contains a hinge region consisting of the amino acid sequence of SEQ ID NO: 6 and a CH3 region consisting of the amino acid sequence of SEQ ID NO: 10; the extracellular spacer domain of CAR 010 contains a hinge region consisting of the amino acid sequence of SEQ ID NO: 6 and a (G4S)3 sequence consisting of SEQ ID NO: 42; and the extracellular spacer domain of CAR011 contains a CH3 region consisting of the amino acid sequence of SEQ ID NO: 10.

Example 13 Production of GMR.CAR+shRNA Insert Spacer Modified Expression Plasmids (CAR 012 to 015)

GMR.CAR expression plasmids each having a modified extracellular spacer domain were produced using CAR 004 as a template in accordance with the inverse-PCR method in the same manner as in Example 12.

The primers and method used in this Example were the same as those used in Example 12, and plasmids: CAR 012 (GMR.CAR+shRNA dCH2CH3, CAR 013 (GMR.CAR+shRNA dCH2), CAR 014 (GMR.CAR+shRNA dCH2CH3+(G4S)3) and CAR 015 (GMR.CAR+shRNA dHingeCH2) were obtained, which were confirmed to have a desired nucleotide sequence modification by sequencing. The extracellular spacer domains of the obtained plasmids CAR 012, CAR 013, CAR 014 and CAR 015 have the same structures as in CAR 008, CAR 009, CAR 010 and CAR 011, respectively, and these plasmids each further contain an shRNA (FIG. 4, SEQ ID NO: 29) complementary to the sequence of the 5' side untranslated region of GM-CSF, as with CAR 004.

Example 14 Culture/Amplification of GMR.CAR-T Cells (CAR-T 008 to 011, CAR-T 012 and CAR-T 014)_3

<Day 0: Isolation of PBMCs and Production of Nonspecific Stimulation OKT 3 Blast>

Peripheral blood was taken from a healthy adult donor, diluted by a factor of 2 with D-PBS (Wako Pure Chemical Industries. Ltd.), and then overlayered on Ficoll-Paque PLUS and centrifuged at 400×g for 30 minutes to collect PBMCs. The collected PBMCs were washed twice with D-PBS and isolated by centrifugation. The isolated PBMCs were suspended in TexMACS medium supplemented with 5 ng/mL IL-15 such that 2 to $4 \times 10^6$ cells/well/2 mL were present. A 24-well non-treatment culture plate was treated with D-PBS containing an anti-CD3 antibody and an anti-CD28 antibody at 37° C. for 2 hours. In this manner, the plate was coated with the antibodies. The cell suspension was supplied at a ratio of 2 L/well to carry out specific stimulation of T cells to produce OKT3 blast.

<Day 0: Viral Peptide Pulse to PBMCs>

The isolated PBMCs were subjected to viral peptide stimulation using PepTivator® peptide pool (Miltenyi Biotec GmbH). More specifically, the PBMCs were suspended in the peptide pool, in which AdV5 Hexon, CMV pp65, EBV BZLF1 and EBV EBNA-1 each having a concentration of 0.05 μg/μL were added in D-PBS (50 μL), and subjected to viral peptide stimulation at 37° C. for 30 minutes. The culture method of this Example was defined as PBMC-ACE method, a modified method of the ACE method described in Example 8. After 30 minutes, an appropriate amount of D-PBS was added to the PBMCs and suspended. Thereafter, UV irradiation was applied for 4 minutes. The UV-irradiated PBMCs were collected and counted, the cells were then suspended in TexMACS medium supplemented with 10 ng/mL IL-7 and 5 ng/mL IL-15 such that 0.5 to $2 \times 10^6$ cells/well/2 mL were present, and transferred to a 24-well treatment culture plate as feeder cells.

<Day 0: Isolation of PBMCs and Gen Introduction Operation>

Peripheral blood was taken from a healthy adult donor, diluted by a factor of 2 with D-PBS (Wako Pure Chemical Industries, Ltd.), and then overlayered on Ficoll-Paque PLUS (GE Healthcare) and centrifuged at 400×g for 30 minutes to collect PBMCs. The collected PBMCs were washed twice with D-PBS and isolated by centrifugation. $10 \times 10^6$ cells were used for introduction of a GMR.CAR expression plasmid into PBMCs. More specifically, any one of CAR 008 to 011, CAR 012 and CAR 014 (5 μg), pCMV-piggyBac plasmid (5 μg) and P3 Primary Cell solution (100 μL) in P3 Primary Cell 4D-Nucleofector™ X Kit (Lonza Japan Ltd.) were mixed, and $10 \times 10^6$ PMBCs were suspended. The total amount of the suspended cells was transferred to Nucleocuvette and electrical gene introduction was carried out by 4D-Nucleofection (Program No: FI-115). The cells to which electrical gene introduction was applied were allowed to stand still at room temperature for 10 minutes. The total amount of the cells was transferred to the 24-well treatment culture plate containing feeder cells and culture was initiated. $1 \times 10^6$ Mock-T cells, to which gen introduction operation was not applied, were cultured in the same manner. Medium exchange was appropriately carried out by discarding a half amount of the culture medium and adding a half amount of TexMACS medium supplemented with 20 ng/mL IL-7 and 10 ng/mL IL-15 (double concentration). Mock-T cells not subjected to gene introductions were continuously cultured on a 24-well treatment culture plate, and medium exchange and amplification were carried out depending on the cell proliferation rate.

<Day 7: Amplification of CAR-T Cells>

The total amount of the cell suspension was transferred to G-Rex 10 filled with TexMACS medium (30 mL) supplemented with 10 ng/mL IL-7 and 5 ng/mL IL-15 and containing $2 \times 10^6$ feeder cells produced in the same manner as in the operation on day 0. GMR.CAR-T cells were then amplified until day 14. The expression rate of GMR.CAR-T cells amplified until day 14 was determined by the following method.

<Day 14: Evaluation of GMR.CAR Expression Rate>

Cells were counted and 1 to $2 \times 10^5$ cells were subjected to flow cytometric analysis to evaluate the expression rate of a GMR.CAR-T. 1 to $2 \times 10^5$ cells were taken and centrifuged. To the centrifuged cells, 5 μL of PE Rat Anti-Human GM-CSF antibody (Miltenyi Biotec GmbH) and 5 μL of APC Anti-Human CD3 antibody were added and suspended, and an antibody labeling reaction was carried out at 4° C. in the dark for 20 minutes. After 20 minutes, the cells were washed with an appropriate amount of D-PBS and precipitated by centrifugation. After the supernatant was removed, the cells were resuspended in an appropriate amount of D-PBS. The resuspension sample was analyzed using FACSCantoII (BD) and FLOWJO (Tomy Digital Biology Co., Ltd.) to determine the expression rate of a GM-CSF/CD3-positive GMR.CAR. GMR.CAR-T cells obtained by subjecting the produced expression plasmids (CAR 008 to 011, CAR 012 and CAR 014) to electrical introduction operation into PBMCs and T cell culture/amplification operation were defined as CAR-T 008, CAR-T 009, CAR-T 010, CAR-T 011, CAR-T 012 and CAR-T 014, respectively.

Figure 25:
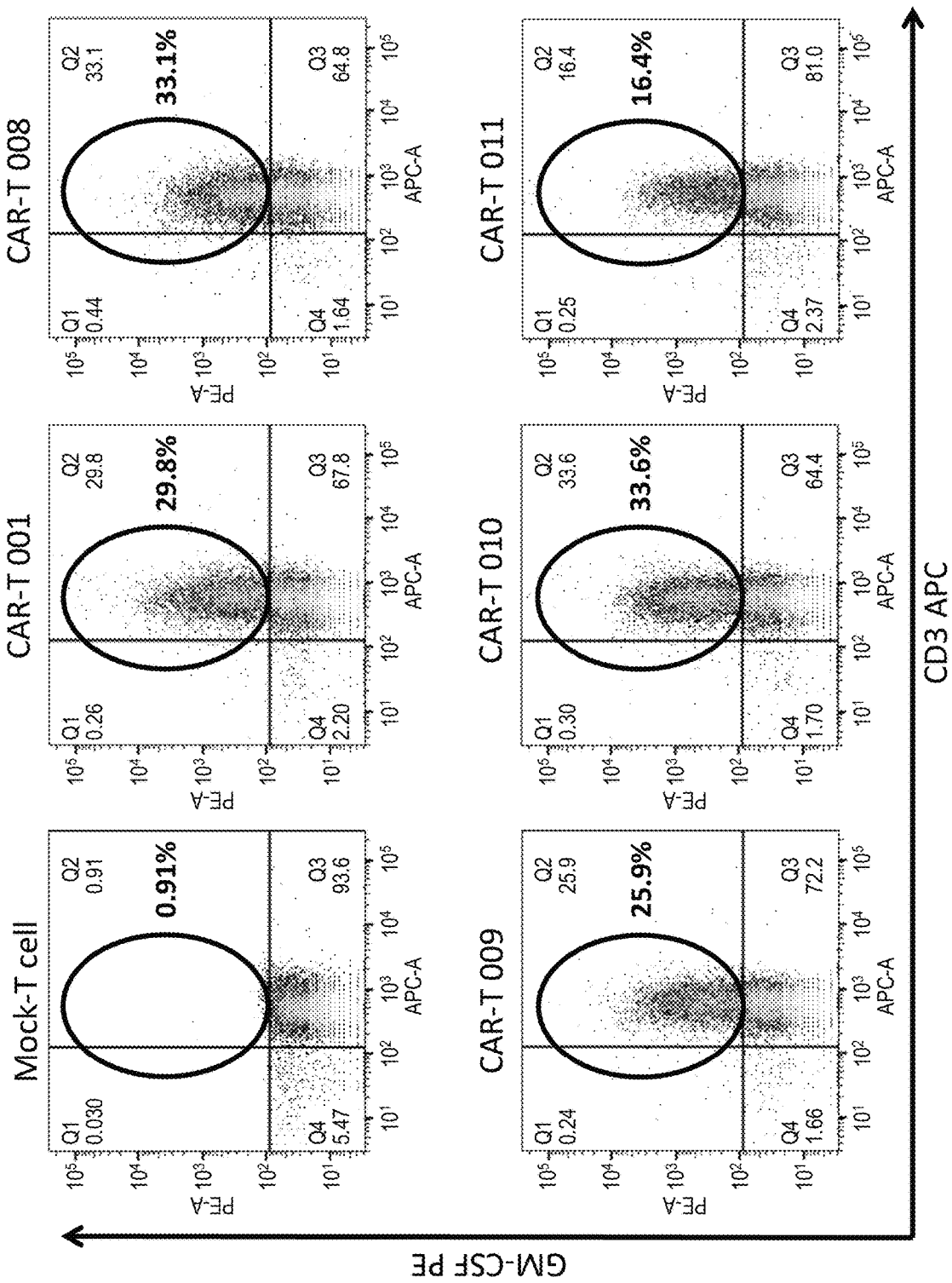
FIG. 25 shows the analysis results of GM-CSF expression on day 14 in GMR.CAR-T cells (CAR-T 001, CAR-T 008 to 011) into which a polynucleotide encoding GMR.CAR was introduced.

FIG. 25 shows the results of expression analysis in CAR-T 001 and 008 to 011 on day 14. The expression rates of GMR.CARs were as follows: CAR-T 001: 29.8%, CAR-T 008: 33.1%. CAR-T 009: 25.9%, CAR-T 010:33.6% and CAR-T 011: 16.4%, which were all higher than the expression rate (0.91%) in Mock-T cells, and GMR.CAR-expressing T cells having different spacer sites were successfully produced. In the subsequent experiments, the produced GMR.CAR-expressing T cells were diluted with Mock-T cells to control the expression rates of them to be 25.9% (the expression rate of CAR-T 011 kept equal to 16.4%) and subjected to evaluation of anti-tumor cell activity.

Figure 26:
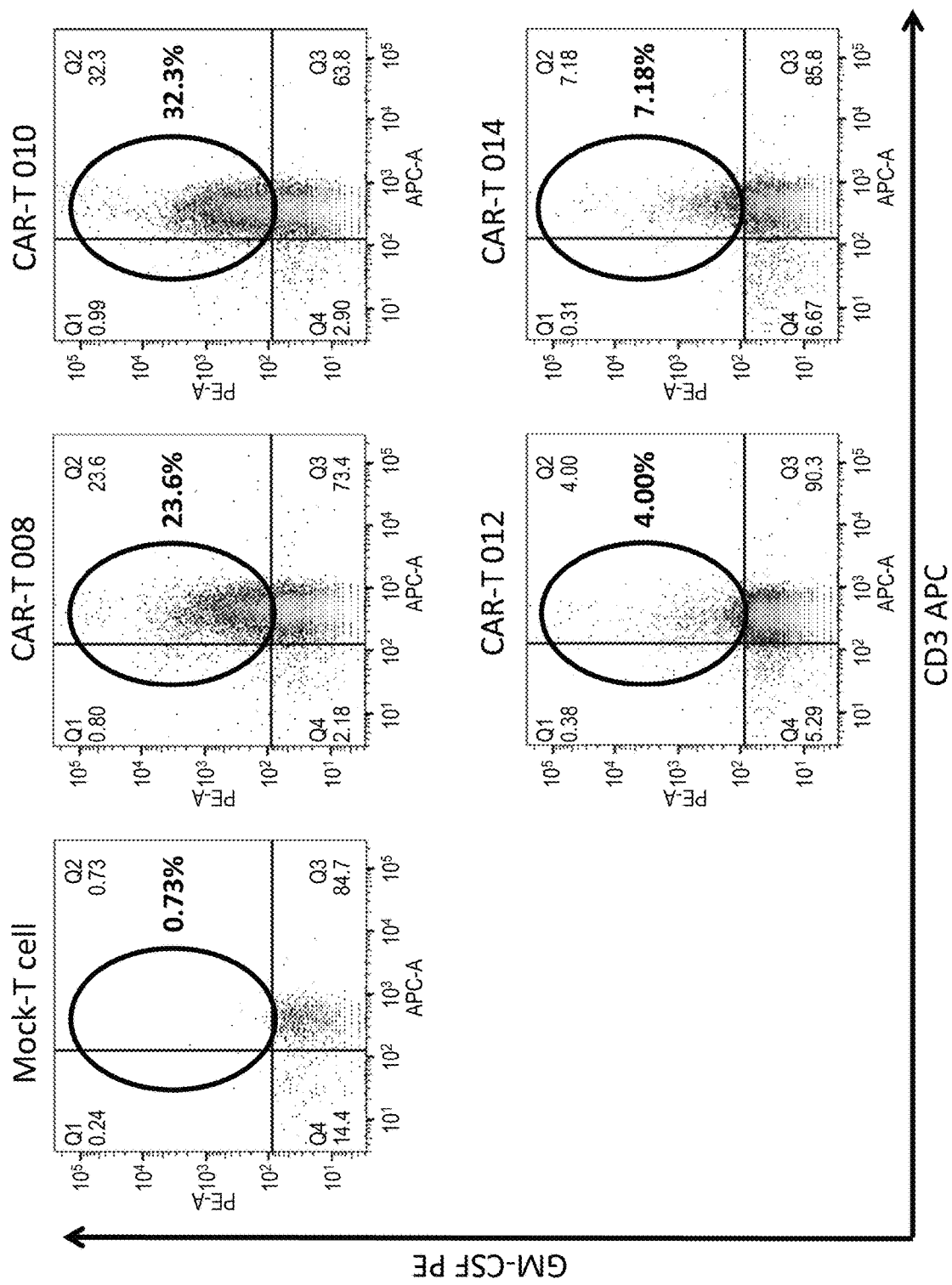
FIG. 26 shows the results of GM-CSF expression analysis on day 14 in GMR.CAR-T cells (CAR-T 008, CAR-T 010, CAR-T 012 and CAR-T 014) into which a polynucleotide encoding a GMR.CAR was introduced.

The analysis results of expression of CAR-T 008, CAR-T 010, CAR-T 012 and CAR-T 014 on day 14 are shown in FIG. 26. The expression rates of GMR.CARs were as follows: CAR-T008: 23.6%, CAR-T010: 32.3%, CAR-T012: 4.00% and CAR-T014: 7.18%.

Example 15 Evaluation of Anti-Tumor Cell Activity of CAR-T 008 to 011

To evaluate the tumor cytotoxic activity of CAR-T 001 and 008 to 011 obtained in Example 14, co-culture tests with tumor cells were carried out. More specifically, MV4-11 cells (American Type Culture Collection (ATCC)) were used. The MV4-11 cells [target (T)] were controlled with an RPMI 1640 culture Medium containing 10% FBS (Thermo Fisher Scientific K.K.) such that $5 \times 10^5$ cells/mL were present, and seeded in a 48-well treatment culture plate at a ratio of 500 μL/well (the number of cells per well is $2.5 \times 10^5$). CAR-T 001 and 008 to 011 [effector (E)] were diluted with an RPMI 1640 culture medium containing 10% FBS so as to obtain an E to T ratio of 1:25 and 1:125. More specifically, in the case of the E to T ratio of 1:25, CAR-T was controlled such that $0.2 \times 10^5$ cells/mL were present and added to the 48-well treatment culture plate having the tumor cells seeded therein, at a ratio of 500 µL/well (the number of cells per well is $0.1 \times 10^5$). Similarly, in the case of the E to T ratio of 1:125, CAR-T was controlled such dial $0.04 \times 10^5$ cells/mL were present, and added to the 48-well treatment culture plate having the tumor cells seeded therein, at a ratio of 500 µL/well (the number of cells per well is $0.02 \times 10^5$).

The co-culture test was carried out for 5 days. The same co-culture test was carried out for Mock-T cells not subjected to gene introduction. As a control group, tumor cells alone of the same number of cells were cultured (CAR-T non-addition group). On day 5 of the co-culture test, cells were collected from individual wells and centrifuged. To the centrifuged cells, 5 µL of APC Anti-Human CD3 antibody (Miltenyi Biotec GmbH) and 5 µL of PE Anti-Human CD33 antibody (Miltenyi Biotec GmbH) were added and suspended, and an antibody labeling reaction was carried out at 4° C. in the dark for 20 minutes. After 20 minutes, the cells were washed with an appropriate amount of D-PBS and precipitated by centrifugation. After the supernatant was completely removed, the cells were resuspended in 450 µL of D-PBS. 50 µL of CountBright absolute counting beads (Invitrogen) were then further added to prepare a sample. The sample was analyzed using FACS Canto II (BD) and FLOWJO (Tomy Digital Biology Co., Ltd.). The number of CD33-positive cells was calculated based on the count number of beads. The anti-tumor cell activities (%) of CAR-T 001, 008 to 011 and a Mock-T cell were calculated in the same manner as in Example 10.

Figure 27:
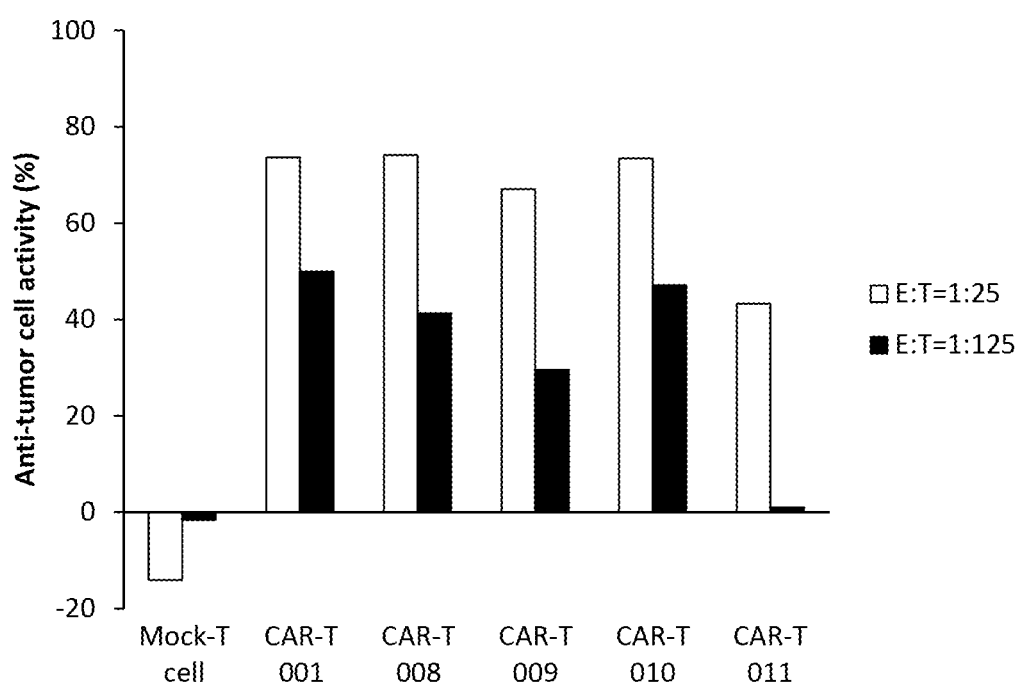
FIG. 27 shows the antitumor-cell activity (%) of CAR-T001, CAR-T 008 to CAR-T 011 and Mock-T cells against MV4-11 cells.

The results of the anti-tumor cell activity (%) of the produced CAR-T 001 and 008 to 011 against MV4-11 cells were shown in FIG. 27. Data were average values of anti-tumor cell activities (%) of three wells of the same donor CAR-T. It was confirmed that CAR-T 001 and 008 to 011 have strong anti-tumor cell activities against MV4-11 cells at an E to T ratio of 1:25. At an E to T ratio of 1:125, it was recognized that the anti-tumor cell activity-varies depending on the types of spacers.

Example 16 Evaluation of Anti-Tumor Cell Activity of CAR-T 012 and CAR-T 014

To evaluate the tumor cytotoxic activity of CAR-T 012 and 014 obtained in Example 14, co-culture tests with tumor cells were carried out. More specifically, MV4-11 cells (American Type Culture Collection (ATCC)) were used. The MV4-11 cells [target (T)] were controlled with an RPMI 1640 culture medium containing 10% FBS (Thermo Fisher Scientific K.K.) such that $5 \times 10^5$ cells/mL were present, and seeded in 48-well treatment culture plate at a ratio of 500 µL/well (the number of cells per well is $2.5 \times 10^5$). CAR-T 012 and 014 [effector (E)] were diluted with an RPMI 1640 culture medium containing 10% FBS so as to obtain an E to T ratio of 1:5, 1:25 and 1:125. More specifically, in the case of the E to T ratio of 1:5, CAR-T was controlled such that $1 \times 10^5$ cells/mL were present, and added to the 48-well treatment culture plate having the tumor cells seeded therein, at a ratio of 500 µL/well (the number of cells per well is $0.5 \times 10^5$). Also, in the case of the E to T ratio of 1:25, CAR-T was controlled such that $0.2 \times 10^5$ cells/mL were present, and added to the 48-well treatment culture plate having the tumor cells seeded therein, at a ratio of 500 µL/well (the number of cells per well is $0.1 \times 10^5$). Similarly, in the case of the E to T ratio of 1:125, CAR-T was controlled such that $0.04 \times 10^5$ cells/mL were present, and added to the 48-well treatment culture plate having the tumor cells seeded therein, at a ratio of 500 µL/well (the number of cells per well is $0.02 \times 10^5$).

The co-culture test was carried out for 4 days. The same co-culture test was also carried out for Mock-T cells not subjected to gene introduction. As a control group, tumor cells alone of the same number of cells were cultured (CAR-T non-addition group). On day 4 of the co-culture test, the cells were collected from individual wells and centrifuged. To the centrifuged cells, 5 µL of APC Anti-Human CD3 antibody (Miltenyi Biotec GmbH) and 5 µL of PE Anti-Human CD33 antibody (Miltenyi Biotec GmbH) were added and suspended, and an antibody labeling reaction was carried out at 4° C. in the dark for 20 minutes. After 20 minutes, the cells were washed with an appropriate amount of D-PBS and precipitated by centrifugation. After the supernatant was completely removed, the cells were resuspended in 450 µL of D-PBS. 50 µL of CountBright absolute counting beads (Invitrogen) were then further added to prepare a sample. The sample was analyzed using FACS Canto II (BD) and FLOWJO (Tomy Digital Biology Co., Ltd.). The number of CD33-positive cells was calculated based on the count number of beads. The anti-tumor cell activities (%) of CAR-T 00X to 00Y and Mock-T cells were calculated in the same manner as in Example 10, based on the number of CD33-positive cells calculated.

Figure 28:
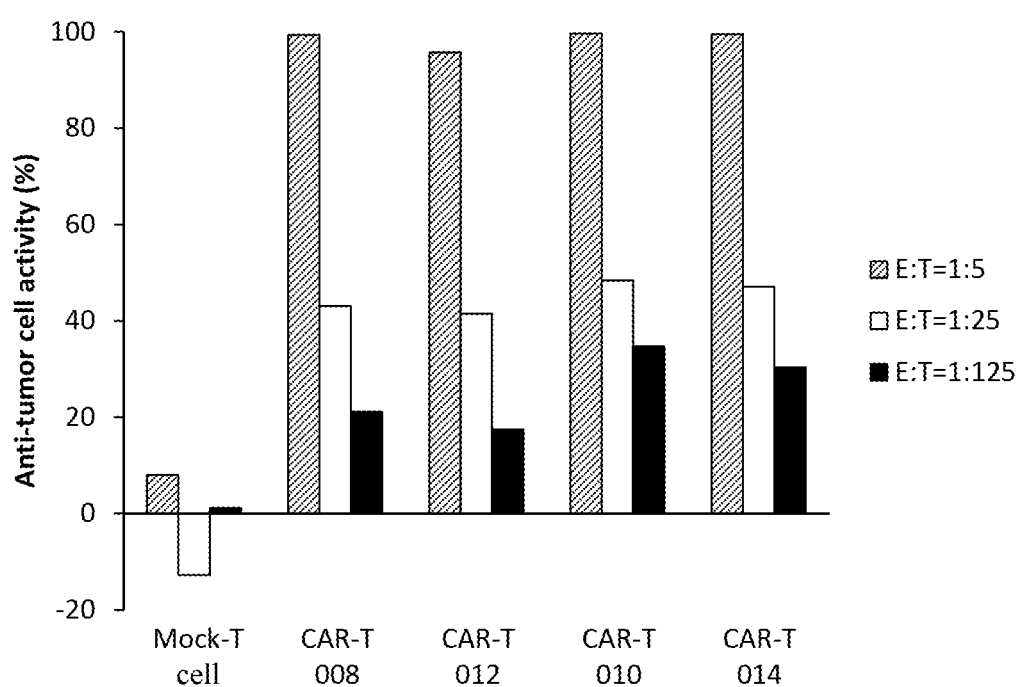
FIG. 28 shows the antitumor-cell activity (%) of CAR-T 012, CAR-T 014 and Mock-T cells against MV4-11 cells.

The results of the anti-tumor cell activity (%) of the produced CAR-T 012 and 014 against MV4-11 cells were shown in FIG. 28, together with the results of those of CAR-T 008 and 010. It was confirmed that CAR-T 012 and 014 have strong anti-tumor cell activity against MV4-11 cells at an E to T ratio of 1:5 and have stronger anti-tumor cell activity than Mock-T cells even at an E to T ratio of 1:25 and 1:125.

Figure 29:
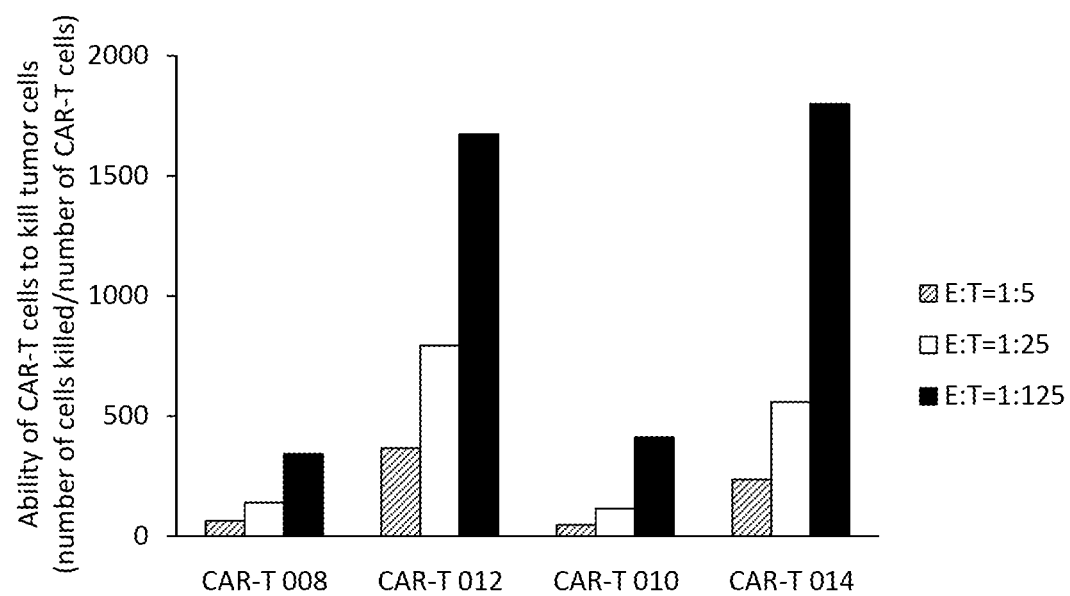
FIG. 29 shows the ability of CAR-T 012, CAR-T 014 and Mock-T cells to kill tumor MV4-11 cells.
Figure 32:
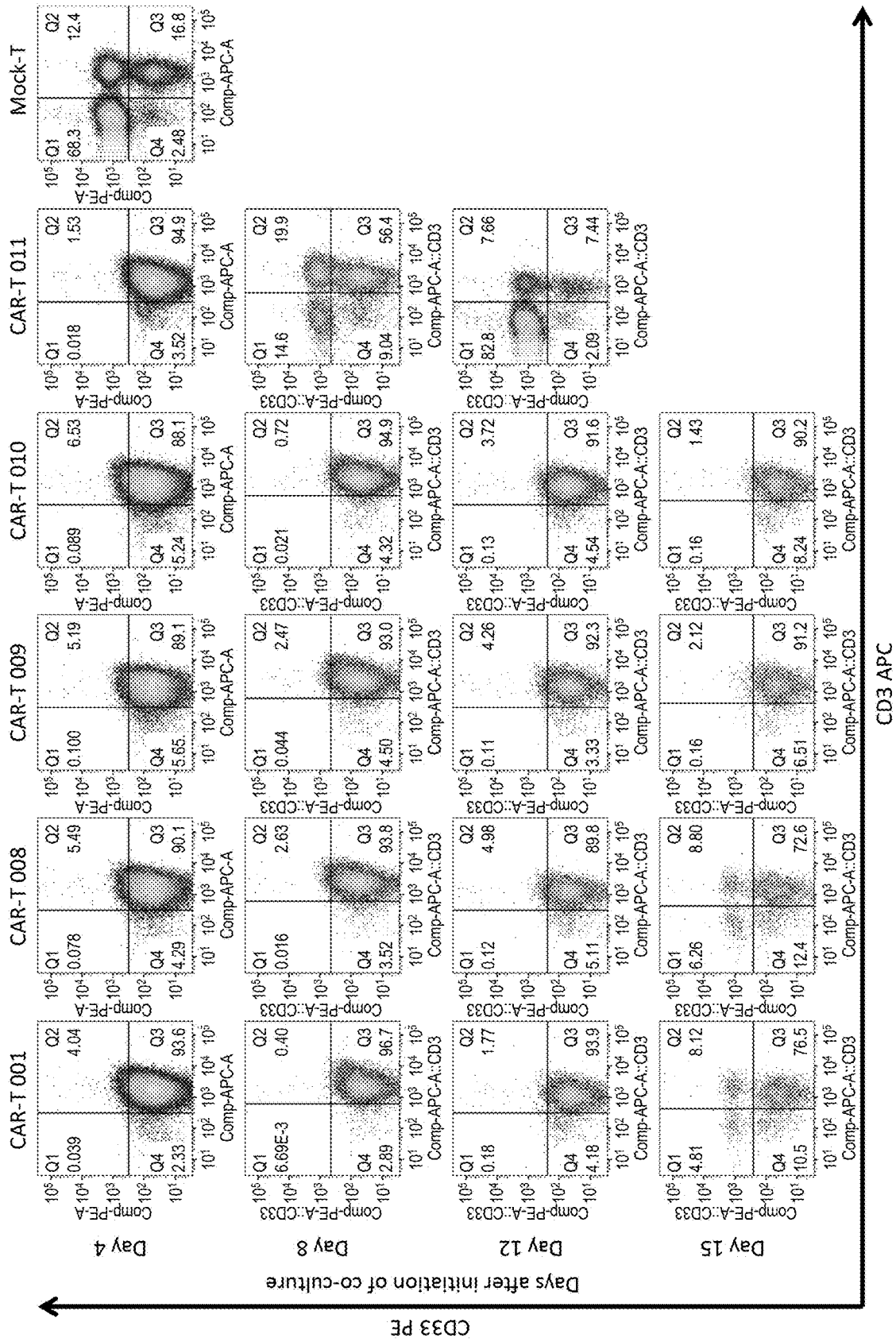
FIG. 32 shows the sustained tumor cell killing ability of CAR-T 001, CAR-T 008 to CAR-T 011 and Mock-T cells against THP-1 cells at an E to T ratio=1:1.
Figure 33:
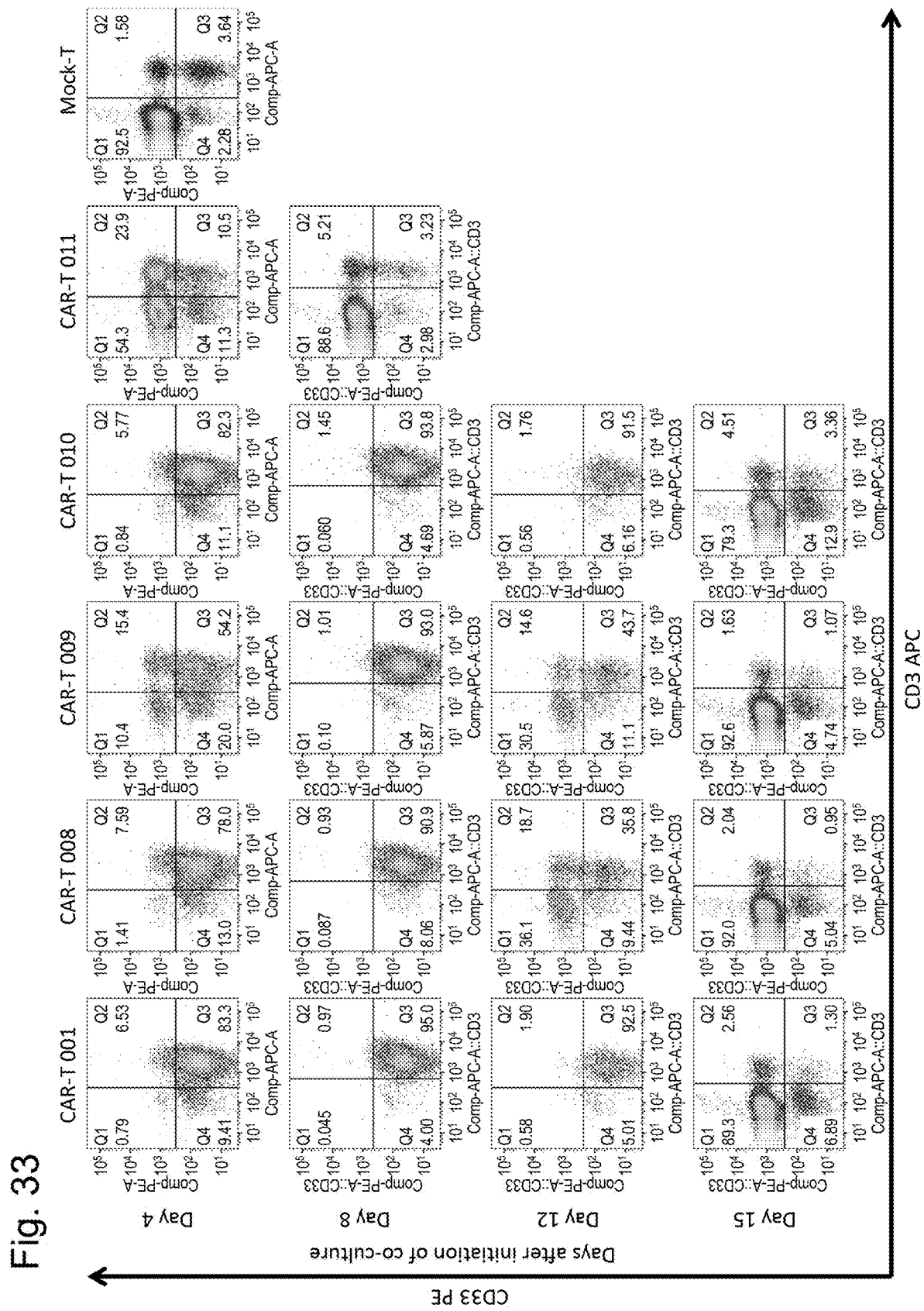
FIG. 33 shows the sustained tumor cell killing ability of CAR-T 001, CAR-T 008 to CAR-011 and a Mock-T cell against THP-1 cell at an E to T ratio=1:5.
Figure 34:
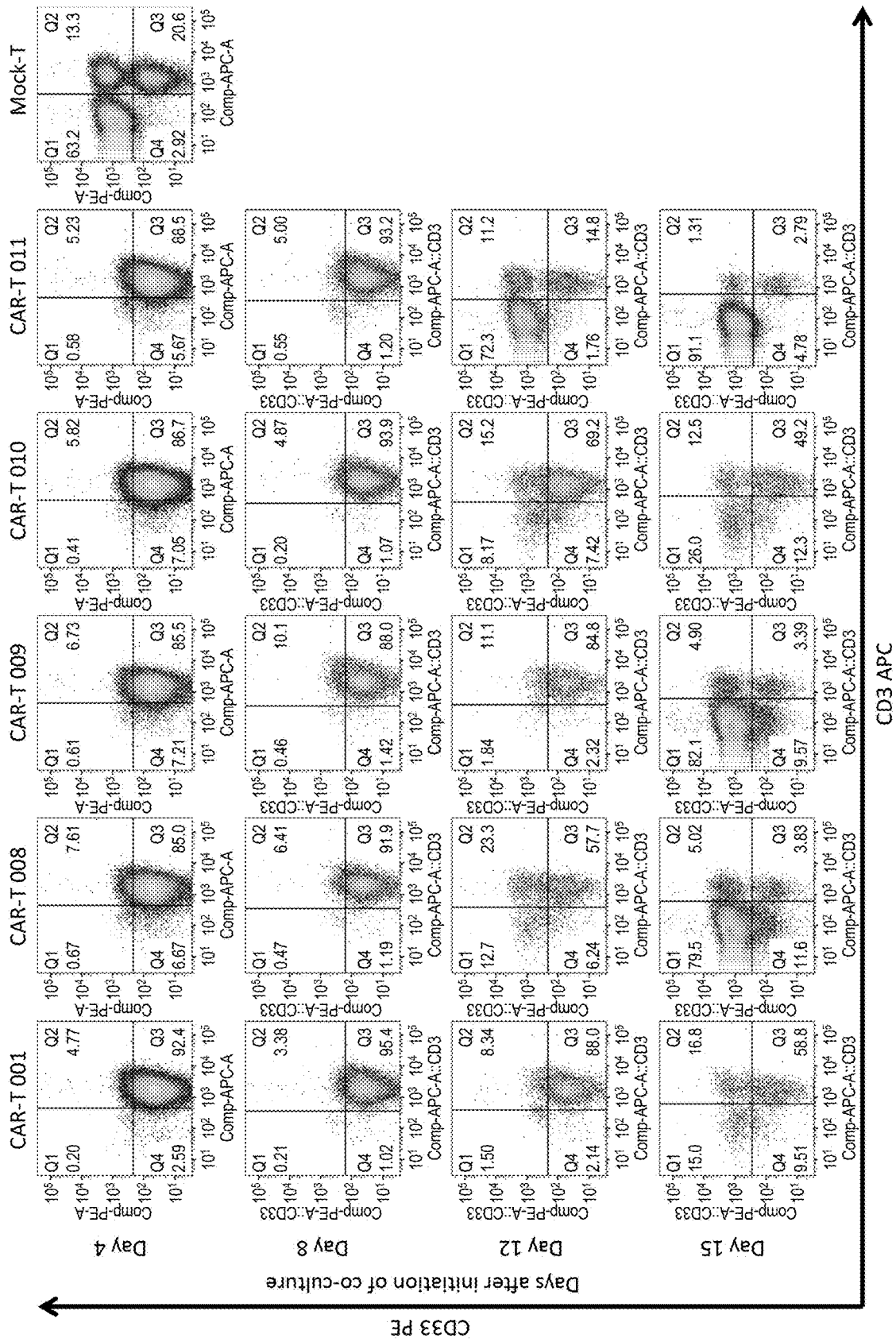
FIG. 34 shows the sustained tumor cell killing ability of CAR-T 001, CAR-T 008 to CAR-T 011 and Mock-T cells against MV4-11 cells at an E to T ratio=1:1.
Figure 35:
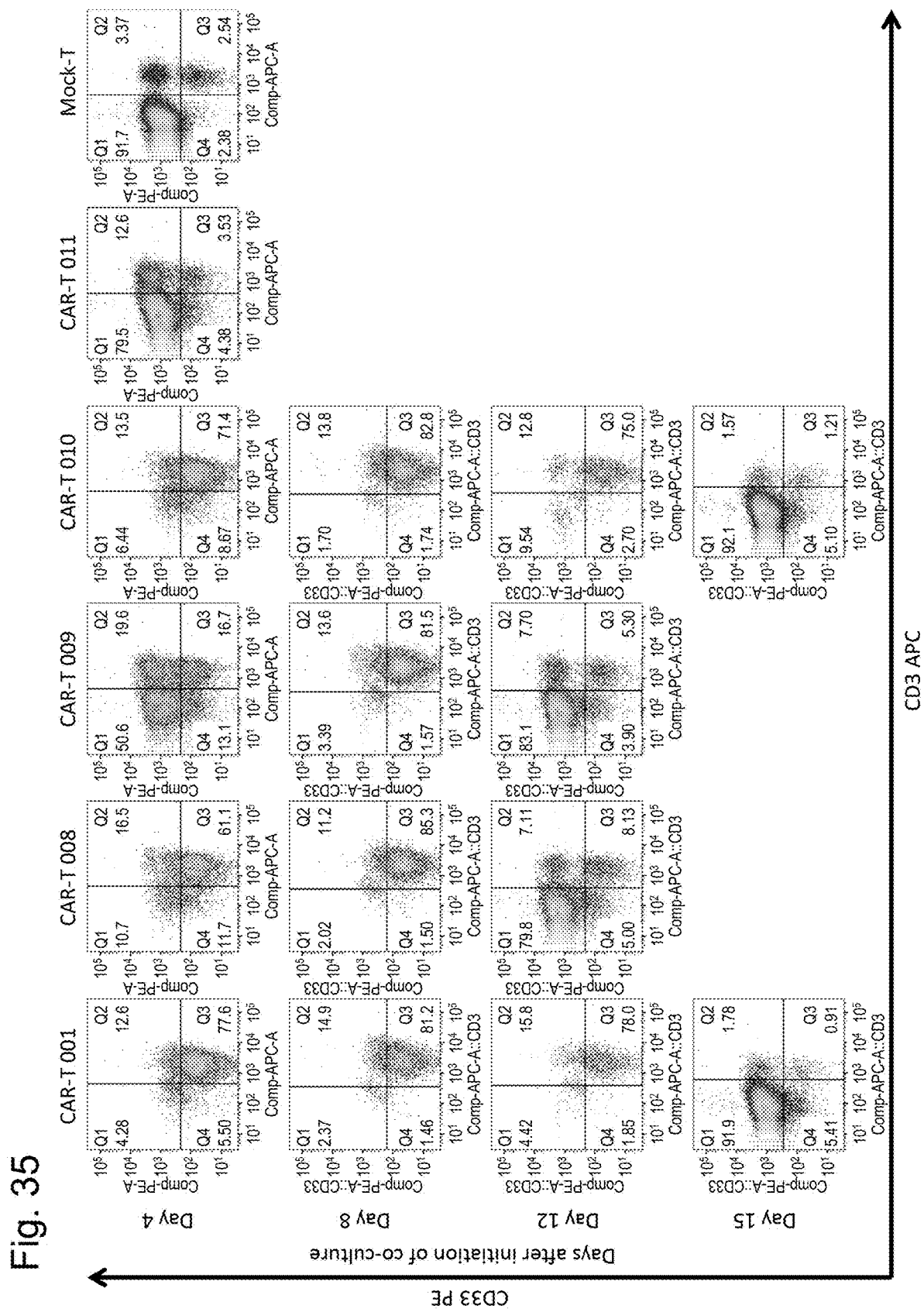
FIG. 35 shows the sustained tumor cell killing ability of CAR-T 001, CAR-T 008 to CAR-T 011 and Mock-T cells against MV4-11 cells at an E to T ratio=1:5.
Figure 38:
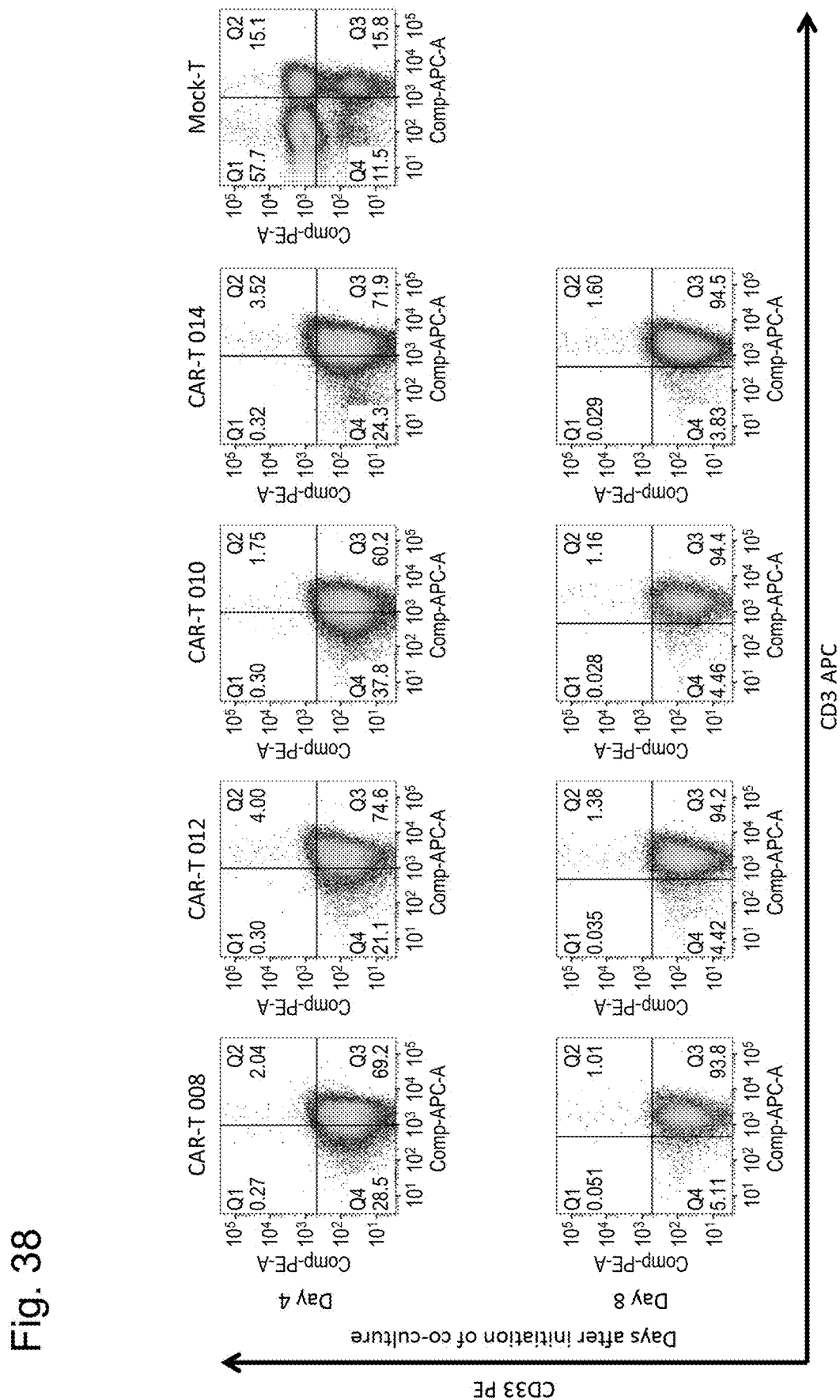
FIG. 38 shows the sustained tumor cell killing ability of CAR-T 008, 010, 012, 014 and Mock-T cells against THP-1 cells at an E to T ratio=1:1.
Figure 39:
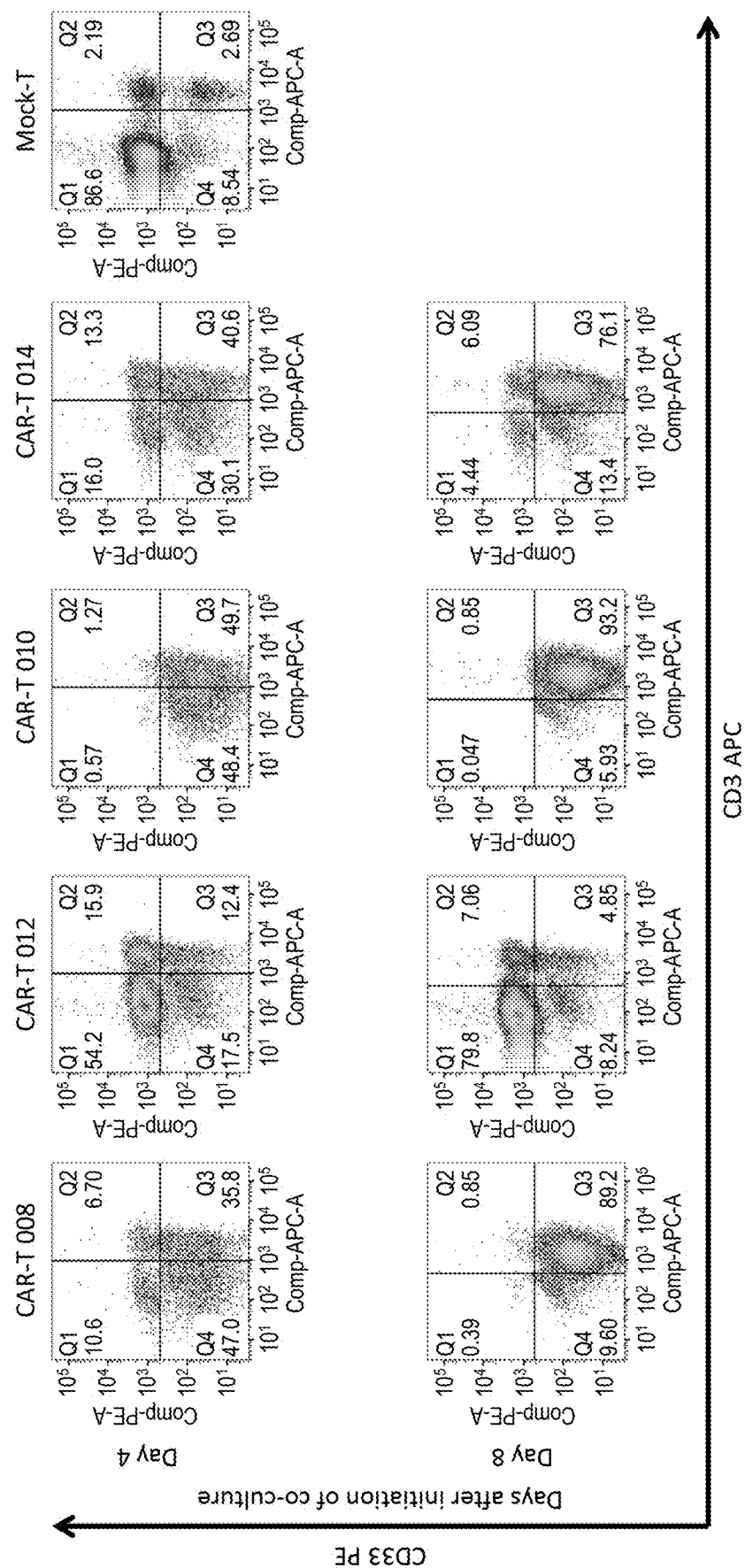
FIG. 39 shows the sustained tumor cell killing ability of CAR-T 008, 010, 012, 014 and Mock-T cells against THP-1 cells at an E to T ratio=1:5.
Figure 40:
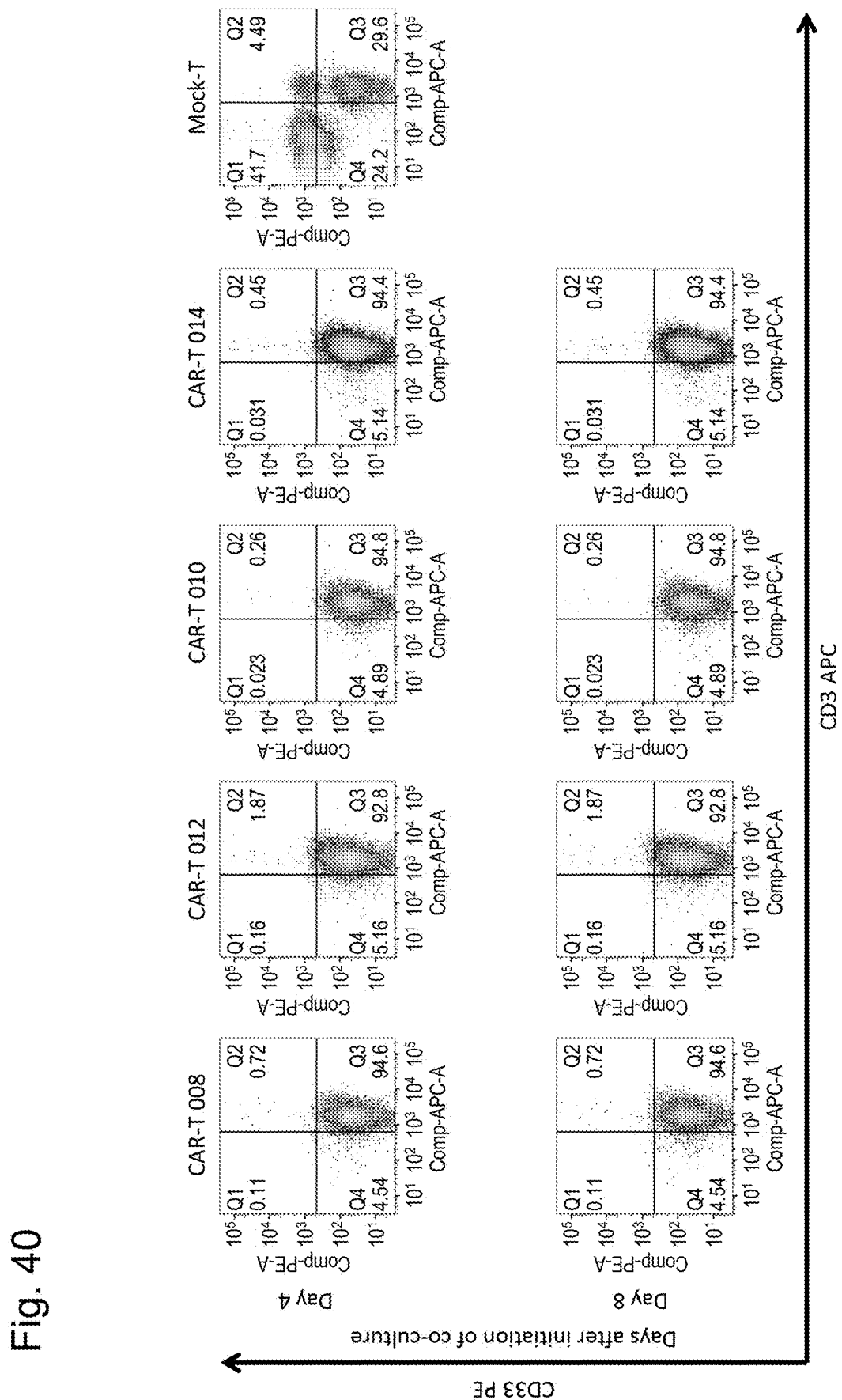
FIG. 40 shows the sustained tumor cell killing ability of CAR-T 008, 010, 012, 014 and Mock-T cells against MV4-11 cells at an E to T ratio=1:1.
Figure 41:
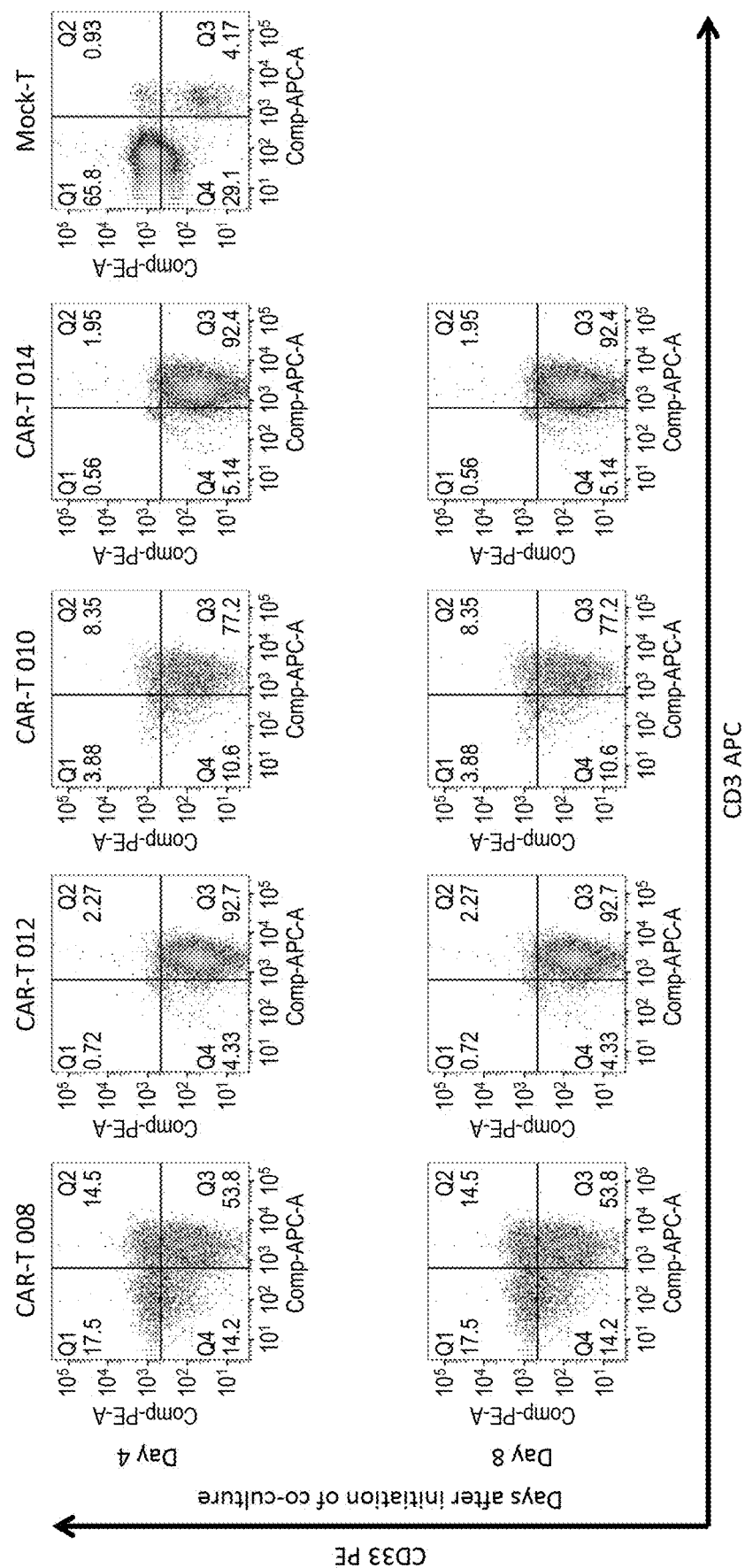
FIG. 41 shows the sustained tumor cell killing ability of CAR-T 008, 010, 012, 014 and Mock-T cells against MV4-11 cells at an E to T ratio=1:5.

The abilities of CAR-T012, CAR-T014 and Mock-T cells to kill tumor MV4-11 cells were shown in FIG. 29. The abilities of CAR-T012 and 014 to kill tumor cells were strong, more specifically, about three times as strong as that of CAR-T008 or CAR-T010 into which no shRNA was introduced.

Example 17 Evaluation of Anti-Tumor Cell Activity Persistence

To evaluate the tumor cytotoxic activity persistence of CAR-T 001, 008 to 012 and 014, long-term co-culture tests with tumor cells were carried out. More specifically, THP-1 or MV4-11 cells (American Type Culture Collection (ATCC)) were used, and these tumor cells [target (T)] were controlled with an RPMI 1640 culture medium containing 10% FBS (Thermo Fisher Scientific K.K.) such that $5 \times 10^5$ cells/mL were present, and seeded in a 48-well treatment culture plate at a ratio of 500 µL/well (the number of cells per well is $2.5 \times 10^5$). CAR-T 001, 008 to 012 and 014 [effector (E)] were diluted with an RPMI 1640 culture medium containing 10% FBS so as to obtain an E to T ratio of 1:1 and 1:5. More specifically, in the case where the E to T ratio=1:1, CAR-T was controlled such that $5 \times 10^5$ cells/mL were present, and added to the 48-well treatment culture plate having the tumor cells seeded therein, at a ratio of 500 µL/well (the number of cells per well is $2.5 \times 10^5$). Similarly, in the case of the E to T ratio=1:5, CAR-T was controlled such that $1 \times 10^5$ cells/mL were present, and added to the 48-well treatment culture plate having the tumor cells seeded therein, at a ratio of 500 µL/well (the number of cells per well is $0.5 \times 10^5$). 2 wells were prepared per group, and one well was used for "analysis" by FACS Canto II (BD) and another well was used for "continuation" to be added to fresh tumor cells in the following terms.

The co-culture test in Term 1 was carried out for 4 days. The same co-culture test was also carried out for Mock-T cells not subjected to gene introduction. As a control group, tumor cells alone of the same number of cells were cultured (CAR-T non-addition group). On day 4 of the co-culture test, cells were collected from the "analysis" well and centrifuged. To the centrifuged cells, 5 μL of AFC Anti-Human CD3 antibody (Miltenyi Biotec GmbH) and 5 μL of PE Anti-Human CD33 antibody (Miltenyi Biotec GmbH) were added and suspended, and an antibody labeling reaction was carried out at 4° C. in the dark for 20 minutes. After 20 minutes, the cells were washed with an appropriate amount of D-PBS and precipitated by centrifugation. After the supernatant was completely removed, the cells were resuspended in 450 μL of D-PBS. 50 μL of CountBright absolute counting beads (Invitrogen) were then further added to prepare a sample. The sample was analyzed using FACS Canto II and FLOWJO (Tomy Digital Biology Co., Ltd.). The number of CD33-positive cells was calculated based on the count number of beads. The process up to this time-point is specified as Term 1.

A group in which tumor cells were killed (the number of tumor cells was reduced) compared to those at the time of co-culture initiation was subjected to the following Term 2. More specifically, two wells having tumor cells seeded in advance at a ratio of $2.5 \times 10^5$ cells/500 μL/well were prepared. To the wells, the culture liquid co-cultured for "continuation" in Term 1 was equally added in an amount of 500 μL/well and co-culture was carried out for further 4 days. This 4-day or 3-day culture was repeated. The group in which the number of tumor cells increased to that at the time of co-culture initiation was not subjected to the following term.

The evaluation results of persistent anti-tumor activity against tumor cells as a target are shown in FIG. 30 to FIG. 41. It was confirmed that CAR-T 001, 008 to 012 and 014 have sustained tumor cell killing ability. With respect to MV4-11 cells, the difference in the number of times to kill tumor cells is observed depending on the structure of spacers. More specifically, CAR-T 001 and CAR-T 010 can be expected to exert a cytotoxic effect on tumor cells for a longer time.

INDUSTRIAL APPLICABILITY

The present invention provides CAR-T cells that specifically binds to a target cell expressing a human granulocyte-macrophage colony stimulating factor (GM-CSF) receptor on the cell surface and providing an excellent cytotoxic activity. The cell of the present invention can be used for an adoptive immunotherapy for diseases such as JMML.

All publications, patents and patent applications cited in the description are incorporated in then entirely herein by reference.

---

The invention claimed is:

1. A method of treating juvenile myelomonocytic leukemia (JMML) or acute myelogenous leukemia (AML) in a human patient, the method comprising: intravenously administering a pharmaceutical composition comprising a pharmaceutically acceptable carrier and cells that are genetically modified to express a chimeric antigen receptor (CAR) protein,
   wherein the CAR protein comprises a target binding domain that specifically binds to a human granulocyte-macrophage colony stimulating factor (GM-CSF) receptor, a transmembrane domain and an intracellular signaling domain, and
   wherein the genetically modified cells exert cytotoxic activity against leukemia cells in the human patient.

2. The method according to claim 1, wherein the genetically modified cells are further genetically modified to contain an interfering RNA to inhibit expression of human GM-CSF in the genetically modified cells.

3. The method according to claim 1,
   wherein the CAR protein is expressed from a first polynucleotide on a first introduced vector comprising a first expression control sequence operatively linked to the first polynucleotide.

4. The method according to claim 3, wherein the genetically modified cells are further genetically modified to express an interfering RNA to inhibit expression of human GM-CSF in the genetically modified cells, and wherein the interfering RNA is expressed from a second polynucleotide on one of a second introduced vector comprising a second expression control sequence operatively linked to the second polynucleotide, and the first introduced vector.

5. The method according to claim 1, wherein the genetically modified cells are selected from the group consisting of T cells, precursor T cells, NK cells, NK-T cells, and a combination thereof.

6. The method according to claim 2, wherein the interfering RNA is an siRNA or an shRNA.

* * * * *

SEQUENCE LISTING

```
<160> NUMBER OF SEQ ID NOS: 42

<210> SEQ ID NO 1
<211> LENGTH: 800
<212> TYPE: DNA
<213> ORGANISM: Homo sapiens
<220> FEATURE:
<221> NAME/KEY: CDS
<222> LOCATION: (33)..(467)

<400> SEQUENCE: 1
acacagagag aaaggctaaa gttctctgga gg atg tgg ctg cag agc ctg ctg            53
                                    Met Trp Leu Gln Ser Leu Leu
                                     1               5 ctc ttg ggc act gtg gcc tgc agc atc tct gca ccc gcc cgc tcg ccc          101
Leu Leu Gly Thr Val Ala Cys Ser Ile Ser Ala Pro Ala Arg Ser Pro
         10                  15                  20 agc ccc agc acg cag ccc tgg gag cat gtg aat gcc atc cag gag gcc          149
Ser Pro Ser Thr Gln Pro Trp Glu His Val Asn Ala Ile Gln Glu Ala
     25                  30                  35 cgg cgt ctc ctg aac ctg agt aga gac act gct gct gag atg aat gaa          197
Arg Arg Leu Leu Asn Leu Ser Arg Asp Thr Ala Ala Glu Met Asn Glu
 40                  45                  50                  55 aca gta gaa gtc atc tca gaa atg ttt gac ctc cag gag ccg acc tgc          245
Thr Val Glu Val Ile Ser Glu Met Phe Asp Leu Gln Glu Pro Thr Cys
                 60                  65                  70 cta cag acc cgc ctg gag ctg tac aag cag ggc ctg cgg ggc agc ctc          293
Leu Gln Thr Arg Leu Glu Leu Tyr Lys Gln Gly Leu Arg Gly Ser Leu
             75                  80                  85 acc aag ctc aag ggc ccc ttg acc atg atg gcc agc cac tac aag cag          341
Thr Lys Leu Lys Gly Pro Leu Thr Met Met Ala Ser His Tyr Lys Gln
         90                  95                 100 cac tgc cct cca acc ccg gaa act tcc tgt gca acc cag att atc acc          389
His Cys Pro Pro Thr Pro Glu Thr Ser Cys Ala Thr Gln Ile Ile Thr
    105                 110                 115
```

```
ttt gaa agt ttc aaa gag aac ctg aag gac ttt ctg ctt gtc atc ccc     437
Phe Glu Ser Phe Lys Glu Asn Leu Lys Asp Phe Leu Leu Val Ile Pro
120                 125                 130                 135 ttt gac tgc tgg gag cca gtc cag gag tga daccggccag atgaggctgg       487
Phe Asp Cys Trp Glu Pro Val Gln Glu
                140 ccaagccggg gagctgctct ctcatgaaac aagagctaga aactcaggat ggtcatcttg   547 gagggaccaa gggtgggcc acagccatgg tgggagtggc ctggacctgc cctgggccac    607 actgaccctg atacaggcat ggcagaagaa tgggaatatt ttatactgac agaaatcagt  667 aatatttata tatttatatt tttaaaatat ttatttattt atttatttaa gttcatattc  727 catatttatt caagatgttt taccgtaata attattatta aaaatatgct tctacttgaa  787 aaaaaaaaaa aaa                                                     800
```

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 3
<211> LENGTH: 432
<212> TYPE: DNA
<213> ORGANISM: Artificial
<220> FEATURE:
<223> OTHER INFORMATION: Human GM-CSF Mutant

<400> SEQUENCE: 3

```
atgtggctgc agagcctgct gctcttgggc actgtggcct gcagcatctc tgcacccgcc    60
cgctcgccca gccccagcac gcagccctgg gagcatgtga atgccatcca ggaggcccgg   120
cgtctcctga atctgagcag

```
gaaagtttca aagagaacct gaaggacttt ctgcttgtca tccccttttga ctgctgggag    420 ccagtccagg ag                                                         432
```

<210> SEQ ID NO 4
<211> LENGTH: 144
<212> TYPE: PRT
<213> ORGANISM: Artificial
<220> FEATURE:
<223> OTHER INFORMATION: Human GM-CSF Mutant

<400> SEQUENCE: 4

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
                35                  40                  45

Thr Ala

```
cacgaagacc ctgaggtcaa gttcaactgg tacgtggacg gcgtggaggt gcataatgcc      180
aagacaaagc cgcgggagga gcagtacaac agcacgtacc gtgtggtcag cgtcctcacc      240
gtcctgcacc aggactggct gaatggcaag gagtacaagt gcaaggtctc caacaaagcc      300
ctcccagccc ccatcgagaa aaccatctcc aaagccaaa                             339
```

<210> SEQ ID NO 8
<211> LENGTH: 113
<212> TYPE: PRT
<213> ORGANISM: Homo sapiens

<400> SEQUENCE: 8

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys
```

<210> SEQ ID NO 9
<211> LENGTH: 321
<212> TYPE: DNA
<213> ORGANISM: Homo sapiens

<400> SEQUENCE: 9

```
gggcagcccc gagaaccaca ggtgtacacc ctgcccccat cccgggatga gctgaccaag      60
aaccaggtca gcctgacctg cctggtcaaa ggcttctatc ccagcgacat cgccgtggag      120
tgggagagca atgggcaacc ggagaacaac tacaagacca cgcctcccgt gctggactcc      180
gacggctcct tcttcctcta cagcaagctc accgtggaca agagcaggtg gcagcagggg      240
aacgtcttct catgctccgt gatgcatgag gctctgcaca accactacac gcagaagagc      300
ctctccctgt ctccgggtaa a                                                 321
```

<210> SEQ ID NO 10
<211> LENGTH: 107
<212> TYPE: PRT
<213> ORGANISM: Homo sapiens

<400> SEQUENCE: 10

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60
```

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 81
<212> TYPE: DNA
<213> ORGANISM: Homo sapiens

<400> SEQUENCE: 11
ttttgggtgc tggtggtggt tggtggagtc ctggcttgct atagcttgct agtaacagtg    60
gcctttatta ttttctgggt g                                              81

<210> SEQ ID NO 12
<211> LENGTH: 27
<212> TYPE: PRT
<213> ORGANISM: Homo sapiens

<400> SEQUENCE: 12

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 13
<211> LENGTH: 123
<212> TYPE: DNA
<213> ORGANISM: Homo sapiens

<400> SEQUENCE: 13
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 14
<211> LENGTH: 41
<212> TYPE: PRT
<213> ORGANISM: Homo sapiens

<400> SEQUENCE: 14

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 15
<211> LENGTH: 339
<212> TYPE: DNA
<213> ORGANISM: Homo sapiens

<400> SEQUENCE: 15
agagtgaagt tcagcaggag cgcagacgcc ccgcgtacc agcagggcca gaaccagctc     60
tataacgagc tcaatctagg acgaagagag gagtacgatg ttttggacaa gagacgtggc   120
cgggaccctg agatgggggg aaagccgaga aggaagaacc ctcaggaagg cctgtacaat   180

```
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                            339
```

<210> SEQ ID NO 16
<211> LENGTH: 112
<212> TYPE: PRT
<213> ORGANISM: Homo sapiens
<400> SEQUENCE: 16

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 17
<211> LENGTH: 19
<212> TYPE: DNA
<213> ORGANISM: Artificial
<220> FEATURE:
<223> OTHER INFORMATION: siRNA sense
<400> SEQUENCE: 17

```
gaacctgagt agagacact                                                  19
```

<210> SEQ ID NO 18
<211> LENGTH: 19
<212> TYPE: DNA
<213> ORGANISM: Artificial
<220> FEATURE:
<223> OTHER INFORMATION: siRNA antisense
<400> SEQUENCE: 18

```
agtgtctcta ctcaggttc                                                  19
```

<210> SEQ ID NO 19
<211> LENGTH: 344
<212> TYPE: DNA
<213> ORGANISM: Artificial
<220> FEATURE:
<223> OTHER INFORMATION: polynucleotides for inducing RNAi
<400> SEQUENCE: 19

```
caattgaagg tcgggcagga agagggccta tttcccatga ttccttcata tttgcatata    60
cgatacaagg ctgttagaga gataattaga attaatttga ctgtaaacac aaagatatta   120
gtacaaaata cgtgacgtag aaagtaataa tttcttgggt agtttgcagt tttaaaatta   180
tgttttaaaa tggactatca tatgcttacc gtaacttgaa agtatttcga tttcttggct   240
```

```
ttatatatct tgtggaaagg acgaggatcc gaacctgagt agagacactt agtgctcctg    300
gttgagtgtc tctactcagg ttcttttttta agcttgatat cgat                    344

<210> SEQ ID NO 20
<211> LENGTH: 25
<212> TYPE: DNA
<213> ORGANISM: Artificial
<220> FEATURE:
<223> OTHER INFORMATION: siRNA sense

<400> SEQUENCE: 20
acacagagag aaaggctaaa gttct                                           25

<210> SEQ ID NO 21
<211> LENGTH: 25
<212> TYPE: DNA
<213> ORGANISM: Artificial
<220> FEATURE:
<223> OTHER INFORMATION: siRNA antisense

<400> SEQUENCE: 21
agaactttag cctttctctc tgtgt                                           25

<210> SEQ ID NO 22
<211> LENGTH: 65
<212> TYPE: DNA
<213> ORGANISM: Artificial
<220> FEATURE:
<223> OTHER INFORMATION: shRNA

<400> SEQUENCE: 22
acacagagag aaaggctaaa gttcttagtg ctcctggttg agaactttag cctttctctc    60
tgtgt                                                                 65

<210> SEQ ID NO 23
<211> LENGTH: 25
<212> TYPE: DNA
<213> ORGANISM: Artificial
<220> FEATURE:
<223> OTHER INFORMATION: siRNA sense

<400> SEQUENCE: 23
gagagaaagg ctaaagttct ctgga                                           25

<210> SEQ ID NO 24
<211> LENGTH: 25
<212> TYPE: DNA
<213> ORGANISM: Artificial
<220> FEATURE:
<223> OTHER INFORMATION: siRNA antisense

<400> SEQUENCE: 24
tccagagaac tttagccttt ctctc                                           25

<210> SEQ ID NO 25
<211> LENGTH: 65
<212> TYPE: DNA
<213> ORGANISM: Artificial
<220> FEATURE:
<223> OTHER INFORMATION: shRNA

<400> SEQUENCE: 25
gagagaaagg ctaaagttct ctggatagtg ctcctggttg tccagagaac tttagccttt    60
ctctc                                                                 65
```

```
<210> SEQ ID NO 26
<211> LENGTH: 25
<212> TYPE: DNA
<213> ORGANISM: Artificial
<220> FEATURE:
<223> OTHER INFORMATION: siRNA sense

<400> SEQUENCE: 26
gctgctctct catgaaacaa gagct                                          25

<210> SEQ ID NO 27
<211> LENGTH: 25
<212> TYPE: DNA
<213> ORGANISM: Artificial
<220> FEATURE:
<223> OTHER INFORMATION: siRNA antisense

<400> SEQUENCE: 27
agctcttgtt tcatgagaga gcagc                                          25

<210> SEQ ID NO 28
<211> LENGTH: 65
<212> TYPE: DNA
<213> ORGANISM: Artificial
<220> FEATURE:
<223> OTHER INFORMATION: shRNA

<400> SEQUENCE: 28
gctgctctct catgaaacaa gagcttagtg ctcctggttg agctcttgtt tcatgagaga    60
gcagc                                                                65

<210> SEQ ID NO 29
<211> LENGTH: 347
<212> TYPE: DNA
<213> ORGANISM: Artificial
<220> FEATURE:
<223> OTHER INFORMATION: polynucleotides for inducing RNAi

<400> SEQUENCE: 29
caattgaagg tcgggcagga agagggccta tttcccatga ttccttcata tttgcatata    60
cgatacaagg ctgttagaga gataattaga attaatttga ctgtaaacac aaagatatta   120
gtacaaaata cgtgacgtag aaagtaataa tttcttgggt agtttgcagt tttaaaatta   180
tgttttaaaa tggactatca tatgcttacc gtaacttgaa agtatttcga tttcttggct   240
ttatatatct tgtggaaagg acgaggatcc acacagagag aaaggctaaa gttcttagtg   300
ctcctggttg agaactttag cctttctctc tgtgtttttt tatcgat                 347

<210> SEQ ID NO 30
<211> LENGTH: 347
<212> TYPE: DNA
<213> ORGANISM: Artificial
<220> FEATURE:
<223> OTHER INFORMATION: polynucleotides for inducing RNAi

<400> SEQUENCE: 30
caattgaagg tcgggcagga agagggccta tttcccatga ttccttcata tttgcatata    60
cgatacaagg ctgttagaga gataattaga attaatttga ctgtaaacac aaagatatta   120
gtacaaaata cgtgacgtag aaagtaataa tttcttgggt agtttgcagt tttaaaatta   180
tgttttaaaa tggactatca tatgcttacc gtaacttgaa agtatttcga tttcttggct   240
```
ttatatatct tgtggaaagg acgaggatcc gagagaaagg ctaaagttct ctggatagtg        300
ctcctggttg tccagagaac tttagccttt ctctcttttt tatcgat                     347

<210> SEQ ID NO 31
<211> LENGTH: 347
<212> TYPE: DNA
<213> ORGANISM: Artificial
<220> FEATURE:
<223> OTHER INFORMATION: polynucleotides for inducing RNAi

<400> SEQUENCE: 31
caattgaagg tcgggcagga agagggccta tttcccatga ttccttcata tttgcatata        60
cgatacaagg ctgttagaga gataattaga attaatttga ctgtaaacac aaagatatta       120
gtacaaaata cgtgacgtag aaagtaataa tttcttgggt agtttgcagt tttaaaatta       180
tgttttaaaa tggactatca tatgcttacc gtaacttgaa agtatttcga tttcttggct       240
ttatatatct tgtggaaagg acgaggatcc gctgctctct catgaaacaa gagcttagtg       300
ctcctggttg agctcttgtt tcatgagaga gcagcttttt tatcgat                     347

<210> SEQ ID NO 32
<211> LENGTH: 346
<212> TYPE: DNA
<213> ORGANISM: Artificial
<220> FEATURE:
<223> OTHER INFORMATION: polynucleotides for inducing RNAi

<400> SEQUENCE: 32
caattgaagg tcgggcagga agagggccta tttcccatga ttccttcata tttgcatata        60
cgatacaagg ctgttagaga gataattaga attaatttga ctgtaaacac aaagatatta       120
gtacaaaata cgtgacgtag aaagtaataa tttcttgggt agtttgcagt tttaaaatta       180
tgttttaaaa tggactatca tatgcttacc gtaacttgaa agtatttcga tttcttggct       240
ttatatatct tgtggaaagg acgaggatcc gtcttaatcg cgtataaggc tagtgctcct       300
ggttggcctt atacgcgatt aagactttt taagcttgat atcgat                       346

<210> SEQ ID NO 33
<211> LENGTH: 30
<212> TYPE: DNA
<213> ORGANISM: Artificial
<220> FEATURE:
<223> OTHER INFORMATION: forward primer for constructing GMR.CAR dCH2CH3

<400> SEQUENCE: 33
ttttgggtgc tggtggtggt tggtggagtc                                         30

<210> SEQ ID NO 34
<211> LENGTH: 28
<212> TYPE: DNA
<213> ORGANISM: Artificial
<220> FEATURE:
<223> OTHER INFORMATION: reverse primer for constructing GMR.CAR dCH2CH3

<400> SEQUENCE: 34
tgggcatgtg tgagttttgt caggagat                                           28

<210> SEQ ID NO 35
<211> LENGTH: 27
<212> TYPE: DNA
<213> ORGANISM: Artificial
<220> FEATURE:
<223> OTHER INFORMATION: forward primer for constructing GMR.CAR dCH2

<400> SEQUENCE: 35
gggcagcccc gagaaccaca ggtgtac                                        27

<210> SEQ ID NO 36
<211> LENGTH: 34
<212> TYPE: DNA
<213> ORGANISM: Artificial
<220> FEATURE:
<223> OTHER INFORMATION: reverse primer for constructing GMR.CAR dCH2

<400> SEQUENCE: 36
tgggcatgtg tgagtttgt caggagattt gggc                                 34

<210> SEQ ID NO 37
<211> LENGTH: 70
<212> TYPE: DNA
<213> ORGANISM: Artificial
<220> FEATURE:
<223> OTHER INFORMATION: forward primer for constructing GMR.CAR
    dCH2+G4S3

<400> SEQUENCE: 37
ggtggtggtg gatccggcgg cggcggctcc ggtggtggtg gttctaaaga tcccaaattt    60
tgggtgctgg                                                           70

<210> SEQ ID NO 38
<211> LENGTH: 34
<212> TYPE: DNA
<213> ORGANISM: Artificial
<220> FEATURE:
<223> OTHER INFORMATION: reverse primer for constructing GMR.CAR
    dCH2+G4S3

<400> SEQUENCE: 38
tgggcatgtg tgagtttgt caggagattt gggc                                 34

<210> SEQ ID NO 39
<211> LENGTH: 27
<212> TYPE: DNA
<213> ORGANISM: Artificial
<220> FEATURE:
<223> OTHER INFORMATION: forward primer for constructing GMR.CAR
    dhingeCH2

<400> SEQUENCE: 39
gggcagcccc gagaaccaca ggtgtac                                        27

<210> SEQ ID NO 40
<211> LENGTH: 24
<212> TYPE: DNA
<213> ORGANISM: Artificial
<220> FEATURE:
<223> OTHER INFORMATION: reverse primer for constructing GMR.CAR
    dhingeCH2

<400> SEQUENCE: 40
ctcctggact ggctcccagc agtc                                           24

<210> SEQ ID NO 41
<211> LENGTH: 45
<212> TYPE: DNA
<213> ORGANISM: Artificial
<220> FEATURE:
<223> OTHER INFORMATION: (G4S)3 sequence

```
<400> SEQUENCE: 41
ggtggtggtg gatccggcgg cggcggctcc ggtggtggtg gttct         45

<210> SEQ ID NO 42
<211> LENGTH: 15
<212> TYPE: PRT
<213> ORGANISM: Artificial
<220> FEATURE:
<223> OTHER INFORMATION: (G4S)3 sequence

<400> SEQUENCE: 42

Gly Gly Gly Gly Ser Gly Gly Gly Gly Ser Gly Gly Gly Gly Ser
1               5                   10                  15
```